US009999387B2

United States Patent
Rigoard et al.

(10) Patent No.: US 9,999,387 B2
(45) Date of Patent: Jun. 19, 2018

(54) DEVICE AND METHOD FOR EVALUATING ANALGESIC NEUROSTIMULATION DEVICES

(71) Applicant: CENTRE HOSPITALIER UNIVERSITAIRE DE POITIERS, Poitiers (FR)

(72) Inventors: Philippe Rigoard, Poitiers (FR); Farid Guetarni, Chauvigny (FR)

(73) Assignee: CENTRE HOSPITAILIER UNIVERSITAIRE DE POITIERS, Poitiers (FR)

(*) Notice: Subject to any disclaimer, the term of this patent is extended or adjusted under 35 U.S.C. 154(b) by 2 days.

(21) Appl. No.: 15/021,390

(22) PCT Filed: Aug. 14, 2014

(86) PCT No.: PCT/FR2014/000186
§ 371 (c)(1),
(2) Date: Mar. 11, 2016

(87) PCT Pub. No.: WO2015/036660
PCT Pub. Date: Mar. 19, 2015

(65) Prior Publication Data
US 2016/0220178 A1 Aug. 4, 2016

(30) Foreign Application Priority Data

Sep. 13, 2013 (FR) ...................... 13 58850

(51) Int. Cl.
*G09G 5/14* (2006.01)
*G06F 3/048* (2013.01)
(Continued)

(52) U.S. Cl.
CPC .......... *A61B 5/4848* (2013.01); *A61B 5/1072* (2013.01); *A61B 5/4824* (2013.01);
(Continued)

(58) Field of Classification Search
CPC combination set(s) only.
See application file for complete search history.

(56) References Cited

U.S. PATENT DOCUMENTS 6,308,102 B1 * 10/2001 Sieracki ............. A61N 1/36071
607/59
7,374,536 B1 5/2008 Taylor
(Continued)

FOREIGN PATENT DOCUMENTS

EP  0 618 528 A1  10/1994
WO  02/21447 A1  3/2002

OTHER PUBLICATIONS

International Search Report dated Nov. 28, 2014, in corresponding PCT application.

*Primary Examiner* — Wesner Sajous
(74) *Attorney, Agent, or Firm* — Young & Thompson

(57) ABSTRACT

In order to assist in evaluating/monitoring pain, and in treating same, a touch-sensitive graphics tool is provided with a local application (TGapps) for displaying a graphical representation of a patient's body, on which the patient can delimit a zone. A control application cooperates with the local application in order to record each delimited zone together with the corresponding surface data. The control application has a first mode in which the local application (TGapps) can be used by the patient to delimit zones of pain and a second mode in which the local application can be used by the patient to delimit treated zones. The tool is configured to activate graphical and/or numerical comparisons between the surface areas of the pain zones and the surface areas of the treated zones. In this way, it is possible to evaluate pain and the effects of treatment.

22 Claims, 37 Drawing Sheets

(51) Int. Cl.
- *G06T 11/00* (2006.01)
- *G06T 11/20* (2006.01)
- *G06T 11/40* (2006.01)
- *G06T 11/60* (2006.01)
- *A61B 5/107* (2006.01)
- *A61B 7/04* (2006.01)
- *A61N 1/36* (2006.01)
- *A61B 5/00* (2006.01)
- *G06F 3/0482* (2013.01)
- *G06F 3/0484* (2013.01)
- *G06F 3/0488* (2013.01)
- *G06F 3/0481* (2013.01)

(52) U.S. Cl.
CPC .......... *A61B 5/4827* (2013.01); *A61B 5/7435* (2013.01); *A61B 7/04* (2013.01); *A61N 1/36071* (2013.01); *G06F 3/0481* (2013.01); *G06F 3/0482* (2013.01); *G06F 3/04842* (2013.01); *G06F 3/04845* (2013.01); *G06F 3/04883* (2013.01); *G06T 11/001* (2013.01); *G06T 11/206* (2013.01); *G06T 11/40* (2013.01); *G06T 11/60* (2013.01); *G09G 5/14* (2013.01); *G16H 40/63* (2018.01); *G06F 2203/04803* (2013.01); *G06T 2207/30004* (2013.01); *G06T 2207/30196* (2013.01); *G06T 2210/62* (2013.01); *G06T 2215/16* (2013.01); *G09G 2320/0693* (2013.01); *G09G 2380/08* (2013.01); *G16H 10/20* (2018.01)

(56) References Cited

U.S. PATENT DOCUMENTS

| | | | |
|---|---|---|---|
| 8,046,241 | B1 | 10/2011 | Dodson |
| 2001/0007950 | A1 | 7/2001 | North |
| 2004/0143302 | A1* | 7/2004 | Sieracki .................. A61N 1/08 607/48 |
| 2007/0213783 | A1* | 9/2007 | Pless .................. A61N 1/36071 607/42 |
| 2008/0275529 | A1* | 11/2008 | North ................. A61N 1/36071 607/59 |
| 2009/0005649 | A1 | 1/2009 | Baird |
| 2010/0007950 | A1* | 1/2010 | Yuzawa ................. G03B 21/56 359/461 |

* cited by examiner

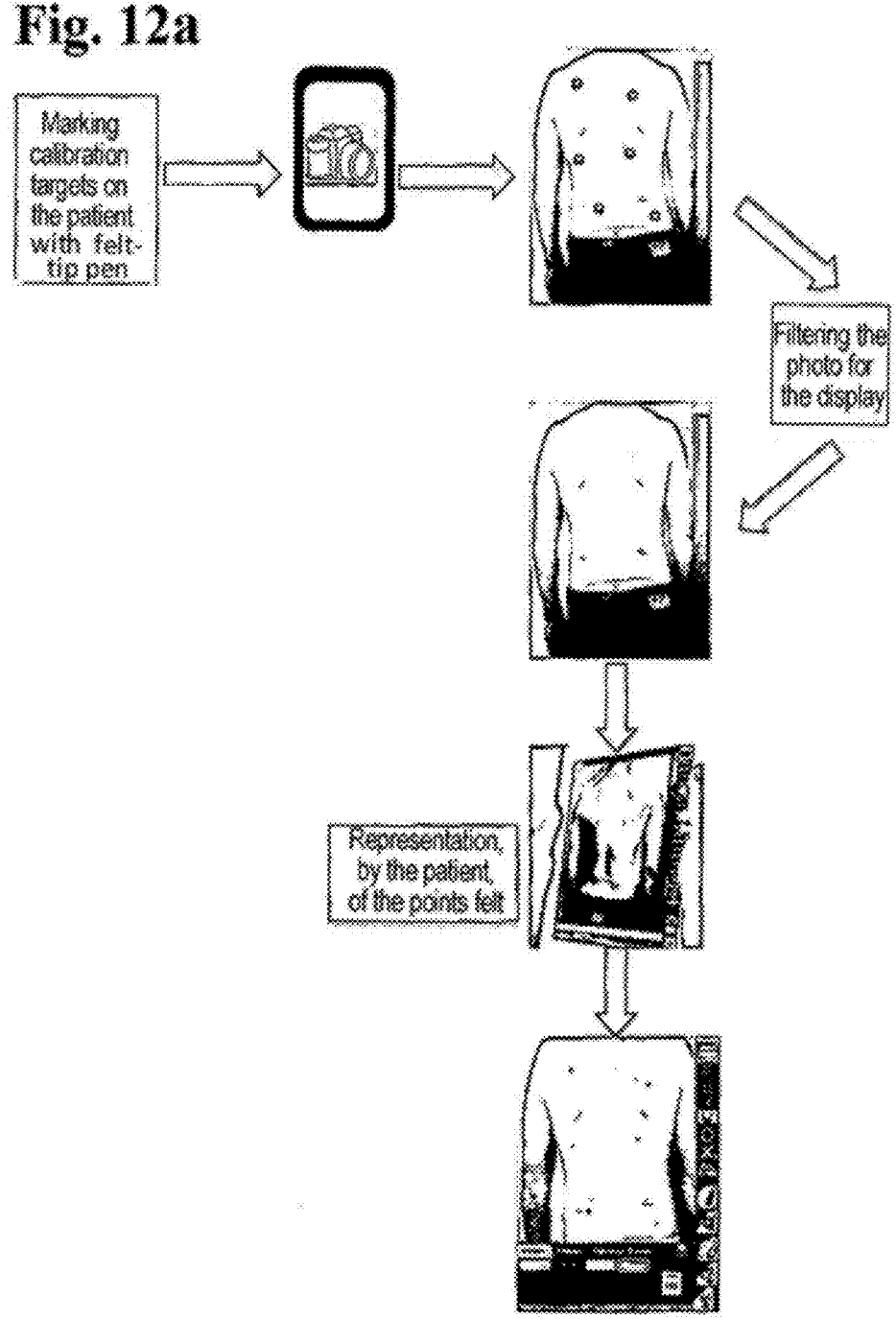

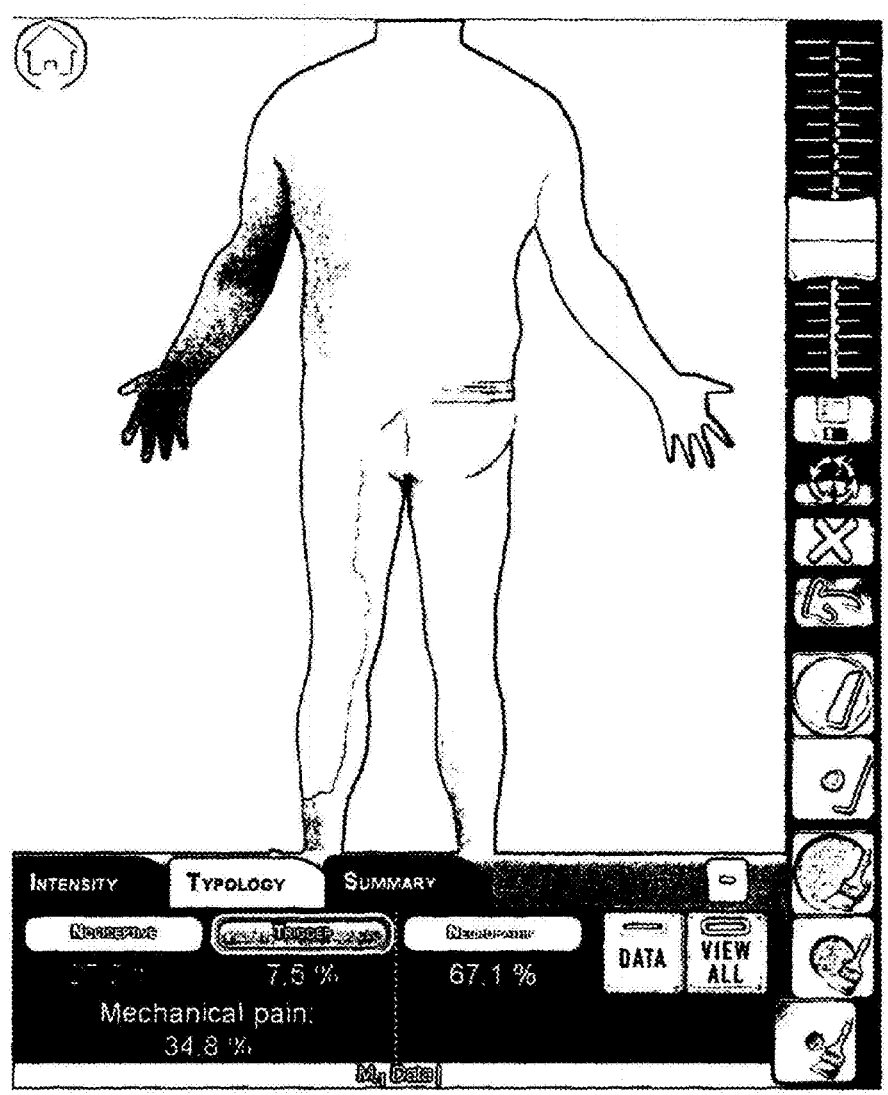

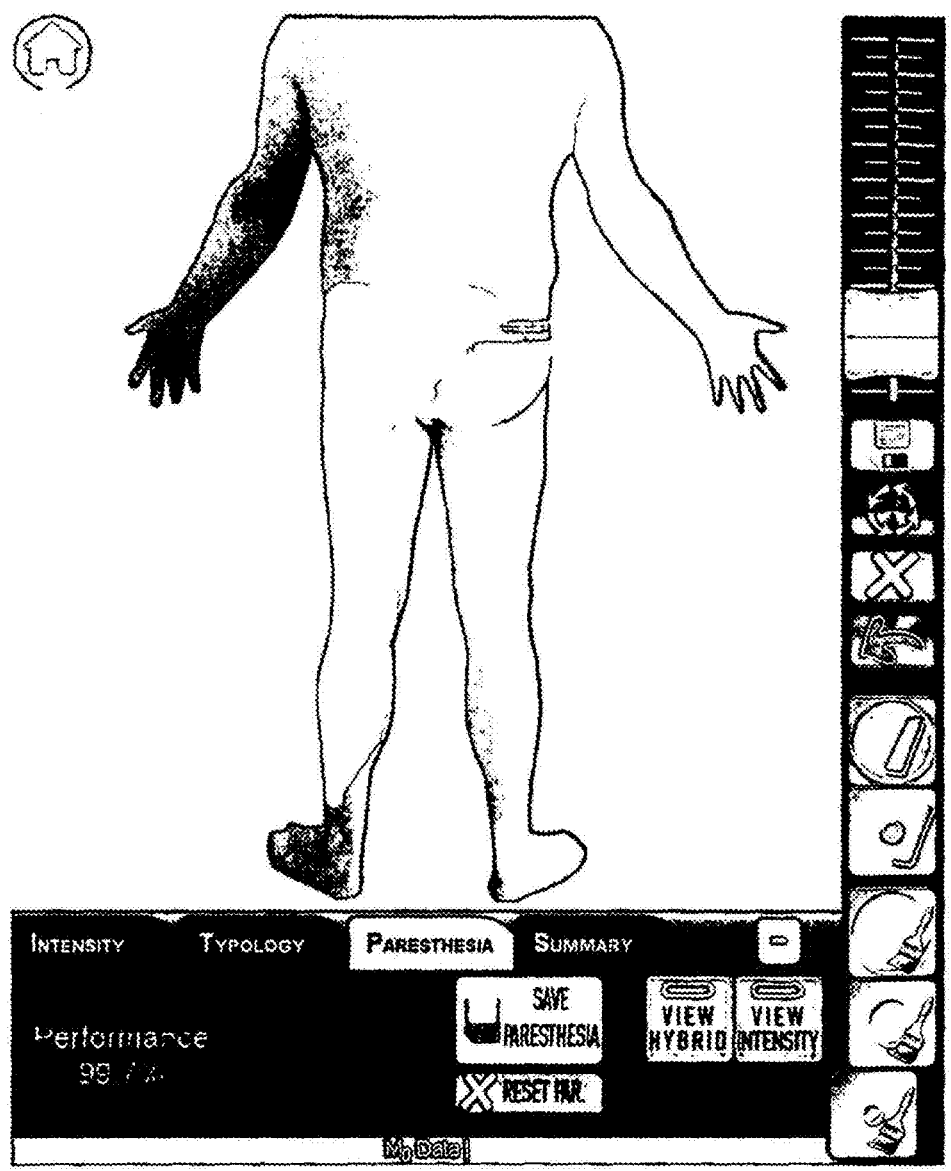

DEVICE AND METHOD FOR EVALUATING ANALGESIC NEUROSTIMULATION DEVICES

The invention relates to the medical field, in particular to the study of pain. It applies in particular, but not exclusively, to the technique of spinal cord stimulation, particularly for the management of postoperative spinal pain.

PRIOR ART

1. When a practitioner wishes to better understand the pain experienced by his patient, the simplest approach is to ask the patient to describe the pain, if necessary using auxiliary tools such as the visual analog scale (VAS), the simple verbal scale (SVS), the numerical scale (NS) or other scales intended more for chronic pain.

These scales are fairly approximate estimations of the intensity of the pain. They do not provide information on the spatial extent of the pain and on the local variations in its intensity, which will in most cases be described verbally by the patient, again in what is a fairly rough approximation.

Moreover, this description of the pain by the patient is subjective and does not necessarily correspond to the real sites of pain on the patient, and it will also be noted that several types of pain exist.

2. Spinal cord stimulation is a technique of implanted neurostimulation for attenuating or suppressing refractory chronic pain that develops over a limited cutaneous region. This technique involves implanting an electrical stimulation electrode opposite the posterior part of the spinal cord (called the "posterior cords"), the electrode being connected to a subcutaneous programmable electrical generator, which supplies the energy needed for the stimulation, over a period of several years generally. The posterior cords constituting the target of the spinal cord stimulation have the function of integrating the peripheral sensory impulses to the brain, where the sensations are analyzed and the pain message perceived. The electrical stimulation of the posterior cords acts on the fibers of fine touch, collecting the sensory impulses from the regions lying under the location of the electrode. This results in two physical effects:

This stimulation of the fibers of fine touch, called epicritic fibers, short-circuits the transmission of the pain message at the level of the spinal cord and, therefore, on the corresponding pain region. This "short-circuit" is made possible by the fact that this stimulation addresses fibers that have rapid conduction, are of large diameter and are highly myelinated (A beta fibers), which conduct more rapidly than the fibers carrying the pain impulses of the nociceptive type (A delta fibers and C fibers). By activating this medullary "filter", the spinal cord stimulation attenuates the pain sensations on the stimulated regions. It will be noted that the mechanisms of action of spinal cord stimulation are complex and are not limited to the activation of this medullary filter.

This stimulation of the fibers of epicritic touch generates, collaterally and systematically, a pleasant sensation of "paresthesia" (akin to tingling) which is perceived by the patient over the stimulated (ideally painful) region and which he likens to the spinal cord stimulation. When discussing "conventional" spinal cord stimulation, that is to say using stimulation frequencies of between 10 and 1500 Hz, there can be no effective electrical stimulation of the posterior cords of the spinal cord without paresthesia perceived at the peripheral level, and there can be no clinical analgesic efficacy of this stimulation on a given region of pain without paresthesia generated on this same region. It is therefore commonly recognized that it is necessary to "cover" the target region of pain by virtue of the neurostimulation technique used in order to be able to claim to alleviate it subsequently.

However, independently of the difficulties in ensuring a comparative and reliable evaluation of the pain throughout the course of treatment of a patient with chronic pain, there is at present no reliable device or method for providing information on the extent of the paresthetic coverage, generated by a technique of spinal cord neurostimulation implanted in a patient, using quantitative and reproducible variables and, if appropriate, permitting comparative evaluation of:

the efficacy of paresthetic coverage of a neurostimulation technique, the selectivity of a paresthetic coverage of a neurostimulation technique, the "transduction" between a quantified and measurable efficacy of an electrical coverage linked to the use of an analgesic device and its clinical analgesic efficacy.

The U.S. Pat. No. 8,046,241 (Dodson) has proposed a computer tool for evaluating pain ("Computer Pain Assessment Tool") in the form of a quantity called an "Objective Pain Value". The objective nature of this quantity is debatable. Moreover, this document uses a drawing of the pain on a human silhouette, which is not related to the measurements of the patient in real space. In other words, the metric is unsatisfactory.

The U.S. Pat. No. 7,374,536 (Taylor) has proposed a computerized process for analyzing images of pain. This document uses a drawing of the pain on a human silhouette on paper, which drawing is then scanned. Here too, the metric is unsatisfactory.

The document US 2009/0005649 (Baird et al.) discloses a system and a method for mapping the depth of a pain. For this purpose, it uses a three-dimensional human silhouette on which the user can indicate the location of the pain. A cross section of the silhouette then allows the patient to indicate the depth of the pain. However, the silhouette and the cross section are not related to the actual measurements of the patient. The metric is therefore unsatisfactory.

The document US 2001/0007950 (North et al.) discloses a system and a method of interactive neurostimulation using the cooperation of the patient. The system or method uses several neurostimulation elements implanted in a patient who draws, on a standard silhouette, his sensations in view of the stimulations, compared to the extent of his pain. However, the silhouette is not related to the actual measurements of the patient. Once again, the metric is unsatisfactory.

The present invention comes to improve the situation by providing a considerable advance in the evaluation of the pain in relation to the effects of the treatment. Moreover, the improvement also concerns in particular the drawing precision and its relationship to a real metric, and numerous other aspects which will be discussed below. Metrics will thus be attributed to the pain, for the descriptive analysis thereof, and to the paresthesias generated by a technique of implanted neurostimulation with respect to said pain, for the comparative analysis thereof; it will then be possible to carry out statistical analyses on groups of patients.

According to a first aspect of the invention, a tool is proposed for assisting in the evaluation/monitoring of pain and of a treatment, comprising:

a graphics tool equipped with a screen, such as a graphics tablet, a local application installed in the graphics tool for the purpose of displaying on the screen a graphical representation of a patient's body, while allowing a user, for example the patient, to delimit a zone on the graphical representation displayed on the screen, a control application cooperating with the local application in order to record each delimited zone together with corresponding surface data, the control application having a first mode in which the local application allows the patient to delimit pain zones, the control application having a second mode in which the local application allows the patient to delimit treated zones, the control application being configured to effect, activate or bring about graphical and/or numerical comparisons between the surface areas of the pain zones and the surface areas of the treated zones, which makes it possible to evaluate the pain and the effects of the treatment.

In the first mode, the local application can be configured to allow a patient to delimit pain zones selectively according to the type and the intensity of the pain. The types of pain can comprise at least some of the types from the following group: nociceptive pain, trigger pain, neuropathic pain, mechanical pain.

In the second mode, the treated zones can correspond to paresthesia zones resulting from the excitation by a neurostimulation device implanted in the patient, and the local application can be configured to allow paresthesia zones to be delimited selectively depending on whether the device is a neurostimulation electrode of the central nervous system or a neurostimulation electrode of the peripheral nervous system.

Preferably, the local application is configured to evaluate first surface data relating to at least one pain zone and second surface data relating to at least one paresthesia zone, while the control application is configured to compare these surface data and also to calculate a rate of paresthetic coverage and a rate of specificity of the paresthetic coverage. This allows the paresthetic coverage to be adapted by improving the specificity.

According to another aspect, each graphical delimitation is realized by filling zones with selective graphical attributes, in particular of color, at least some of the zones being partially transparent.

According to another aspect, the local application is configured to allow a real metric to be assigned to said graphical delimitations. The real metric can be obtained by applying a real scale to the silhouette of the patient, on the basis of a measured real size, such as the height of the patient. The real metric can also be obtained by processing images of the patient that are obtained from medical imaging. This makes it possible to obtain real surface areas.

In one embodiment, the local application is provided with a functionality for splitting the screen into two zones, one for the patient, and the other for medical personnel, and on which zones the mode of display of at least some of the data is different.

According to another aspect, the control application is configured to control a patient auto calibration function capable of determining the deviations between a plurality of target points designated by contact on the physical body of the patient and corresponding points indicated by the patient pointing to the graphical or cartographic representation displayed on the screen, while the delimitation, on the screen, of a zone on the graphical representation by the patient is modified as a function of these patient auto calibration deviations. This makes it possible to take into account the fact that a patient perceives points on his body in an imprecise manner, especially if he is ill. The target points can be designated successively by contact on the physical body of the patient, while the patient indicates each time, on the screen of the graphics tablet, the point on the graphical representation of his body where he feels the contact. The target points can be chosen from a predefined list of morphological markers. Finally, the patient auto calibration function is repeated several times for the same patient. Each of these features improves matters in practice.

According to another aspect, the graphics tool is equipped with a screen, in particular a touch-sensitive screen, and the control application is likewise configured to call up a patient/screen calibration function capable of determining the deviations between target points on the screen and the zones of the screen that the patient actually touches, while the delimitation, on the screen, of a zone on the graphical representation by the patient is modified as a function of these patient/screen calibration deviations.

According to another aspect, the data relating to graphical delimitation and to surface areas are stored in a dated record attached to a patient file.

The graphics tool can be set up in a network with at least one other computer, in a manner permitting mobility.

Said other central computer can be equipped with applications capable of managing a database and of performing statistical analyses on the data of this base. The statistical analyses on the data of said base can be configured to supply predictors of treatment, as a function of subpopulations of patients. The statistical analyses on the data of said base can also be configured to supply comparative tests on different electrode models.

According to another aspect, the local application can be configured to determine, between the results of two visits:
a coefficient of raw performance,
a coefficient of weighted performance, as a function of the relationship between a treatment zone and zones of pain intensity, and
a coefficient of specificity/dispersion, as a function of the relationship between the treatment zone and at least some of the zones of pain intensity,
all of these coefficients (R index) providing a powerful indicator of the suitability of a treatment.

Said coefficients can be shown graphically by telltale lights, including a comparison with respective thresholds, accompanied by at least one diagram of rectangles representing, on the one hand, the relationships between the zones of pain intensity and the part of the treatment zone which respectively affects them, and, on the other hand, the part of the treatment zone which does not affect at least some of the zones of pain intensity.

According to another aspect, the local application can be configured to determine, between the results of two visits:
at least three coefficients representing, respectively, the reduction of the surface area of pain, the reduction of the pain intensity, and the change of typology of the pain, and
at least three coefficients representing, respectively, the performance of the treatment device, the selectivity of the treatment device, and the duration of the effects of the treatment device, all of these coefficients (index RFG) providing another powerful indicator of the suitability of a treatment, usable in particular for monitoring over time.

Said coefficients can be represented graphically in the form of at least one multiaxial polygonal diagram. The multiaxial polygonal diagram can support the representation of at least two groups of said coefficients, with different graphical attributes, in particular of color, the two groups being related to at least partially different treatment conditions.

According to another aspect, the graphical representation can comprise at least two juxtaposed multiaxial polygonal diagrams, corresponding to at least partially different treatment conditions or different times.

BRIEF DESCRIPTION OF THE FIGURES

Other features and advantages of the invention will become clear on examining the following detailed description and the attached drawings. Some of the figures are shown once in color and again in black and white; the color version much better illustrates the advantages of the invention.

In the drawings:

FIG. 8 is a screenshot converted into black and white, illustrating a menu for patient entry;

FIG. 8a is the original of FIG. 8 in color;

FIG. 12a is the original of FIG. 12 in color;

FIG. 16a is the original of FIG. 16 in color;

FIG. 17a is the original of FIG. 17 in color;

The drawings and the description below mainly contain features of a certain character. The drawings form an integral part of the description and therefore may not only serve to provide a better understanding of the present invention but also to contribute to its definition, where appropriate.

The following detailed description first of all comprises a summary of the invention, drawn essentially from the French patent application No. 1358850 filed Sep. 13, 2013 and entitled "MAPPING METHOD AND SYSTEM, METHOD AND SYSTEM FOR EVALUATING THE EFFICACY OF SPINAL CORD STIMULATION".

The detailed description then comprises more in-depth and preferred embodiments of several aspects of the invention.

SUMMARY OF THE INVENTION

The invention proposes a method for mapping painful zones, a method for evaluating the efficacy of a spinal cord stimulation, a mapping system, and a system for evaluating the efficacy of spinal cord stimulation.

The mapping method is intended to:
indicate the location of the pain felt by a patient,
indicate the nature of this pain (neuropathic or mechanical), and
supply characteristics of said pain. These characteristics are in particular the skin surface affected by the pain, and the percentage of painful skin surface included within each dermatome or each lumbar region.

These results allow a physician to choose one or more electrodes to be implanted in the area of the one or more painful zones, in order to implement the technique of stimulation, for example spinal cord stimulation, aimed at alleviating the patient's pain. Some electrodes or devices will in fact be suitable to a greater or lesser degree depending on the characteristics indicated above.

Figure 1:
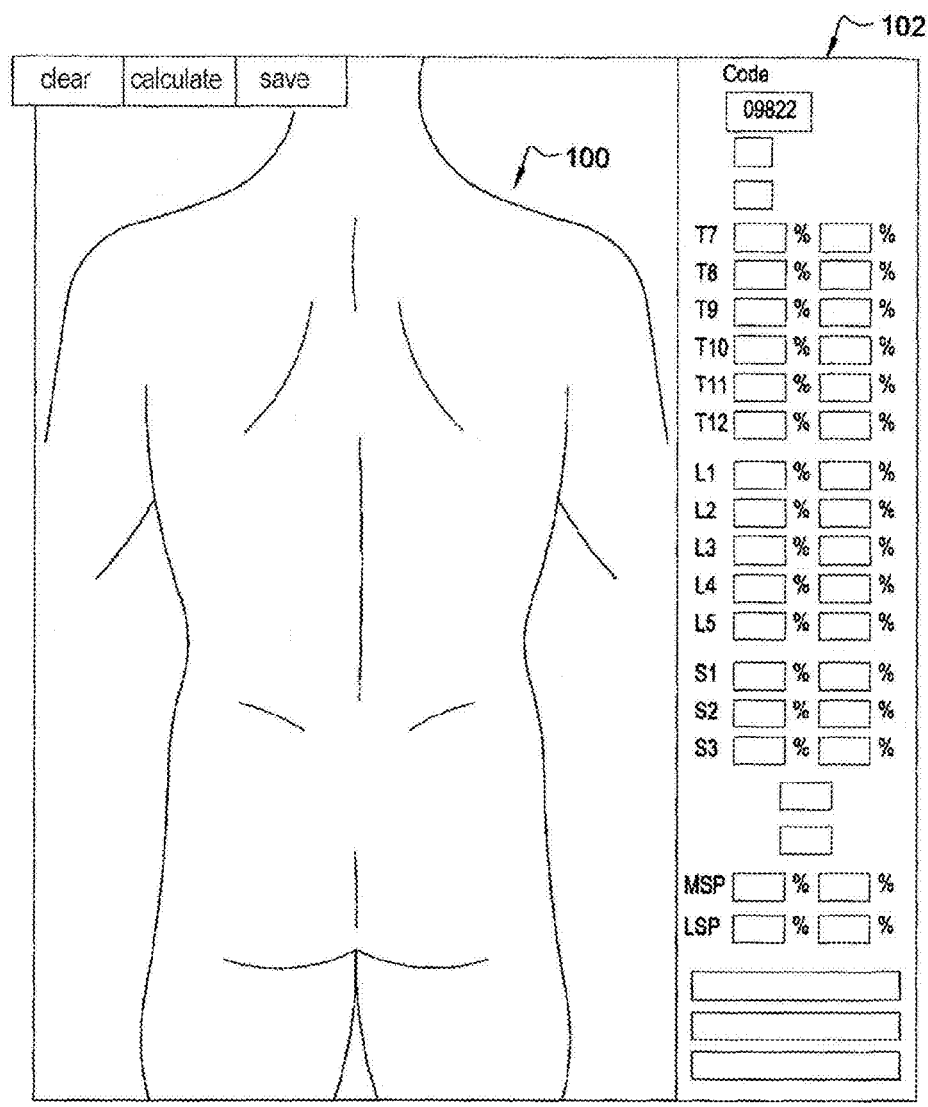
FIG. 1 illustrates the display of a silhouette (representation of a body) on a screen, according to an embodiment of the proposed mapping.
Figure 4:
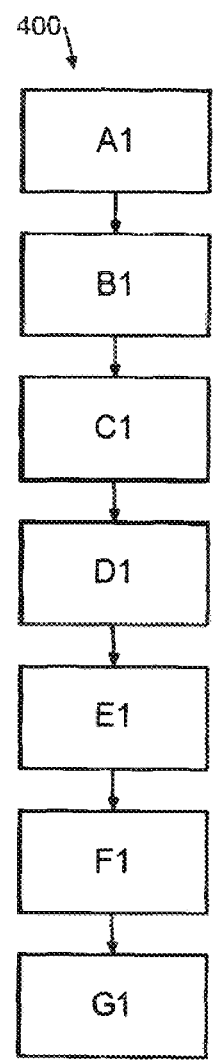
FIG. 4 illustrates steps in an embodiment of the proposed mapping method.

More precisely, with reference to FIG. 4, the mapping method 400 comprises the following steps:

A1: with reference to FIG. 1, displaying a first silhouette 100 representing the posterior aspect of a body on a first screen 102. The first screen 102 is, for example, a touch-sensitive screen, advantageously a touch-sensitive screen of a tablet. This is because a touch-sensitive screen permits ergonomic use, and a touch tablet is large enough to allow a reasonable display and small enough to take up little space. In the embodiment described, the silhouette 100 is a standard model not adapted to the morphology of the patient. However, an embodiment in which the silhouette 100 is of a form adapted to the morphology of the patient is not excluded.

Figure 2:
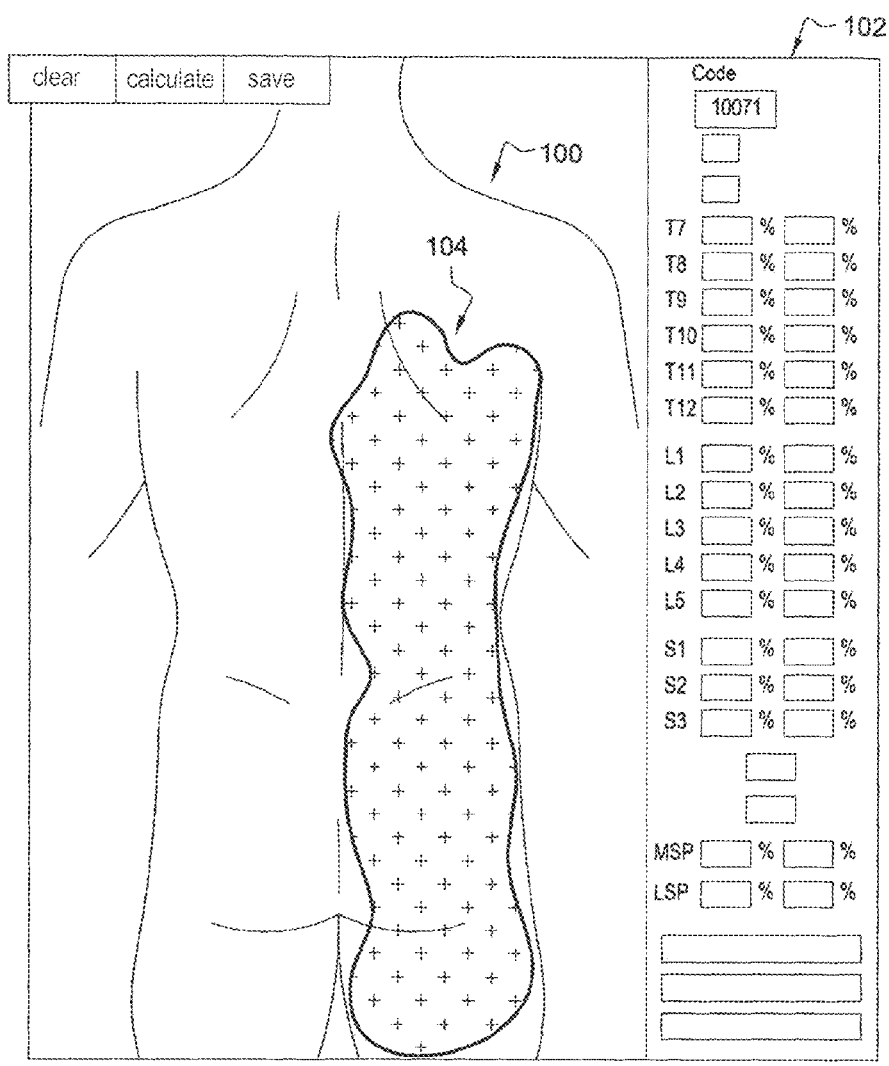
FIG. 2 illustrates the drawing of a painful zone on the silhouette from FIG. 1 and, in the right-hand panel, elements for calculating the surface area of the painful surface.

B1: with reference to FIG. 2, drawing at least one painful zone 104 on said first displayed silhouette 100, indicating the location of a pain felt by the patient. In a non-limiting embodiment in which the screen 102 is a touch-sensitive screen, the patient delimits the painful zone 104 by circling it with his finger.

More particularly, the patient can:

draw in a first way a neuropathic pain, that is to say a painful surface comprising neuropathic characteristics;

draw in a second way a mechanical pain, that is to say a painful surface comprising mechanical characteristics.

In one embodiment, the patient has a palette of two colors (at least), each color representing a type of pain. In another embodiment, the pain is shown in one and the same color, but hatching makes it possible to differentiate the type of pain. Type of pain means in particular mechanical pain or neuropathic pain. Specific criteria grouped in a questionnaire make it possible to describe pain as neuropathic. An example of a known questionnaire is the DN4 questionnaire defined in the publication: Bouhassira et al. *Comparison of pain syndromes associated with nervous or somatic lesions and development of a new neuropathic pain diagnostic questionnaire (DN4)*. Pain 205; 114:29-36.

The patient can thus indicate whether a painful zone corresponds to a neuropathic pain or a mechanical pain.

In fact, some scientists are of the opinion that stimulation, for example spinal cord stimulation, is not effective on mechanical pain. These subsidiary steps may make it possible to confirm or invalidate this opinion.

C1: determining a first number of pixels of the first screen 102 corresponding to the painful zone 104. It will be noted that the numbers of pixels corresponding to neuropathic pain and mechanical pain, or to different painful zones, are added together except in the case of an intersection, in which case the common surface area is counted only once, at least for some of the calculations, such as performance and specificity.

D1: measuring a reference distance on the patient. In the embodiment described, the reference distance corresponds to the distance between the two iliac crests of the patient. Indeed, this distance has the advantage of being substantially constant according to the build of the patient. It will be noted that other morphological references could be used, for example the distance between the shoulder blades or the distance between the mastoids, but the distance between the iliac crests is preferred. It will be appreciated that the step of measuring the reference distance can be carried out before the steps described above, or between two of these steps.

E1: converting the first number of pixels into a painful skin surface, the reference distance being used as conversion parameter. The painful skin surface is then displayed on the first screen 102, which provides the physician with information. The painful skin surface is, for example, expressed in square centimeters.

To carry out this conversion step, two coefficients are calculated:

a vertical coefficient equal to the real height of the patient divided by the number of pixels representing the height of the silhouette, a horizontal coefficient equal to the distance between the iliac crests of the patient divided by the number of pixels representing the distance between the iliac crests on the silhouette.

The painful skin surface is then equal to the product of the horizontal coefficient, the vertical coefficient and the first number of pixels corresponding to the painful zone. The product of the horizontal coefficient by the vertical coefficient gives the surface area of a pixel.

Figure 3:
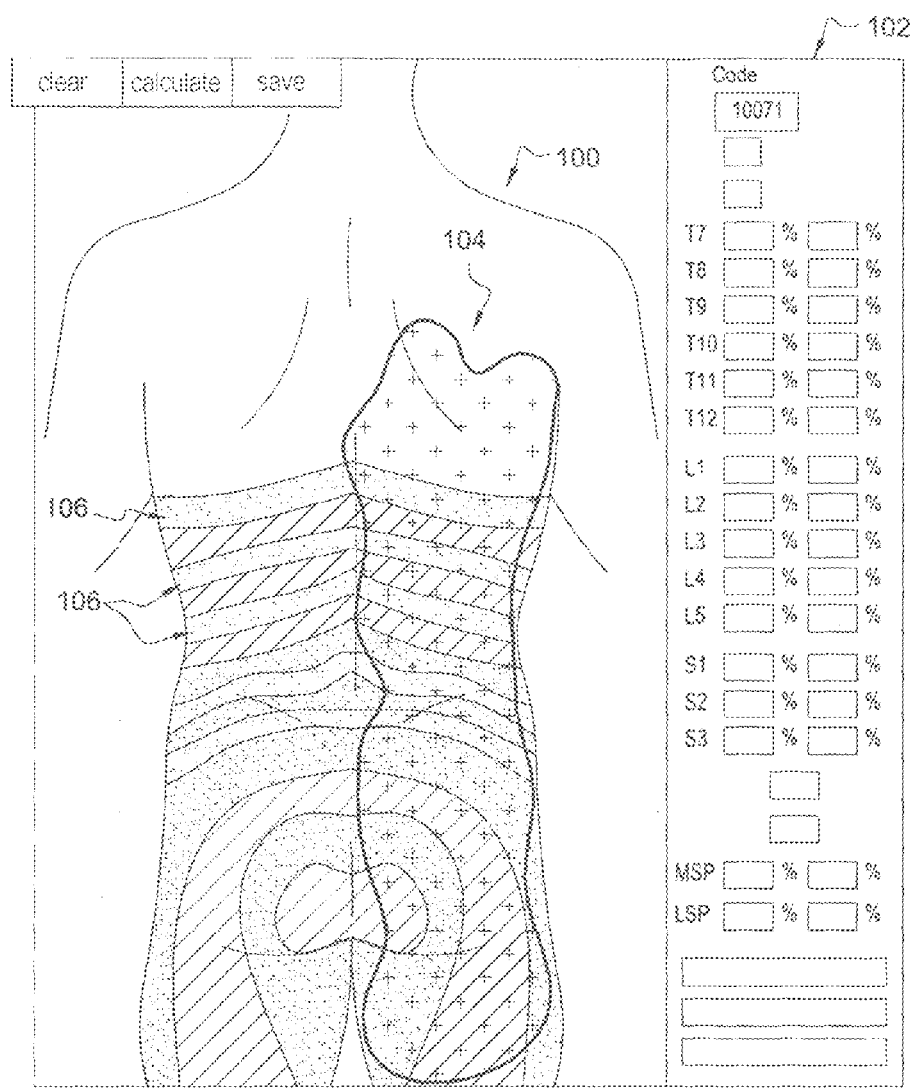
FIG. 3 illustrates the display of dermatomes (bands of cutaneous surface innervated by the same peripheral nerve) represented on the silhouette, and the calculation of ratios of painful cutaneous surface corresponding to the involvement of each of these dermatomes.

F1: determining a ratio of painful skin surface included within a region 106 of the first silhouette 100. With reference to FIG. 3, in one embodiment, the region 106 in question corresponds to a dermatome. In one embodiment, the regions 106 displayed on the silhouette 100 are superposed on the drawn painful zone 104. The region 106 could also be a lumbar region, or any other region corresponding to a known topographical notion.

Advantageously, several ratios corresponding to several regions 106 of a topographical reference system are calculated. In one embodiment, these ratios are expressed as a percentage in order to facilitate the reading. The physician can thus tell which dermatomes are implicated in the painful surface and in what proportions. In one embodiment, a correspondence table is displayed alongside the first silhouette 100, showing the ratios or the percentages of painful skin surface per region considered. The painful skin surface is thus expressed as percentages with respect to the surface representation of the different dermatomes of the dorsolumbar region in particular.

G1: in one embodiment, the first silhouette 100, on which the one or more painful zones 104 are drawn, and the characteristics of these pains are recorded on a server.

The skin surface corresponding to the painful zone drawn by the patient is a first parameter of pain quantification, of which the method permits the evaluation. This first parameter helps in choosing the appropriate therapeutic tool to be used, that is to say the type of electrode. Indeed, if the painful skin surface is estimated at 25 square centimeters, an electrode able to cover 10 square centimeters may be deemed unsuitable. It will be noted that the screen is advantageously a touch-sensitive screen, and the patient draws the painful zone using his fingers, which is more practical than using a mouse or a stylus.

On each tactile pressure, a delimitation of the painful zone is entered at the mapping level, it being possible for several zones to be drawn with or without being superposed. This mapping is calibrated with respect to the reference distance in order to extrapolate the tracings with respect to the individual concerned. The drawing is simple and can be done quickly and, furthermore, it makes it possible to delimit a surface and to identify a location and a development of the tracing over the course of the treatment of the pain.

In one non-limiting embodiment, the mapping method comprises the following step: determining a ratio of painful skin surface included within a region of the first silhouette. Said ratio of skin surface included within the region is a second parameter of pain quantification, of which the method permits the evaluation. It is in fact useful to relate the painful skin surface to known topographical notions of the body, especially delimitations approved by specialized authorities or the scientific community, for example the delimitations of high back pain/low back pain, or delimitations commonly recognized at the anatomical level, for example the dermatomes. By correlating the location of the painful skin surface with a chosen topographical reference system, the physician has access to data allowing him to suitably choose his therapeutic tools, that is to say the electrodes to be implanted.

For example, one electrode may be effective in a given region and less effective in another. It will be noted that the quantification of pain by topographic surface is important for determining the predominance and the intensity of certain types of pain and for thus explaining the pain. This step thus additionally makes it possible to identify the peripheral nervous regions that are implicated to a greater or lesser degree in the pain mechanism.

In one non-limiting embodiment, the region corresponds to a dermatome. A dermatome is a band of skin corresponding to a selective innervation of a given nerve of the body. By virtue of the mapping method according to the invention, the physician has access to the percentages of the painful skin surface included within each dermatome. In another non-limiting embodiment, the region corresponds to a lumbar region.

The mapping method 400 can be carried out at different points in time for a given patient. An initial map and follow-up maps are thus obtained, by means of which it is possible to compare the painful region before and after the patient has received a given treatment, in particular an implantation for stimulation, for example spinal cord stimulation. The evaluations can likewise be repeated over time and at several times in one day, by means of which it is possible, by implementation of data, to arrive at an averaged and more precise approximation of the painful regions over time, taking into account the changes in posture or position of the individual over a 24 hour period.

The method for evaluating the efficacy of spinal cord stimulation is used:
  to ascertain, during an operation of implanting one or more electrodes in the patient, whether the electrode is correctly positioned or whether it is advantageous to move it, and/or
  to monitor the patient in the postoperative period, that is to say to verify that the paresthetic coverage of the spinal cord stimulation is (still) effective and can continue to relieve the patient's pain, by permitting either a reduction of the painful surface areas or of the intensity of the pain.

In the first case, the spinal cord stimulation is performed during an operation for implanting said electrode. This is particularly advantageous for implanting the electrode at a site where the spinal cord stimulation will be effective. In practice, the patient is woken during the implantation operation and, by virtue of the method for evaluation of the efficacy of spinal cord stimulation according to the invention, indicates to the physician whether the electrode is placed at a suitable location. If this is not the case, the physician is then able to move the electrode before putting the patient back to sleep and terminating the implantation.

In the second case, the spinal cord stimulation is performed after an operation for implanting said electrode, for example several months or several years after the operation. It is in this way possible to verify that the patient is responding correctly to the spinal cord stimulations and that the painful zone is still covered by the paresthesia zone generated by the stimulation. It is in fact sometimes observed that the paresthesia weakens over time or even disappears. Thus, cartographic monitoring of the patient during the implantation procedure is possible in real time.

Figure 5:
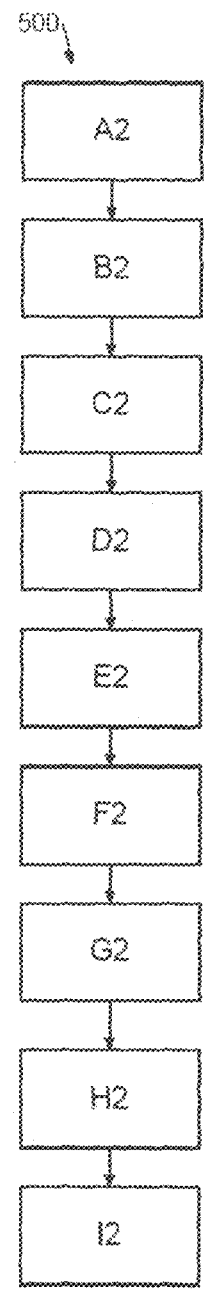
FIG. 5 illustrates steps in a method for evaluating the efficacy of a spinal cord stimulation as proposed.

More precisely, with reference to FIG. 5, the method for evaluating the efficacy of spinal cord stimulation 500 can comprise the following steps:
  A2: performing the steps of the mapping method 400 described above.
  B2: performing spinal cord stimulation on the patient with the aid of at least one electrode. In one embodiment, the electrode has been implanted beforehand during a surgical procedure in the area of the painful zone 104 experienced by the patient. In another embodiment, the spinal cord stimulation is carried out during a surgical procedure intended for implanting the electrode.
  C2: displaying a second silhouette substantially identical to the first silhouette 100 on a second screen. The second screen is, for example, a touch-sensitive screen, advantageously a touch-sensitive tablet screen. In a non-limiting embodiment, the second screen is the aforementioned first screen.
  D2: drawing at least one paresthesia zone on the second displayed silhouette, indicating the location of paresthesia experienced by the patient in response to the spinal cord stimulation.
  E2: determining a second number of pixels of the second screen corresponding to the paresthesia zone.
  F2: converting the second number of pixels into a skin surface of paresthesia, the aforementioned reference distance being used as conversion parameter. The conversion is effected in the same way as in step E1 of the mapping method 400. The paresthetic skin surface is then displayed on the second screen, which allows the physician to obtain information.
  G2: comparing the paresthetic skin surface with the painful skin surface determined during step E1 of the mapping method 400.
  H2: superposing the second silhouette and the first silhouette 100 on the second screen or on the first screen 102.
  I2: in one embodiment, the second silhouette, on which the one or more paresthesia zones are drawn, and the paresthetic skin surface are recorded on the server.

It will be noted that in one non-limiting embodiment the second screen is the aforementioned first screen. In one non-limiting embodiment, the second screen is a touch-sensitive screen, and the patient draws the paresthesia zone using his fingers. In one non-limiting embodiment, the second silhouette is substantially identical to the aforementioned first silhouette. Advantageously, the painful surface has been predetermined using the aforementioned mapping method.

By comparing the paresthetic skin surface and the painful skin surface, the physician can determine whether the spinal cord stimulation has been effective in terms of coverage.

The mapping method according to the invention thus makes it possible to determine parameters for quantification of the pain and of its treatment:
  strictly by calculating the painful surface area, and
  indirectly by evaluating the paresthesia surface area and, finally, the pain/paresthesia ratio.

All this is done according to the zones and regions of distribution of the nerve fibers and of their representation in the central nervous system (somatotopy). The two aspects of the invention are noted:

- a diagnostic and therapeutic method (before, during and after surgery) for recording and monitoring the pain experienced by the patient and its evolution, and for providing an indication toward a treatment of choice,
- a method for evaluation of a painful surface using a medical device with a view to evaluating the efficacy of the latter.

Figure 6:
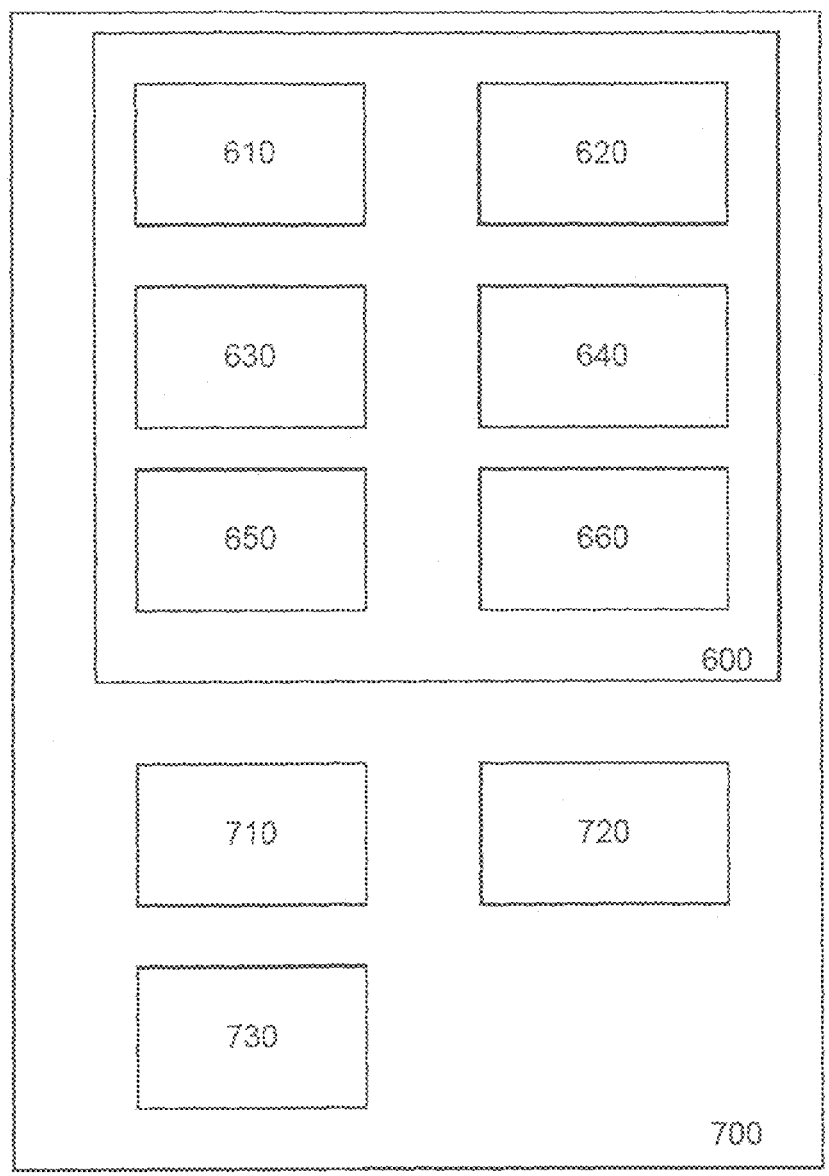
FIG. 6 shows a schematic representation of a mapping system and of a system for evaluating the efficacy of a spinal cord stimulation as proposed.

With reference to FIG. 6, the mapping system 600 comprises:

- means 610 for displaying a silhouette, representing the posterior aspect of a body, on a screen,
- means 620 for drawing at least one zone on said silhouette,
- means 630 for determining a number of pixels of the screen corresponding to said zone,
- means 640 for converting said number of pixels into a skin surface area by means of a reference distance used as a parameter of said conversion.

The following may be added:

- means 650 for determining a ratio of said skin surface area included within a region of the silhouette,
- means 660 for comparing the skin surface area to a second skin surface area determined beforehand,
- means for correcting the skin surface area using a correction criterion.

The mapping system 600 permits implementation of the mapping method 400 according to the invention. The drawn zones can correspond to painful zones or to zones of paresthesia experienced following a spinal cord stimulation.

The system for evaluating the efficacy of a spinal cord stimulation 700 comprises:

- the mapping system 600,
- means 710 of spinal cord stimulation. Classically, this entails at least one multi-contact electrode implanted under the patient's skin and connected to a control box,
- means 720 for comparing a painful skin surface area to a paresthetic skin surface area, said paresthetic surface area being experienced in response to a spinal cord stimulation by the spinal cord stimulation means,
- means 730 for calculating a percentage coverage of the painful skin surface area by the paresthetic skin surface area.

The system for evaluating the efficacy of a spinal cord stimulation 700 permits implementation of the method for evaluating the coverage efficacy of a spinal cord stimulation 500.

The rest of this description concerns preferred embodiments of the systems 600 and 700.

Figure 7:
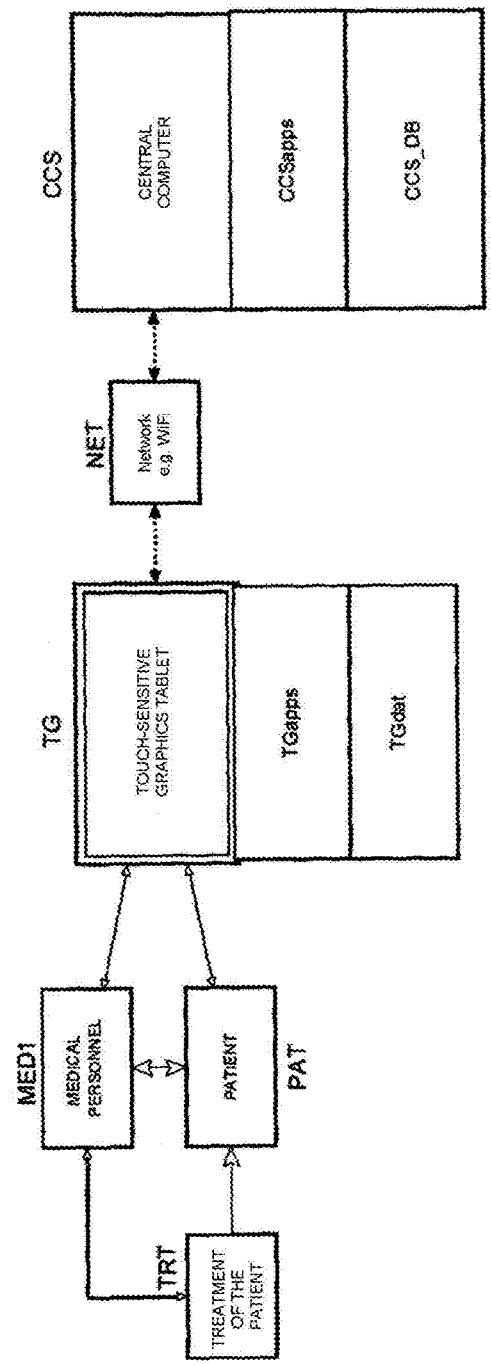
FIG. 7 is a block diagram of the proposed equipment, with their medical context.

In FIG. 7, the reference TG designates a portable touch-sensitive graphics tool, here a high-resolution, touch-sensitive graphics tablet, in which an application memory TGapps and a data memory TGdat are called up.

The graphics tablet TG communicates via a local network NET, for example of the WiFi type, with at least one central computer CCS, for which an application memory CCSapps is called up, and a data memory containing in particular a database CCS_DB.

Here, the central computer is situated in a hospital. It can be shared between several hospitals, in which case the network NET is supplemented by a more extensive network communication structure. Generally, the graphics tablet TG can therefore access the central database CCS_DB in real time via an intranet network or via the internet, directly or by way of other computers.

The context comprises a patient PAT, at least one medical member of staff MED1, and a treatment device TRT for the patient, under the control of the medical personnel.

The treatment device TRT can be a neurostimulation device, which is in contact with the body of the patient and which emits an electrical stimulation acting on the nervous system of the patient (this can, for example, produce a tingling sensation in the patient).

A neurostimulation device comprises an implantable stimulation electrode, generally with several contacts, mounted in a defined geometric configuration, with optional extensions connecting the electrode to the following element, if necessary, and an implantable electrical generator situated, for example, under the skin of the abdomen or under the buttocks, often equipped with a remote control with which it is possible to selectively control which contacts are electrically powered and also the stimulation parameters. This selective control defines a working configuration of the neurostimulation device.

The words "electrode" and "lead" are used synonymously in English. The word "neurostimulator" is sometimes used in practice to designate the electrical generator alone, since it regulates the working configuration of the neurostimulation device.

In the present description, the words "electrode", "neurostimulation device", "neurostimulator" or more briefly "stimulator" are used as synonyms to designate the overall neurostimulation device. When the word "electrode" or "lead" is used, it is understood that the rest of a neurostimulation device is connected to it.

The functions 610, 620, 630, 640, 650 and 660 in FIG. 6 can be used, at least in part (including for each function), by the applications CCSapps. Complex calculating functions can be delegated to the central computer CCS (or one of them) depending on the respective calculating powers of the graphics tablet TG and of the central computer CCS. The treatment device TRT can correspond to the spinal cord stimulation means 710 of FIG. 6 or to other modes of treatment. The comparison functions 720 comparing a painful skin surface to a paresthetic skin surface, and the functions 730 for calculating a percentage coverage of the painful skin surface by the paresthetic skin surface, can be implemented in the tablet TG, in the computer CCS, or shared between these, again depending on the respective calculating powers.

As is shown in FIG. 7, the medical staff member MED1 and the patient PAT will interact with the graphics tablet TG. For this purpose, in the graphics tablet TG, the applications TGapps can be made available by means of a tree-structured menu with tabs. This menu can be seen as a control application TGappmain available to the medical staff member MED1.

Figure 8:
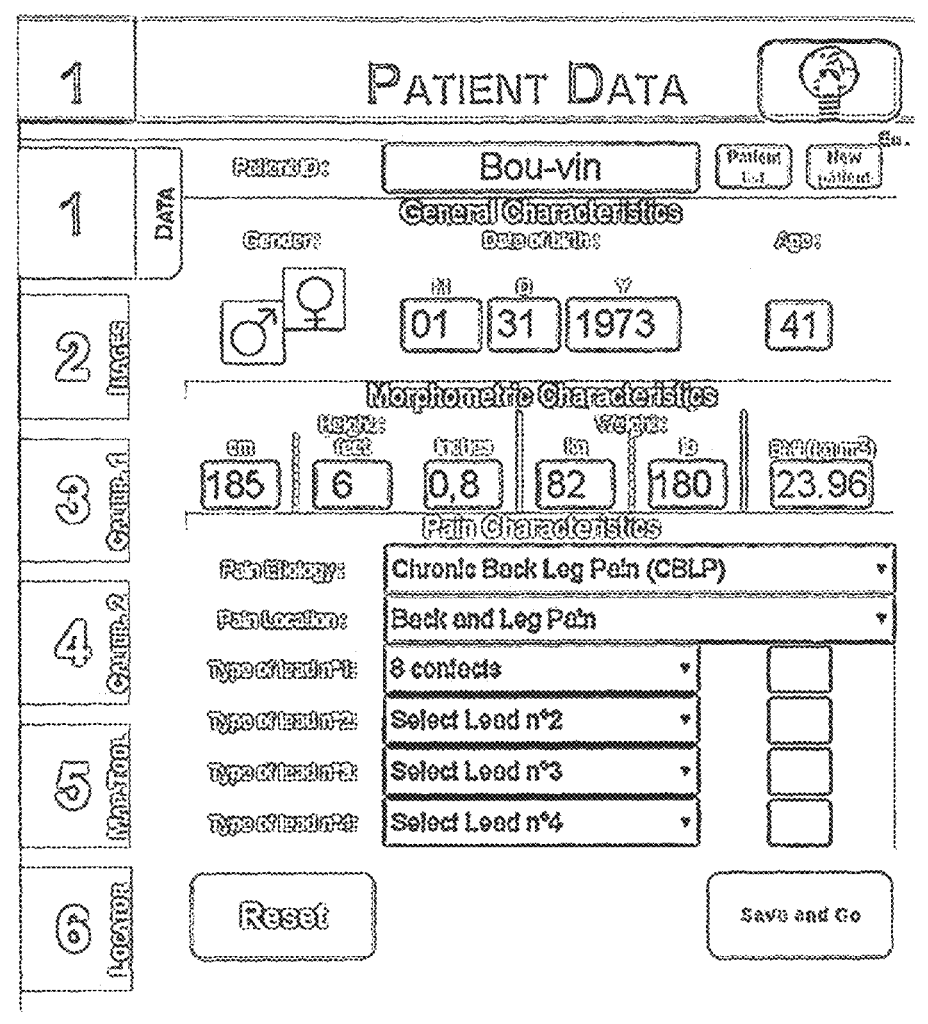

Thus, in the vertical panel on the left of FIG. 8 (and FIG. 8a), six tabs appear numbered 1 to 6.

The interaction takes place in several phases.

A first application TG_app1 allows a patent file to be entered. The entry is made by the medical staff member, if need be by questioning the patient.

A list of patient data is kept in a central database such as CCS_DB. In a known manner, this list of patient data (or patient file) is designed to comply with the applicable confidentiality safeguards, especially when it is accessed. It is managed by an application CCSapp0 stored in the central computer CCS, which can interact with the tablet, and in particular the application TG_app1 thereof.

The application TG_app1 makes it possible to "create" a patient file and to add to the data relating to a patient in an already existing file. This can be done in direct association with the patient file existing in the central database CCS_DB, or by storing one or more patient files in the memory TGdat of the graphics tablet TG, the central database CCS_DB then being updated.

To make matters clear, several sections in a patient file will be distinguished, it being possible for each of these sections to have several subsections.

Section S1—Data Relating to the Patient

The patient file first of all comprises a first, general section S1. It will be described with reference to the screenshot in FIG. 8 (and FIG. 8a). This is shown in English, the customary working language of scientists and computer analysts.

For this section S1, the tab in use is tab 1, which corresponds to the patient data of section 1. These are found to the right of the panel in FIG. 8 (and FIG. 8a).

The first subsection S11 of this section S1 contains general characteristics of the patient, which may be those of Table TS11a below.

TABLE TS11a

| Name | Access |
|---|---|
| Patient ID | Entered |
| Gender | Entered |
| Date of birth | Entered |
| Age | Calculated |

The first subsection S11 also contains morphometric characteristics of the patient, such as those of Table TS11b below. The morphometric characteristics correspond to an anatomical description of the patient comprising at least one anatomical reference parameter. In the present embodiment, this reference parameter is the distance between the iliac crests.

TABLE TS11b

| Name | Access |
|---|---|
| Height | Entered |
| Weight | Entered |
| BMI | Calculated |
| Distance between iliac crests | Entered |

The right-hand column in Tables TS11a and TS11b indicates whether the value in question is entered or else calculated on the basis of values already entered.

The second subsection S12 concerns the etiology of the patient at his first visit (first visit with his problems or with ongoing symptoms of pain). The etiology can be designated from a list of possibilities, for example those of Table TS12 below.

TABLE TS12

Cluster Headache
Arnold Neuralgia
Chronic Migraine
Chronic Back Pain
Chronic Back and Leg Pain (CBLP)
Failed Back Surgery Syndrome (FBSS)
Complex Regional Pain Syndrome (CRPS)

TABLE TS12-continued

Peripheral Vascular Disease (PVD)
Phantom Limb Pain

A third subsection S13 concerns the general and actual location of the pain from a list of possibilities, for example those indicated in Table TS13 below.

TABLE TS13

Headache
Axial Pain
Back and Leg Pain
Lower Extremity(ies)
Upper Extremity(ies)

This is illustrated in FIG. 8 (and FIG. 8a) under the heading "Pain characteristics".

In FIG. 8 (and FIG. 8a), the etiology is first of all entered, here "Failed Back Surgery Syndrome (FBSS)" (subsection S12 and Table TS12 above), then the general pain sensation, here "Back and Leg Pain" (subsection S13 and Table TS13 above).

A fourth subsection S14 can be provided which describes, if appropriate, the one or more neurostimulators ("Type of lead") that are already implanted or are to be implanted in the patient, for example by noting each time the usual name of the neurostimulator, and also attributes of the implant, such as those indicated in Table TS14 below.

TS14

Monocolumn Percutaneous lead
Monocolumn Surgical lead
Monocolumn subcutaneous lead
Multicolumn surgical lead FIG. 8 (and FIG. 8a) finally names up to four implanted neurostimulators: "Type of lead No. 1" to "Type of lead No. 4", which are not completed here since the patient has not yet received an implant. If the patient has already received an implant, each zone "Type of lead" can be completed according to subsection S14 and Table T14.

Section S2—Data Relating to the Mapping Support Image

The entry of a patient file continues with imaging data, which define the type of image on which the patient will be asked to draw his painful zone (in particular).

Thus, the second section S2 of the patient file will comprise a subsection S21, which defines the first choice of the representation on which the patient will draw, for example as indicated in Table TS21.

TS21

| Choice | Name |
|---|---|
| S21-a | 2D Schematic view |
| S21-b | 2D Selected view |
| S21-c | 2D Real view |
| S21-d | 3D Real view |

Further details concerning the choice S21-a to S21-d are described below:

S21-a: The two-dimensional schematic representation called "2D Schematic view" corresponds to a classical template taking account only of the gender of the individual and related to the height of the individual;

S21-b: The two-dimensional selected representation called "2D Selected view" is chosen from a collection of standard body representations incorporating the gender and height of the individual and related to the BMI of the individual;

S21-c: The photographic representation called "2D Real view" is a representation that has been drawn from a photo of the patient taken in real time and that has been treated by a process of readjustment and digital conversion (cf. below); and S21-d: The three-dimensional representation called "3D Real view" can originate, for example, from a reconstruction based on a medically certified three-dimensional acquisition, at the real scale of the patient.

Figure 9:
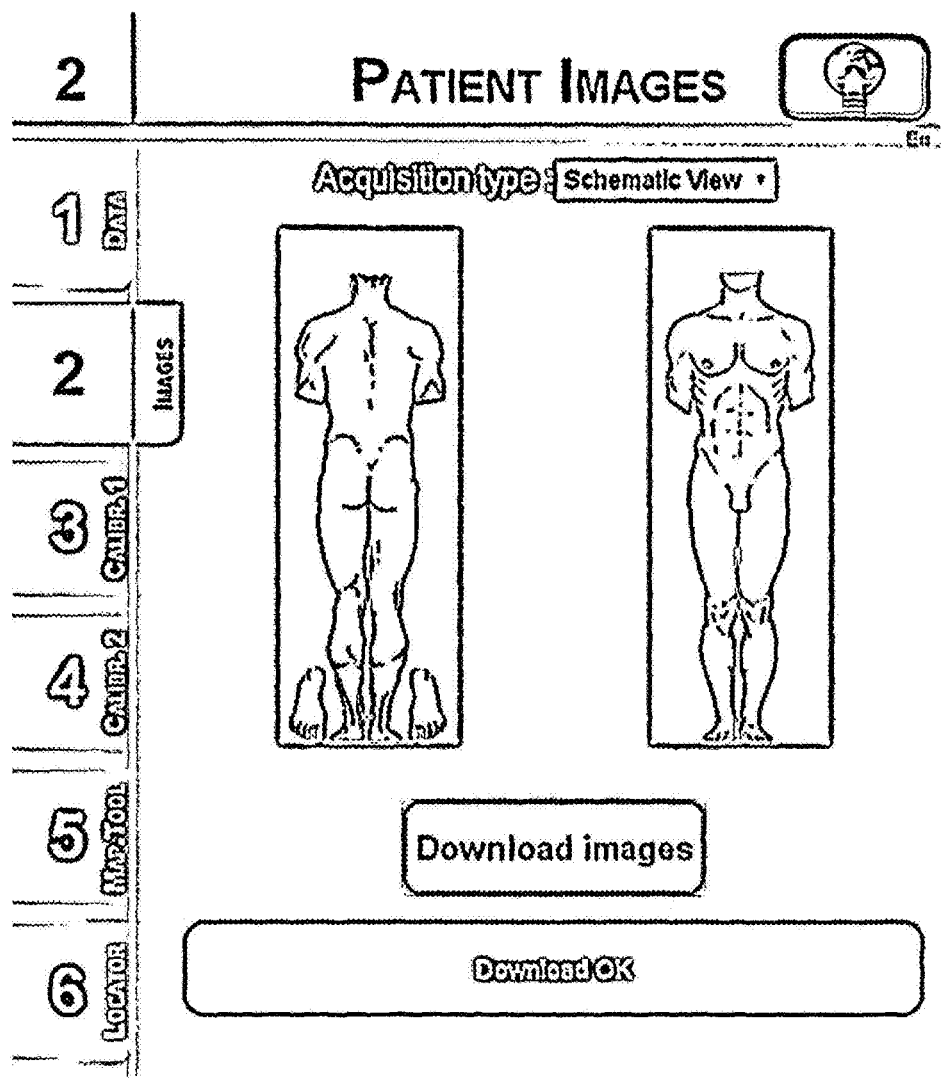
FIG. 9 is a screenshot illustrating a menu for defining the image used to represent the patient.
Figure 9A:
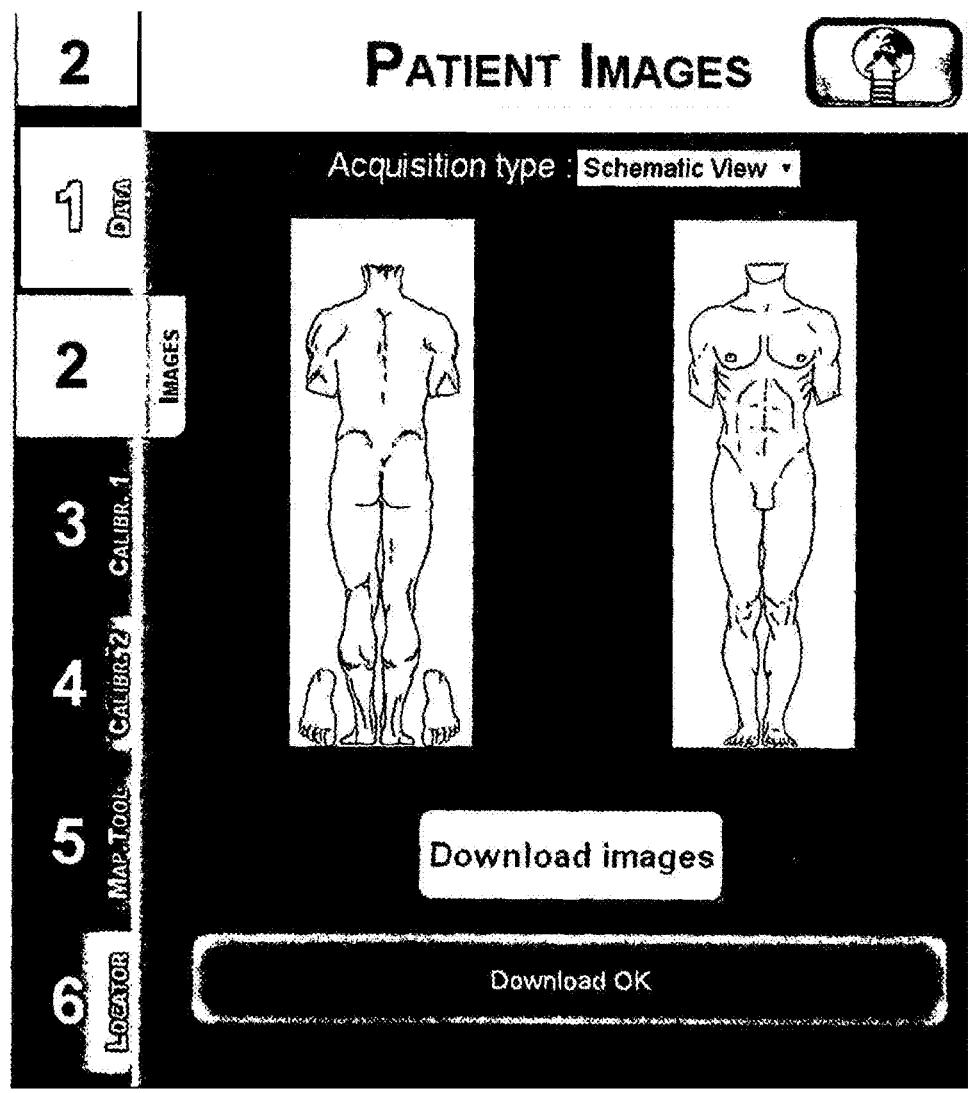
FIG. 9a is the original of FIG. 9 in color.

In FIG. 9 (and FIG. 9a), the tab 2 is activated. The choice is made in the options box "Acquisition type". The buttons "Back" and "Front" permit a choice between a posterior view and an anterior view.

For the choices S21-a and S21-b, two auxiliary subsections S22 make it possible to interrogate the central database CCS_DB, in order to download a silhouette from a set of predefined standard silhouettes, in particular in order to distinguish a female silhouette from a male silhouette (S21-a and b). The choice S21-b offers more precision, since it is possible in particular to take account of the build of the patient, by choosing a silhouette that is pre-calibrated as a function of the body mass index of the patient.

The choice S21-c, comprising a real two-dimensional silhouette of the patient, can be a posterior view, an anterior view, or both. For example, it involves a photo of the patient that already exists in the database CCS_DB. In this case, the photo can be a photo of predefined resolution or can be a photo taken in accordance with the quality defined by a medical standard (in particular the DICOM standard), or else a photo that has undergone readjustment and specific conversion and is integrated in software.

Furthermore, for the choice S21-c, a photograph can be taken during the current visit, for example using a camera integrated in the graphics tablet TG. The photograph can be taken at a predefined resolution and at a predefined distance. The photograph can also be taken with a first resolution at a given distance and can then be recalibrated to a second predefined resolution.

For the choice S21-d, a 3D silhouette can be drawn from a set of pre-existing images which have been obtained, for example, by tomodensitometry, also called computer tomography (CT), or by magnetic resonance imaging (MRI).

The portrait of the pain on a 3D map is possible especially if CT or MRI images of the patient are available. As will be seen, it is possible for such images to be transformed into a 3D silhouette related to a real metric, with which it becomes possible to establish a three-dimensional map of the pain.

It is assumed that a portrait of the pain was already available on a 2D map for a given patient. If one came to have a CT or MRI image of the patient during treatment, it would be conceivable to obtain a 3D silhouette in a real metric and to recover the surface areas of the previous 2D map, since the latter is also in a real metric, while carrying out the appropriate 2D/3D readjustments.

The 3D map allows the following in particular to be taken into account:
hollows and elevations on the body, hence the surface area;
pains of the type involving circular radiation;
surface areas estimated on cylindrical parts, especially limbs;
a minimal unit in $cm^2$ expressed by the so-called triangle technique (much more precise than the technique using square-shaped pixels).

The 3D map makes it possible to locate a pain and to record its development in three dimensions. The 3D map thus makes it possible to determine the exact site (including the subcutaneous depth) of a pain, to monitor its development over time and to observe more precisely, where appropriate, a migration of the pain to another site.

Like the 2D map, the 3D map makes it possible to carry out descriptive studies taking account of different types of spatial segmentations.

The various operations for the acquisition of the pain data are analogous to what will be described below for the 2D mapping (with reference to FIGS. 9 to 17).

However, when the patient "paints" or portrays his pain or his paresthesia on a 3D silhouette, the part of the 2D surface of the screen which is the site of the tactile impact is projected onto the 3D silhouette once the patient's finger leaves the screen. This projection can be seen as a "jet or spray of paint", starting from the painted zone of the 2D screen and directed onto the 3D silhouette. In summary, the pain portrait takes account of the real and three-dimensional body shape of the patient.

The 3D silhouette is modeled, for example, in the form of contiguous triangles. The "painting", on the 3D silhouette, of the painful or paresthetic surfaces is thus possible instantaneously and homogeneously. Small contiguous triangles on the three-dimensional skin of the 3D silhouette are "painted" or filled, at the same time as square pixels on the 2D screen. If the spray of paint resulting from the tactile impact on the screen is off-camera with respect to the 3D silhouette, it is ultimately without effect on the body.

The duration of application of the finger on the screen and the number of passages of iterative sprays at the same anatomical site do not modify the delimitation of the surfaces, which will only once take into account the colored skin surface.

The surface calculation can be carried out on the basis of the 3D representation by small triangles (or others). The same applies to the calculation of the standard deviation.

The 3D mapping is more exact in the estimation of non-plane surfaces, such as the curvilinear surfaces of the trunk and limbs, and also the reliefs associated with the crevices.

The 3D mapping is also appropriate to the "spiraling" distribution of some dermatomes, such as those of the limbs. For example, the pathway of sciatica resulting from compression of nerve root L5 corresponds to the posterior aspect of the buttocks, the lateral aspect of the thigh, the anterolateral aspect of the calf, the upper aspect of the instep, and the big toe. In 2D mapping mode, there is a risk of taking into account the same surface straddling between the anterior view and the posterior view of the silhouette. At worst, it would be counted twice in the surface area calculation or, conversely, underestimated, since its surface when "flat", i.e. in 2D, does not correspond to its surface area in reality (other example intercostal neuralgia, in a band from the spinal column to the anterior aspect of the chest).

Finally, 3D mapping allows the notion of depth to be taken into account. Pain is a cutaneous projection, since it is the skin that contains most of the nociceptor nerves. However, some forms of dull or deep pain correspond to deeper pain stimuli or conflicts originating from the joint capsules, the intervertebral disks, for example, and their pain projection is much more difficult to assess. The 3D mapping makes it easier to take account of the depth of the pain, by drawing a dull pain and/or deep pain in a different way, with one or more indications relating to depths.

This is applicable to the case of "transfixing" pain. The 3D mapping allows the superficial/deep pain components to be broken down (or "decoupled"). This can be likened to the qualitative assessment of pain described by the patient ("vice-like pain, feeling of tightness, crushing pain, transfixing stabbing pain").

Likewise, during treatment, at the paresthetic level, it becomes possible to distinguish between a superficial coverage due to a subcutaneous stimulation, a few millimeters from the hypodermis, and certain deep sensations resulting from a central stimulation (for example spinal cord stimulation) or from a combined hybrid stimulation, generating a much deeper, diffuse, global and "enveloping" sensation according to the description by the patients, probably because it then concerns central and peripheral fibers, less specific regions, and a greater variety of sensitive fibers.

The 3D mapping capture thus makes it possible for the pain felt by a patient to be represented metrically on the screen of the graphics tablet TG and, in the same way as for the 2D mapping tool, the intensities and the typology of the pains, according to the same color code and the same calculating methods. This makes it possible to quantify the pain felt by a patient, to perform calculations in a metric system (statistical calculations for example) and to monitor the evolution or, where appropriate, the migration of the patient's pain.

All of the data collected can be exported to the database CCS_DB of the neuro-computer server in order to perform the calculations. The illustrated screens comprise, at the top and to the right, a button which actuates the exportation of the data to the server.

It will be noted that the 2D or 3D representations and the relevant photos for choices S21-*a* to S21-*d* may undergo a certain number of modifications in order to adapt, if appropriate, their size and shape (modification by the "clipping" function for cutting a photo in order to show only a targeted anatomical part, such as the chest for example).

In the tree-structured menu with tabs, the tab 1 has been described above, which concerns the patient data, and the tab 2, which defines the type of image on which one will work.

The following sections/tabs 3 to 6 involve the intervention of the patient, as will be shown.

Two different calibration operations are provided. They can take place before the patient portrays his pain. These two calibrations are performed when the patient takes up the graphics tablet TG (with the calibration software) for the first time. It is possible that this step can be performed in part at the start of a visit, for example in a consultation room provided for this purpose.

Section S3—Calibration 1

This section S3 concerns the interaction of the patient with the touch-sensitive screen of the graphics tablet TG, studying how the patient draws/paints on the screen.

The classical pointing devices—mouse or stylus—have good precision and appear to be essential for drawing. Conversely, tactile pointing with the finger suffices to actuate a button on the screen but is much less precise for drawing a surface and/or a contour, inside the (2D or 3D) silhouette, the schematic view or the photo displayed on the screen.

However, the studies by the applicant have shown that it was possible to exploit the more intuitive and more practical nature of tactile pointing by the finger while at the same time retaining sufficient precision in terms of positioning and of surface. Typically, a surface area uncertainty of up to 4 $cm^2$ is presently considered acceptable, since it corresponds to the limits of average discrimination of epicritic touch in the dorsal region of the individual human.

Moreover, a zoom mode is offered to the patient in order to precisely delimit certain regions of interest on the limited surface area.

This first calibration, or Calibration 1, has the object of refining the precision of the patient's touch in relation to the resolution and the characteristics of the screen (actual man-machine interface parameter, with a corrective factor applied instantaneously for the subsequent entries).

The application "appCalib1" displays several points on the touch-sensitive screen of the graphics tablet TG. In one example, six points are displayed successively on the screen at predefined locations on X and Y in the displayed system of coordinates: four points near (inside) the four corners of the screen, one point at the center of the screen, and one point placed at random on the screen. These "target" points are represented, for example, by a circled cross. For each point, a desired position $X_0$, $Y_0$ corresponding to the center of the cross is attached.

For each point, the patient must touch as precisely as possible the center of the target displayed on the screen, using his best intuition. The application "appCalib1" registers the coordinates ($X_1$, $Y_1$) of the pixel at the center of the impact of the patient's finger on the touch-sensitive screen. This step is performed for the six points of the calibration process.

For each point, the application "appCalib1" calculates the following deviations:

$$\Delta X = X_0 - X_1 \text{ and } \Delta Y = Y_0 - Y_1$$

between the desired position of the target point and the position of the pixel at the center of the tactile impact (touched by the patient). The mean and the standard deviation of $\Delta X$ and $\Delta Y$ are calculated.

The application appCalib1 then defines a first series of corrective parameters in X and Y, designated Dcal1*x* and Dcal1*y*, which will subsequently be applied to the tactile entries by the patient on the touch-sensitive screen of the graphics tablet TG.

The same correction in X and Y can be applied for the whole screen, in which case Dcal1*x* and Dcal1*y* are constants.

Alternatively, especially if the deviations are not the same at the corners and at the center, it is possible to use a pair of corrections in X and Y for each of the points tested. In this case, Dcal1*x* and Dcal1*y* are functions of X and of Y. Thereafter, when the patient touches a zone of the screen, it will be possible to calculate corrections in X and Y interpolated according to the situation of this point with respect to the four corners and to the center.

The random point makes it possible in particular to verify the consistency of the behavior of the patient when he points to the screen.

Figure 10:
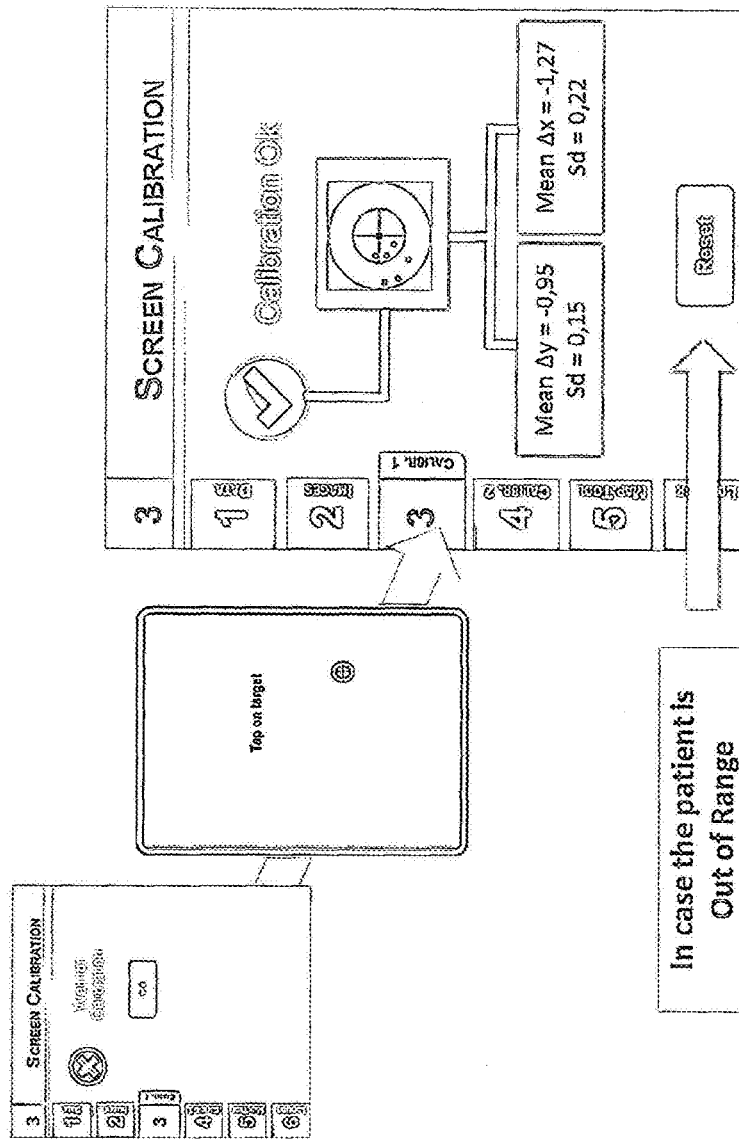
FIG. 10 is a screenshot illustrating the result of the operation called "Calibration 1" below.
Figure 10A:
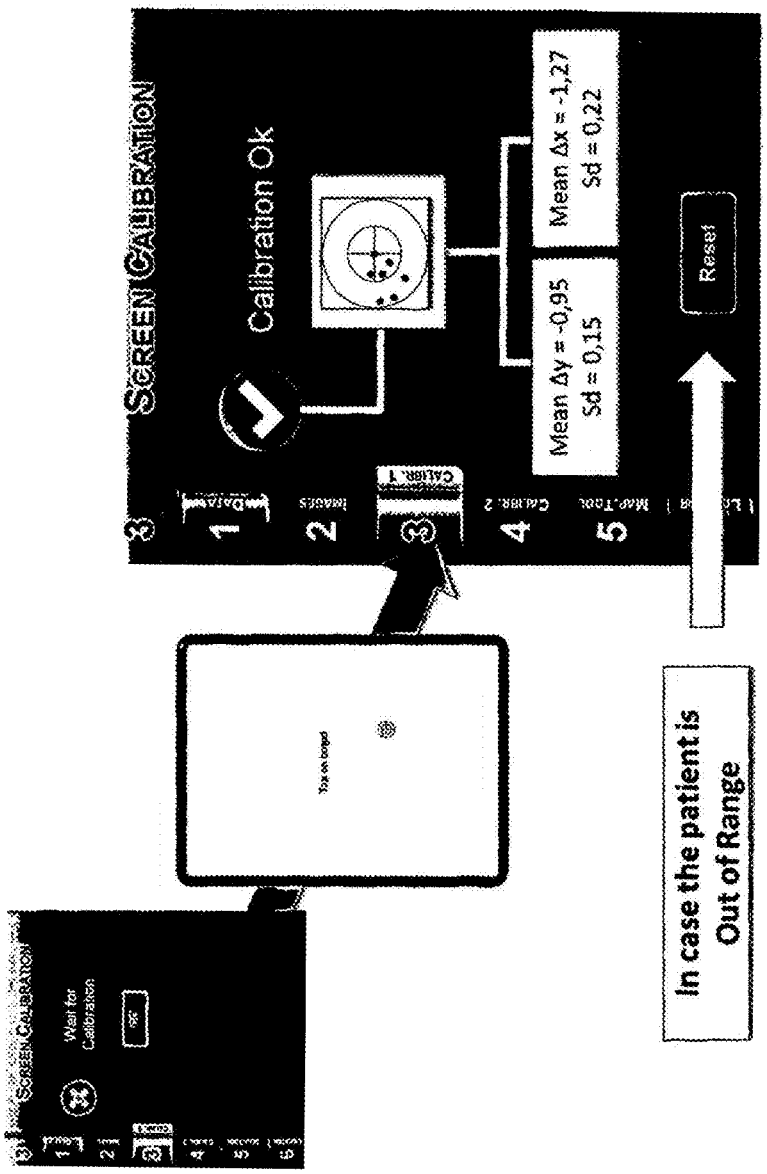
FIG. 10a is the original of FIG. 10 in color.

A particular embodiment is illustrated in FIG. 10.

The initial screen is on the left in FIG. 10. Then, at the center, the patient is invited to touch the target (Tap on target). When this has been done for the 6 points, the distribution of the touches is displayed on the screen shown on the right in FIG. 10. The mean deviations in X "Mean Δx" and in Y "Mean ΔY" and their respective standard deviations "Sd" are then displayed.

Section S4: Calibration 2

This second calibration is called patient auto-calibration. It concerns the way in which the patient perceives sensations spatially at points or zones of his body, for example where he feels a pain. In other words, its aim is to analyze the patient's ability to "geolocate" a position on his own body.

For example, when this geolocation concerns a point situated on the patient's back, the patient has to operate blind. The ability to geolocate points under blind conditions is a very difficult exercise. Thus, the auto-calibration operation of the present invention affords the possibility of better mastering this.

The problem is the following. Pain located at points on the upper back is taken as an example. The applicant has observed that, in most cases, the patient defines the position of this punctiform pain quite well in the vertical direction. By contrast, his spatial sensations are much less clear in the horizontal direction. Similarly, a patient will not systematically describe, with the same precision, the geolocation of a right-side thoracic pain and the geolocation of a left-side lumbar pain.

Generally, the following procedure is observed:

an assistant or "observer" will touch the patient at successive chosen points, or target points, of which the coordinates $X_0(i)$ and $Y_0(i)$ are known from the graphics tablet TG;

on each occasion, the patient will touch the silhouette (a "silhouette" is understood below as a 2D or 3D silhouette, a schematic view or a photo) on the graphics tablet TG, at the point $X_1(i)$ and $Y_1(i)$ where he thinks he felt being touched by the observer.

On each occasion, the tablet determines the deviations between the target point and the point touched by the patient on the silhouette:

$$\Delta X = X_1(i) - X_0(i)$$

$$\Delta Y = Y_1(i) - Y_0(i)$$

where i is the iteration.

"Observer" indicates that this person is not necessarily a physician or nurse. A person qualified in anatomy may supervise this Calibration 2.

This makes it possible in particular to take account of the systematic disparities between the points on the patient's back, as they appear physically, and the points on the patient's back as they are felt by him (and indicated by him on the graphics tablet TG).

The standard deviation of the distribution provides an assessment of the reliability of the patient's ability to locate his physical sensations and, consequently, of the reliability of the representation of said physical sensations as indicated by the patient on the screen of the graphics tablet TG.

The result of this Calibration 2 will thus comprise deviation parameters specific to the individual, with corrective factors applied in the post-processing of the touch data relative to this individual (Calibration 1). Where appropriate, Calibration 2 will exclude patients having too poor a perception of their physical representation, typically if 5 to 6 points touched by the patient are outside the reference target.

More precisely, for this Calibration 2, the corrective parameters Dcal1x and Dcal1y, as defined by the application appCalib1, will be applied to each touch performed by the patient. It should be noted that Calibration 2 would be applied even if the pointing was not tactile and was effected with the aid of a stylus or a mouse, for example, in which case it would be possible to omit Calibration 1.

Figure 8A:
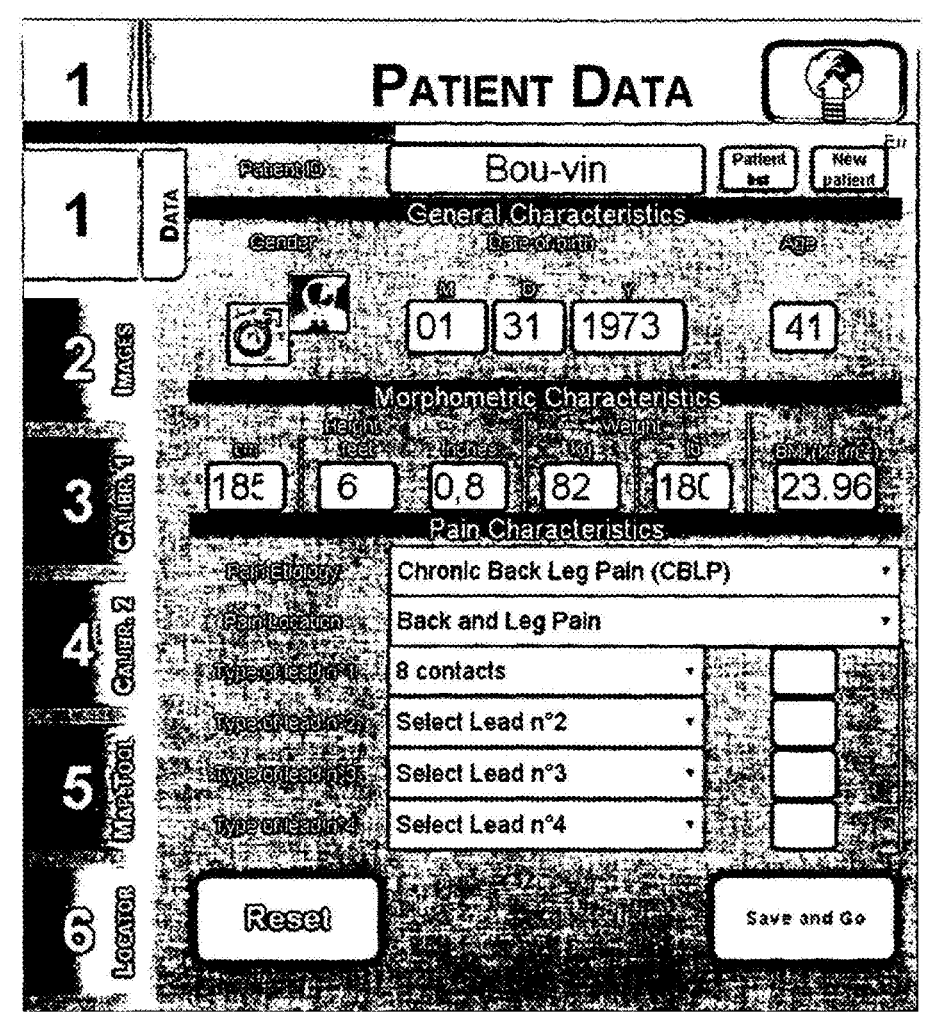

This section S4 corresponds to the tab 4 of the screen in FIG. 8 (and FIG. 8a). When the tab 4 is activated, the start screen illustrated in FIG. 11 (and FIG. 11a) is obtained, for example.

This Calibration 2 can be carried out according to 2 protocols:

a simplified protocol called "Quick calibration",
a protocol optimized by the results from the tests of statistical validation of the software and called "Optimized calibration".

Figure 11:
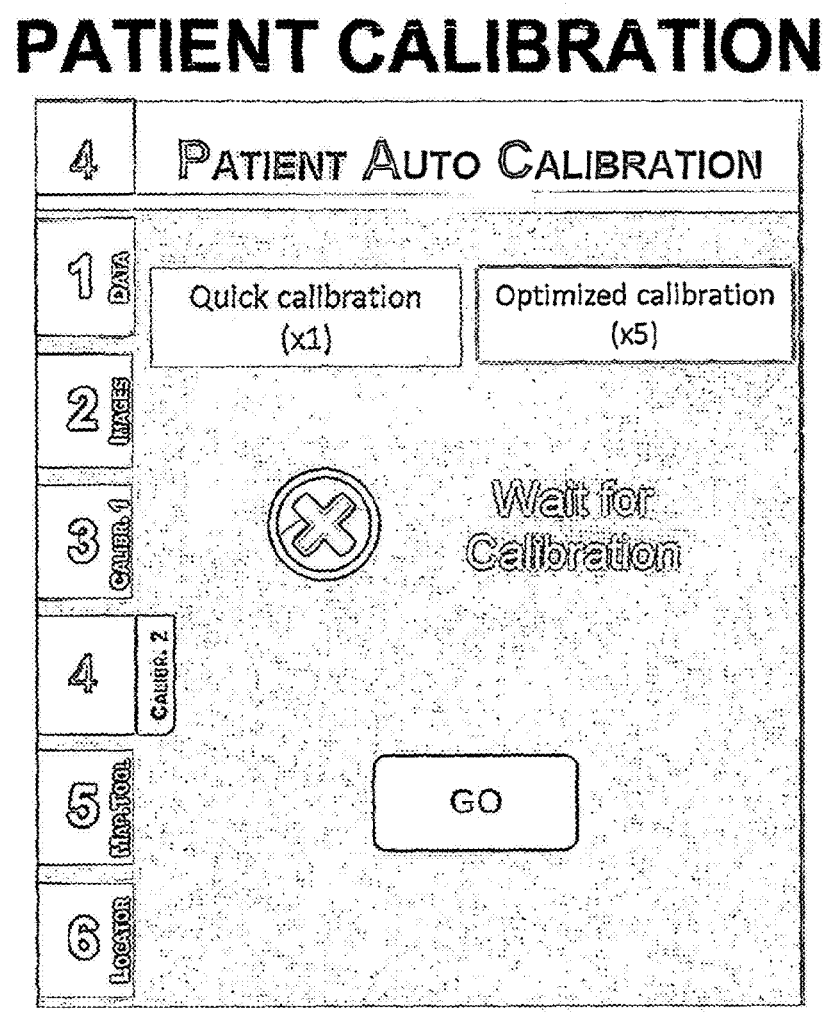
FIG. 11 is a screenshot illustrating the commencement of the operation called "Calibration 2" below.
Figure 11A:
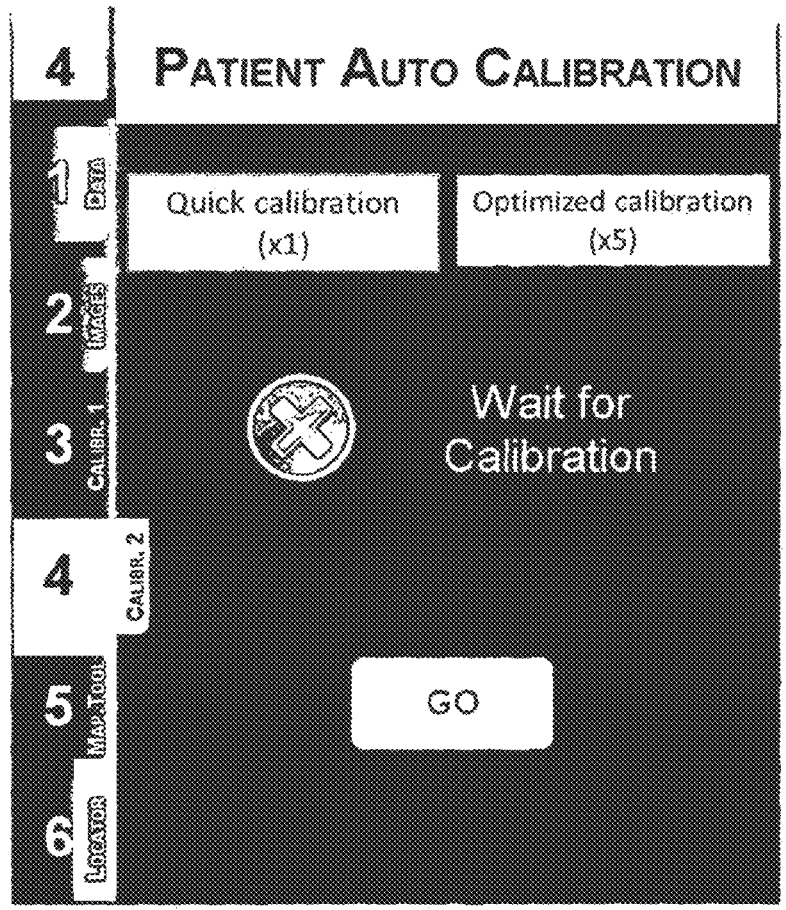
FIG. 11a is the original of FIG. 11 in color.

The choice between the two protocols can be made using a screen like that of FIG. 11 (and FIG. 11a).

Quick Calibration

Six points of the patient's body, which are predefined in the application "appCalib2" and are easily identifiable by standard anatomical references (cf. Table TS41 below), are shown to an observer (on a screen dedicated to the observer) on a schematic view of the patient and are not known by the latter. The word "observer" indicates a person qualified in anatomy, since it is not necessary for this phase to be performed systematically by a physician or a nurse.

The observer will then successively touch the patient's body at these six different points, which are here called calibration targets (cf. Table TS41 below). For each point touched by the observer, the patient will have to designate the target, where he feels the observer's touch, on the silhouette that the application "appCalib2" presents on the screen.

Figure 12:
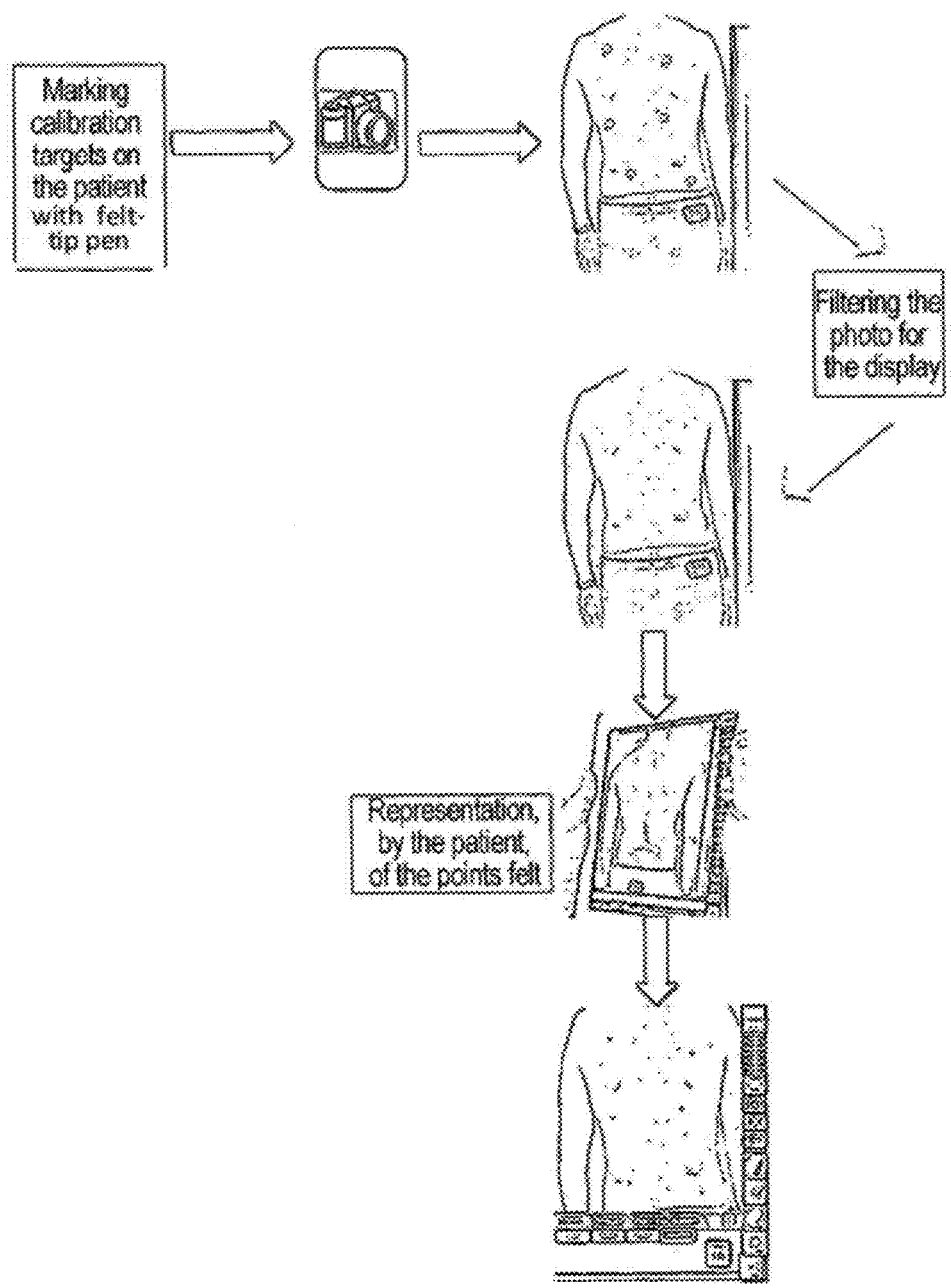
FIG. 12 illustrates a basic embodiment of the operation called "Calibration 2" below.

A variant is illustrated in FIG. 12 (and FIG. 12a). The observer will use a specific felt-tip pen to mark directly, on the patient's body, precise anatomical markers (predefined by the statistical validation protocol) corresponding to the aforementioned "calibration targets".

The observer will then take a photo of the patient, from the back, using the camera available on the graphics tablet TG. The photo can be automatically clipped by the application "appCalib2" so as to retain only a chosen part of the body. Said part of the body can be the part of the body strictly included between the top of the cranial arch (vertex) and the bottom of the patient's heels. In the present embodiment, the part of the body is the part strictly between the top of the cranial arch (vertex) and the gluteal folds.

In a first operation, the coordinates of felt-tip markings on the photo are identified by the graphics tablet TG and registered in its memory. The coordinates can be entered and registered manually by entering the respective X and Y coordinates and then registering them. Alternatively, the registering can be done automatically by photographic recognition of the felt-tip pen markings or else by temporary placement of self-adhesive probes on the patient's back. The present embodiment uses photographic recognition of the felt-tip pen markings.

In a second operation, the patient indicates, on the photo, the places where he feels the observer's touch for each calibration target. The markings of the calibration targets (and their coordinates) are not visible to the patient during this operation. To this end, the felt-tip pen markings are eliminated on the photo with the aid of a specific filter (for example a color filter) before showing the display to the patient.

Figure 13:
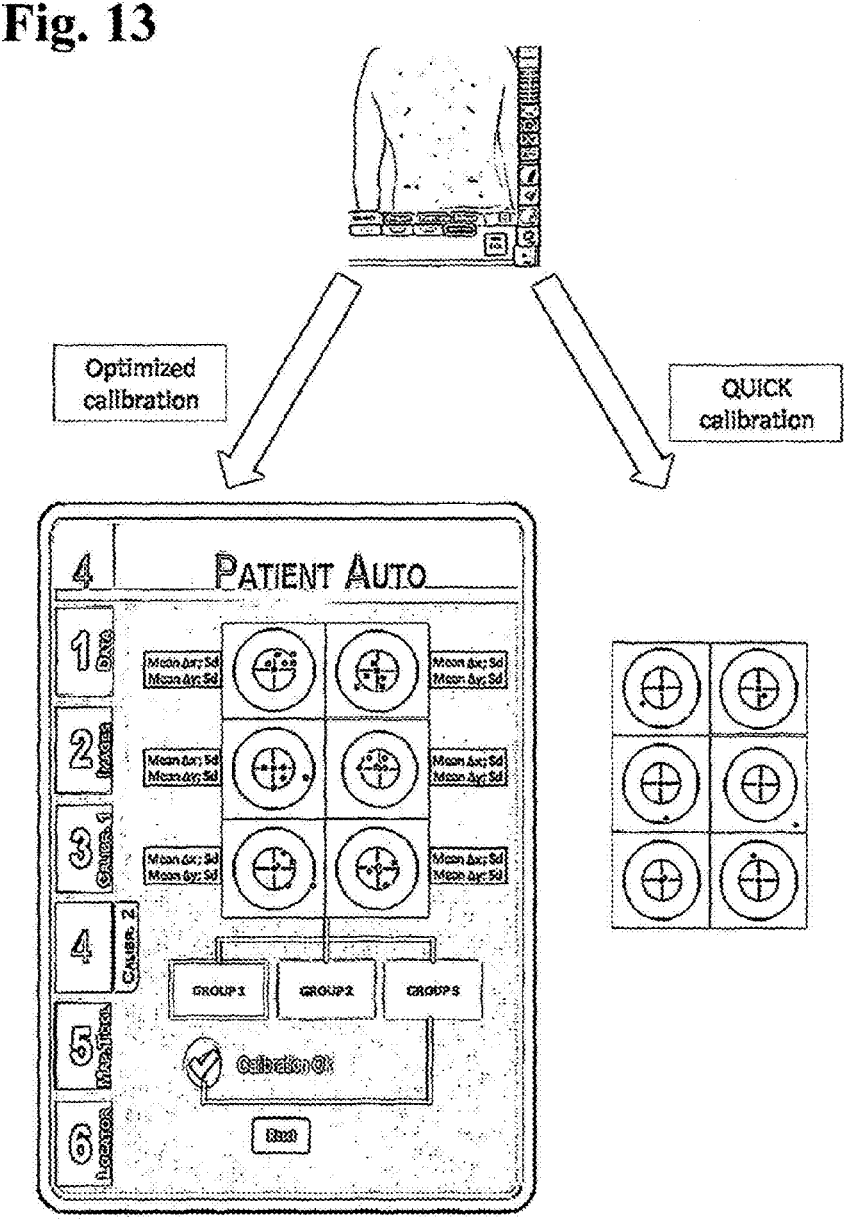
FIG. 13 illustrates two modes of exploiting the operation from FIG. 12.
Figure 13A:
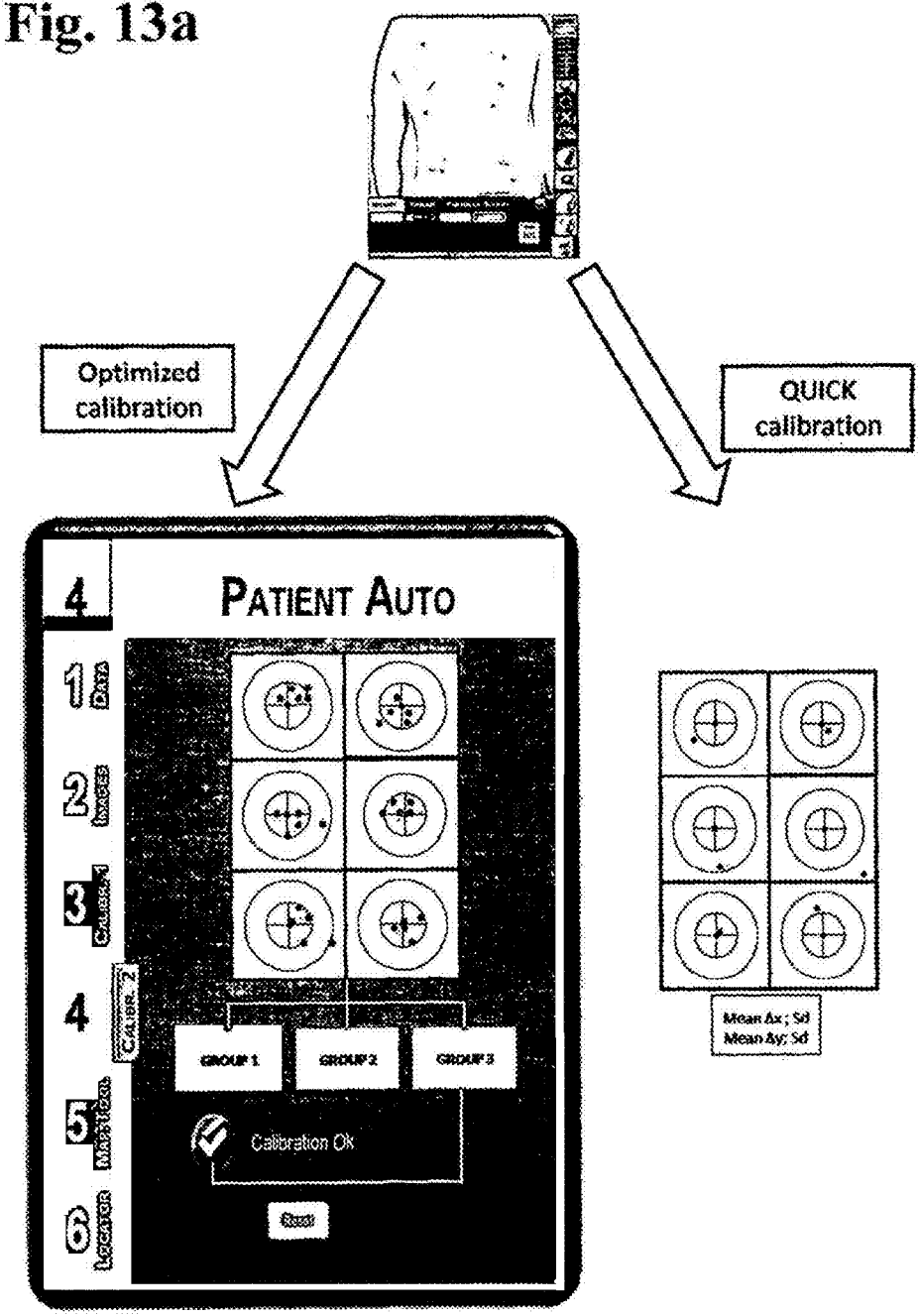
FIG. 13a is the original of FIG. 13 in color.

An example of distribution of the deviations between target points and patient points is illustrated at the bottom right of FIG. 13 (and FIG. 13a).

Optimized Calibration

The optimized calibration is carried out several times, for example on 5 cycles. The order in which the observer has to touch the targets and ask the patient to indicate the precise feel of each target is rendered more or less arbitrary (by a process of randomization). The order that results from this randomization is indicated to the observer, at the start of each cycle or test, on a confidential screen. In this way, it is possible to limit the skew caused by "chronological" learning of the geolocation of the targets.

In one embodiment, the order in which the targets are presented is automatically generated by an algorithm using, as key, data concerning the identity of the patient. This makes it possible to have the same order on two computers with two respective separate screens used simultaneously: one for guiding the observer throughout the test, and the other (the tablet) for taking account of the tactile impacts made by the patient, to proceed with the analysis and then display the deviations and corrective factors to be applied, as a function of the regions.

It is therefore a photo free of any trace of felt-tip pen that will be presented to the patient at each step of the calibration test (FIG. 13 bottom left).

The observer will then successively touch the six different calibration targets on the patient's body, as a function of the randomization order assigned by the application to each predefined target. The patient will have to designate each time on the screen, on his own photo, the point where he feels he has been touched by the observer. This step will be carried out five times.

An example of distribution of the disparities between target points and patient points is illustrated at the bottom left in FIG. 13 (and FIG. 13a).

The optimized calibration procedure requires more time than the quick calibration procedure but permits a more precise estimation of the patient's ability to represent his own physical perception, applied to the back, and thus to attribute reliable corrective factors to the source data, in post-processing and as a function of the dorsolumbar subregions concerned.

Calibration Targets

The calibration targets can be those in Table TS41 below:

TABLE TS41

Right iliac crest
Left iliac crest
Right scapula inferior angle
Left scapula inferior angle
Right gluteal fold center
Left gluteal fold center
3rd lumbar vertebra (L3)
Junction between 7th cervical vertebra (C7) and 1st thoracic vertebra (T1)

In summary, this optimized calibration makes it possible in particular to take account of the disparities between the calibration targets on the patient's back, as they are defined physically (real targets of coordinates $X_0$ and $Y_0$), and the perception of these calibration targets (feel of the coordinated targets $X_1$ and $Y_1$) by the patient, as indicated by him on the graphics tablet TG. Each time the patient touches the screen as precisely as possible, the application "appCalib2" locates the position (X and Y coordinates) of the zone touched by the patient.

Six values of deviations of X and Y coordinates are obtained $\Delta X = X_1(i) - X_0(i)$ $\Delta Y = Y_1(i) - Y_0(i)$ with i ranging from 1 to 6.

This can be represented in the form of 6 test cards, comparing the sites of the pixels located at the center of the "calibration targets" touched by the observer and the sites of the pixels at the center of the tactile impacts corresponding to the positions felt by the patient. This is what is shown at the bottom and on the right of FIG. 13, for the quick calibration.

Statistical considerations can be applied, for example if there are excessive disparities, or if the standard deviation shows that the distribution of the deviations is too remote from a Gaussian distribution. They will allow the application appCalib2 to decide to accept or decline the calibration.

If the calibration is accepted, the application appCalib2 defines a second series of corrective parameters in X and Y, Dcal2$x$ and Dcal2$y$, which will be applied to the entered data, in the post-processing phase. These parameters Dcal2$x$ and Dcal2$y$ will be able to vary as a function of the region of the back (or more generally of his body) in which the patient will enter the source data.

The quick calibration may be sufficient for patients who have good spatial awareness of their body or in order to verify a calibration already made previously.

The optimized or detailed calibration permits a better assessment of whether the patient has good spatial awareness of his body. Proceeding through 1 to 5 cycles, it is possible to obtain information that is richer, at least statistically.

In addition, the inventors have observed that there is a learning effect, which generally allows the patient to be fully operational after 5 training sessions, even if he had never practiced geolocating.

Patients having a significantly impaired representation of their physical makeup, and for whom reliable use of the tool cannot be guaranteed, will be able to be identified and then either excluded from the analysis of the results from the software or analyzed while taking into account their specifics, which do not necessarily exclude them from being able to provide drawings of their sensations of pain and/or paresthesia, for example with the aid of a function of conversion appropriate to such a patient.

For the rest, as a function of the ability of each patient to "geolocate" the points of his body, it will be possible to class patients in several groups, for example 3 groups: "good locator" if fewer than 3 points touched by the patient are outside the reference target, "average locator" if 3 to 4 points touched by the patient are outside the reference target, and "poor locator" if 5 to 6 points touched by the patient are outside the reference target.

The calibration deviations of one or other type can be applied in the tablet and/or during the subsequent processing of the data.

Working in Real Metrics

The actions in section S3 and/or section S4 can also include calculations for using real metrics, that is to say for establishing the equivalent in real size (height and width), in cm, of a pixel on the screen.

If a photo is used, the size in cm of a pixel on the screen can be determined on the basis of adjustments made at the time of taking the photo, and/or on the basis of the height of the patient, if it is a complete photo.

In the case of a 2D schematic silhouette (choice S21-$a$ above), the shapes of the silhouette are approximate, and the pixels of the silhouette are defined in arbitrary units with respect to the real physical dimensions of the patient. It is recommended to convert the size of the pixel into real metrics related to the physical dimensions of the patient. A reference distance can be used for this purpose.

In a simple example, the reference distance corresponds to the distance between the two iliac crests of the patient. This distance in fact varies little from one individual to another depending on build. It is possible to use an estimation of the distance between the iliac crests, if necessary correcting it according to the height and/or weight of the patient. More simply, it is possible to use the physical distance measured between his iliac crests, if this has been entered in the morphological characteristics of the patient (subsection S11 above). The reference distance can be measured beforehand, or else during the mapping.

In another embodiment, the height of the patient (between the base of the heels and the top of the head) can be measured in order to calculate the conversion to real metrics.

The conversion of the arbitrary units of the pixels in $cm^2$ can be done using two calculated coefficients:
- a vertical coefficient equal to the real height of the patient divided by the number of pixels representing the height of the silhouette,
- a horizontal coefficient equal to the distance between the iliac crests of the patient divided by the number of pixels representing the distance between the iliac crests on the silhouette. As the patient has pointed to his iliac crests on the screen, the application appCalib2 knows the distance between the iliac crests in number of pixels, in X (and if necessary in Y).

It will be noted that, even if the pixel is square, its real dimensions (equivalents in cm) in X and in Y are not necessarily the same, in the case of a schematic silhouette which is not to scale.

These two coefficients represent the scale of a pixel in real metrics, for example in centimeters. The product of the horizontal coefficient and of the vertical coefficient gives the surface area of a pixel in square centimeters ($cm^2$).

The real metric of a surface drawn on the screen can then be considered as equal to the product of the surface of a pixel in square centimeters by the number of pixels that the drawn surface comprises.

The same type of treatment can be carried out on all or some of the other locators defined above, such as the distance between the shoulder blades or the distance between the mastoids.

Statistical processing permits an improvement in the precision. It is also possible to use the height and the weight of the patient in order to improve the estimation of the physical distances between two morphological location markers.

In one variant, a collection of schematic silhouettes is used that can be better adapted to the patient over time.

Specific templates can be predefined as a function of the gender and BMI (body mass index) of the patients, for example via a 3D modeling software "Makehuman" (open source, software version CCO). In one embodiment, six models pre-selected for each gender are available for the following BMI intervals: <18, [18-20], [20-22], [22-25], [25-30] and >30. The mapping software automatically adapts the template to be used as a function of the gender, weight and height of the patient as entered in the tab "Data". The template model is chosen as a function of gender and BMI; the size of the template model is adapted to that of the patient by scaling, in order to occupy the entirety of the space dedicated to the image.

The 3D (or 2D) silhouette can be drawn from a pre-existing image of the patient, obtained for example by computer tomography (CT) or by magnetic resonance imaging (MRI). These images are generally recorded according to the DICOM standard (Digital Imaging and Communication in Medicine).

The DICOM file contains image data of the patient and numerous other working data which depend on the imaging mode. The applicant has observed that it is possible to extract the three-dimensional image data from the patient, at the real scale, in order to form a three-dimensional model of the patient.

To this end, it is possible to use software from the family called ImageJ, hinged on Java, and available in Open Source mode from various authors, as indicated in: http://fiji.sc/ImageJ. It is preferable to use the software package Fiji, which contains a version of ImageJ, a spinoff of Java to support it, and numerous software plugins.

In one embodiment, instead of having a single server, the server CCS is broken down into a work server (CCS-T (not shown)), to which the touch-sensitive tablet TG is connected, and a central imaging server (CCS-I (not shown)), which serves as a data bank for an entire hospital establishment.

In this case, the work server CCS-T will obtain the DICOM data for the one or more patients in question from the central imaging server CCS-I. It is also the work server CCS-T which ensures the transformation of images and other calculations, making it possible to reconstruct the physical envelope in 3D, while retaining the real metrics and suppressing information that is not useful (interior of the body, in particular).

The physical envelope in 3D thus reconstructed is a contour defined by juxtaposition of triangular mesh cells, each one of which corresponds to exact real measurements of the body. These same triangles are used to construct the image displayed on the tablet. It is thus known to relate a displayed triangle on the tablet to real measurements and to determine its real surface area, for example by considering that each pixel of the screen projects onto one or more triangles of the 3D image. These calculations can be performed in the work server CCS-T.

The three-dimensional image obtained is stored in the work server CCS-T, which permits access to it by the graphics tablet TG.

Section S5—Tool for Patient Pain Portrait ("NeuroPain'T")

Section S5 will manage the actions in the form of a history, by an application appHisto.

Figure 14:
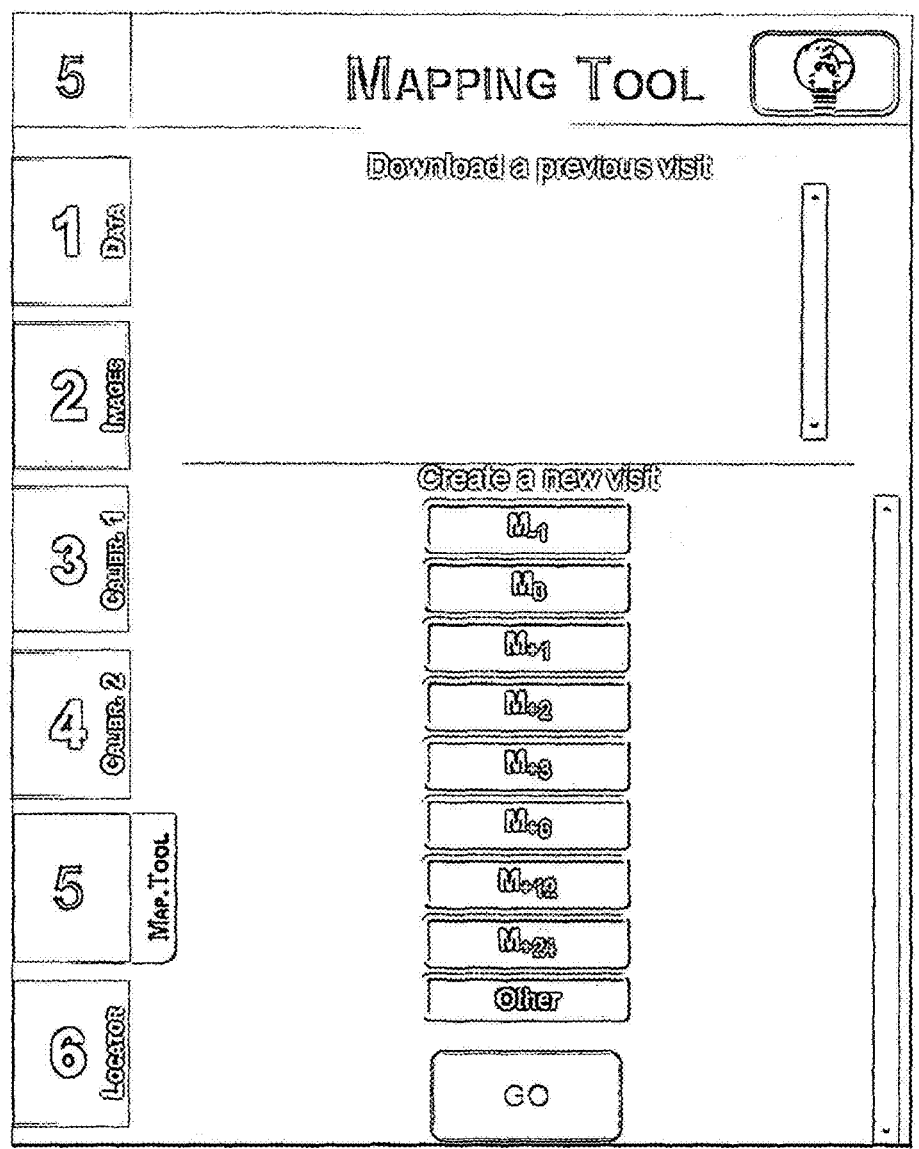
FIG. 14 is a copy of a welcome screen which manages a record.

As can be seen in FIG. 14 (and FIG. 14a), the application appHisto defines an ordered list of patient visits, which are predefined, for example, as:

$M_{-1}, M_0, M_{+1}, M_{+2}, M_{+3}, M_{+6}, M_{+12}, M_{+24}$ where $M_0$ is a reference session, typically a session on the day of implantation of a neurostimulator, $M_{-1}$ is a previous visit, $M_{+1}, M_{+2}, M_{+3}, M_{+6}, M_{+12}, M_{+24}$ are follow-up visits.

The predefined staggering can be in days, where $M_{+1}$ is the session 1 day after the implantation, $M_{+2}$ is the session 2 days after the implantation, etc., and $M_{+24}$ is the session 24 days after the implantation.

The predefined staggering is most often in months, where $M_{+1}$ is the session 1 month after the implantation, $M_{+2}$ is the session 2 months after the implantation, etc., and $M_{+24}$ is the session 24 months after the implantation (with a period of tolerance of ±2 to 5 days).

Other visits may be added to this staggered arrangement. Each visit is associated with a dossier that will contain all or some of the drawings, data, measurements and calculations obtained during this visit.

After selection of a visit (or creation of a new visit), touching a "Go" button allows the launch of the actual map drawings.

By means of these map drawings, the patient will depict or "portray" his pain. He will in fact even "paint" his pain using colors and/or other graphical attributes.

Drawing Functions

The touch-sensitive graphics tablet TG allows the patient and/or the clinician to provide a characterization by drawing a painful zone on the standard schematic two-dimensional representation (S21-a), on one of the pre-calibrated two-dimensional representations (S21-b), on the representation drawn from a photo taken in real time (S21-c), or else on the three-dimensional representation (S21-d). The chosen representation is generically called a silhouette. The silhouette considered here is one taken from the back for dorsal pain.

"Characterization by drawing a painful zone" is understood as the definition given by the patient to the feeling of pain. For this purpose, the patient and the clinician have access to different functions stored in a graphics application appGraph used to precisely describe the pain zone.

Each function can be selected by touching a button/icon on the graphics tablet TG. These functions include in particular:
 a delimitation function for demarcating a pain zone (for example by circling it with a finger on the representation);
 a marker selection function for varying the mode of marking of the pixels (for example a marker can mark adjacent pixels (brush tool) or spaced pixels (spray tool));
 a marker size function for varying the number of pixels per unit of resolution during marking or demarcation (for example the tactile sensitivity can be varied as a function of the size of the finger);
 a coloring function;
 an eraser function for correcting an incorrect manipulation;
 an eraser size variation function, for varying the number of pixels per unit of resolution during a correction;
 a cancellation function for canceling an action and restoring an initial state, for example for correcting an incorrectly marked selection;
 a repetition function for repeating a performed action;
 a reset function for returning to a base state and in this way annulling any action that has been executed.

Each function is generally used separately. However, each result obtained by the tactile manipulation of a given function can be superposed with one or more other results obtained by tactile manipulations effected with another function.

For mapping a patient's pain, the patient is asked to delimit, by touching the tablet, the pain or pains, for example back pain, that he feels on an everyday level. He will even be able to input the sites of the pains iteratively, at different times during a 24-hour period, in order to provide information on the possibly positional nature (dependent on the position of the patient) of the pains and the surface areas thereof.

The proposed mapping makes it possible to evaluate pains, in particular "positional" pains, at different times of the day. When crouching down, the patient may feel mechanical pain in the back, whereas, when lying down, he feels neuropathic pain in the right leg.

As regards the surface areas, it will be appreciated that the abdomen does not have the same surface area when an individual is lying down on his back or leaning forward. Hence, the painful surfaces may be assessed differently depending on the posture of the patient.

To this end, the graphics application appGraph is supplemented by a selection application appSelec which establishes a link between graphical attributes (or "indicators") and descriptions of pains. According to one embodiment, the selection application on the touch-sensitive screen makes available several sets of graphical attributes, which comprise:
 a set of graphical attributes relating to the intensity of the pain;
 a set of graphical attributes relating to the type of pain; and
 a set of graphical attributes relating to a zone for analgesic therapy, such as the implantation of spinal cord stimulation (hence, if appropriate, paresthesias).

A graphical attribute is understood in particular as a color and/or a texture, which includes hatching. In the rest of the present description, reference is made to an embodiment using different colors to characterize the pains. For reasons of form, the colors can be represented on drawings by stippling, hatching or other distinctive graphical signs. The colors indicated in the tables below are given as examples.

Figure 15:
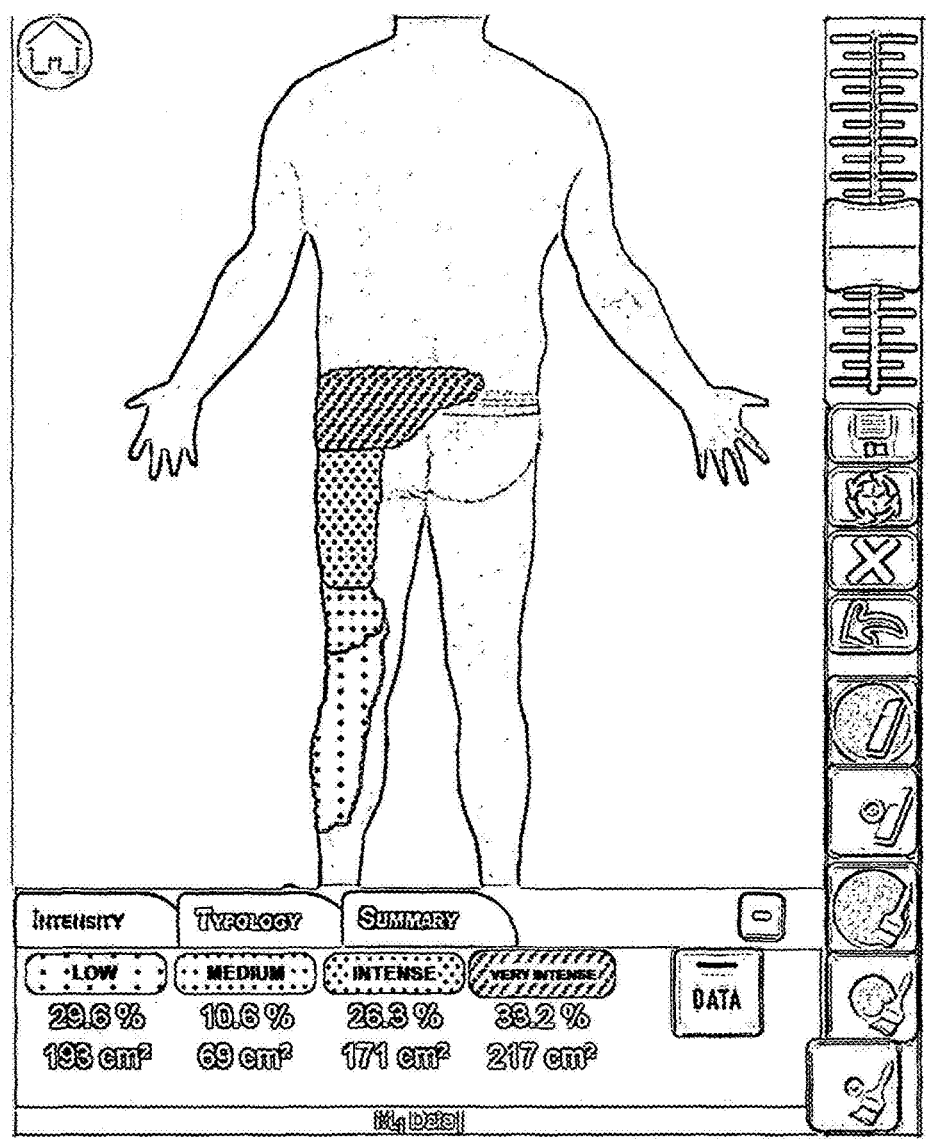
FIG. 15 is a screenshot illustrating an example of mapping the intensity of pain.
Figure 15A:
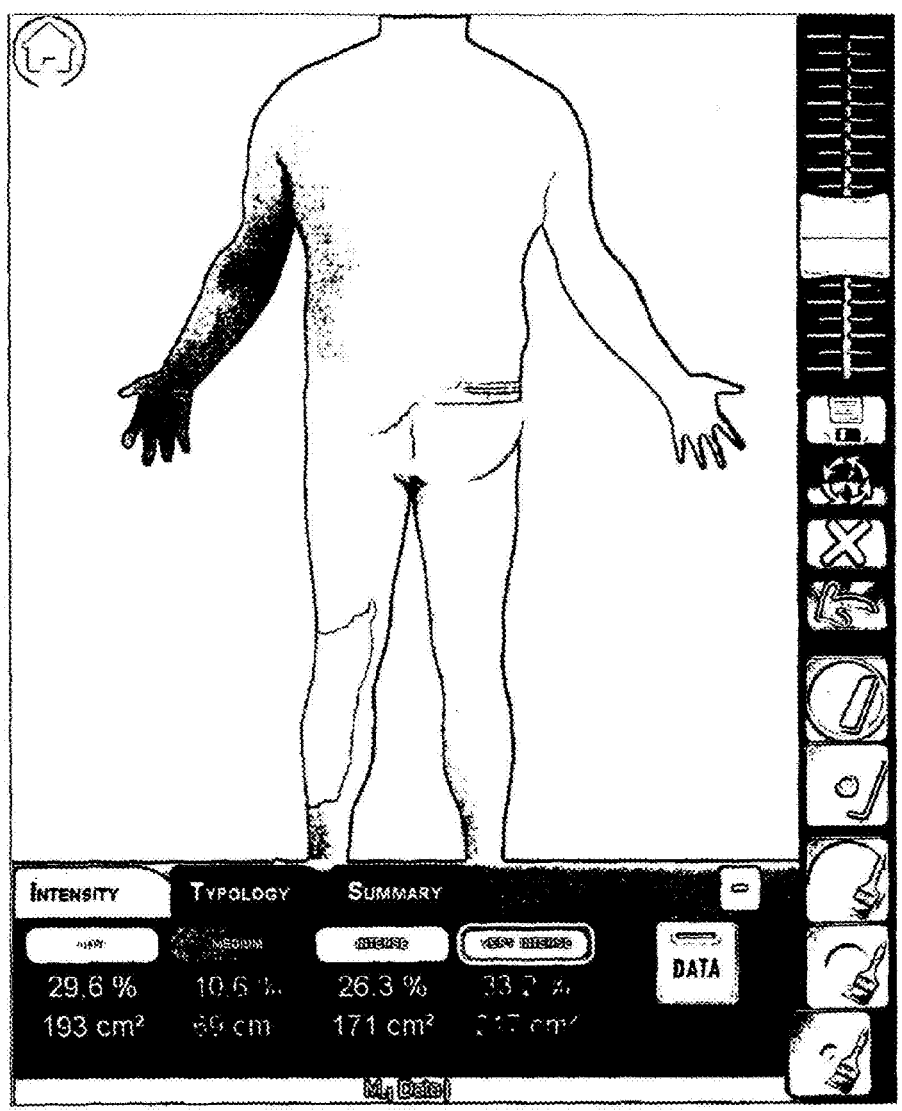
FIG. 15a is the original of FIG. 15 in color.

Reference is now made to FIG. 15 (and to FIG. 15a). On the right of FIG. 15 (and of FIG. 15a), a column is shown comprising graphics functions of the application appGraph represented by pictograms, from top to bottom:
 zoom;
 save/record;
 rotation of the trunk through 180° to move from a front view to a rear view, and vice versa;
 clear all the pain information that has been entered (global reset);
 go back a step (undo);
 wide eraser;
 fine eraser;
 wide brush;
 fine brush;
 very fine brush.

FIG. 15 (and FIG. 15a) comprises a horizontal panel at the bottom. Its upper part has three of the four tabs: "Intensity", "Typology", "Paresthesia" and "Summary", which are part of the application appSelec. Here, the "Paresthesia" tab is not activated, invisible or suppressed, as will be seen below.

Finally, it will be noted that, in FIG. 15 (and FIG. 15a), it is the "Intensity" tab that is activated.

Pain Intensity

The intensity of the pain can be defined on the screen by buttons that are each labeled by its color and by text indicating a pain level. The example of FIG. 15 (and FIG. 15a) uses four pain levels (DL1 to DL4) associated with four different colors, according to Table TS51 below.

TABLE TS51

| | Pain level | |
|---|---|---|
| Level | Name | Color |
| DL1 | Low | Light blue |
| DL2 | Medium | Medium blue |
| DL3 | Intense | Orange |
| DL4 | Very intense | Red |

In FIG. 15, the low pain level LOW is represented by an area of dots spaced apart by a distance D; the medium pain level MED is represented by an area of dots spaced apart by a distance d (where d<D); the intense pain level INT is represented by an area of dots spaced apart by a distance L (where L<d); and the very intense pain level V.INT is represented by an area of dots spaced apart by a distance I (where I<L).

In FIG. 15a, the low pain level LOW is represented by an area colored light blue; the medium pain level MED is represented by an area colored medium blue; the intense pain level INT is represented by an area colored orange; and the very intense pain level V.INT is represented by an area colored red.

To each pain level it is possible to assign the corresponding calculated surface area, and also a percentage of this calculated surface area with respect to the total painful surface area. These variables are calculated in real time. This is illustrated at the bottom of FIG. 15 (and FIG. 15a) in corresponding dots (or in corresponding color for FIG. 15a). The "Data" button allows the observer to choose to display them or not to display them, so as not to influence the patient during the data entry.

For the clarity of the present description, the pain level is indicated near the silhouette, opposite each dotted/colored area.

The drawing commands are constrained by rules, such as:
the drawn surface cannot go beyond the silhouette,
the pain levels are exclusive,
the last pain level drawn prevails.

Optional rules can be added to these, such as: the eraser only removes the color/texture in progress.

Figure 16:
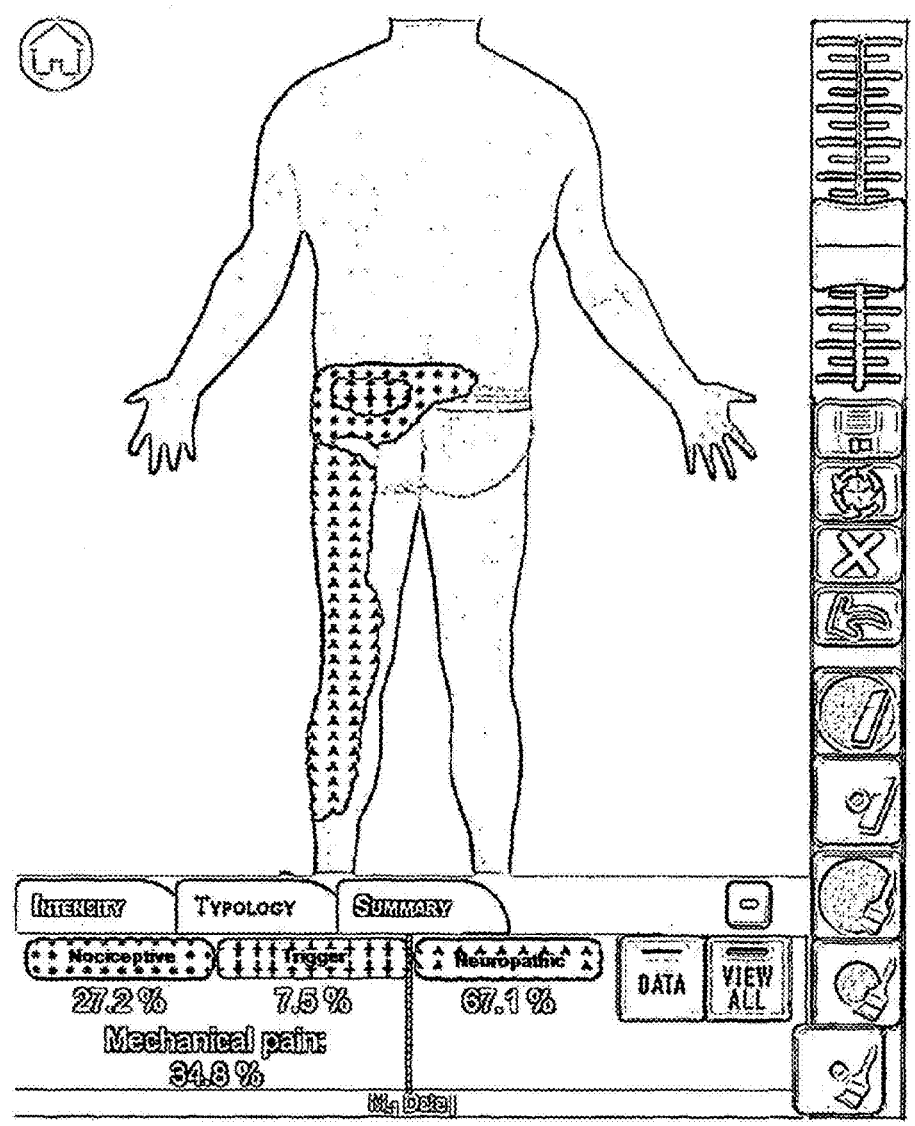
FIG. 16 is a screenshot illustrating an example of the mapping of types of pain.

In FIG. 16 (and FIG. 16a), the graphics functions on the right of the screen are identical to FIG. 15 (and FIG. 15a). At the bottom, it is now the "Type" tab that is activated in the application appSelec.

Types of Pain

The indicator relating to the type of pain can be defined by selection between four pain types, to each of which is assigned a corresponding color, for example according to Table TS52 below.

TABLE TS52

| Pain types | |
|---|---|
| Name | Color |
| Nociceptive pain | Pink |
| Trigger pain | Violet |
| Neuropathic pain | Yellow |
| Mechanical pain | none |

Only the zones that have a pain intensity can be typed. That is to say, a type can only be assigned to a zone that has a pain level. It is thus noted that the marked surface areas of FIG. 16 (and FIG. 16a) are included within those of FIG. 15 (and FIG. 15a). Moreover, the types are not exclusive, in the sense that there can be several types of pain in one and the same pain zone.

In the bottom part of FIG. 16 (and FIG. 16a), there are only three control buttons, which correspond to the first three types of Table TS52.

To each type of pain it is possible to associate a percentage of the corresponding calculated surface area, with respect to the total painful surface area. This is illustrated at the bottom of FIG. 16 (and FIG. 16a) in the corresponding color. The percentage of mechanical pain is obtained by adding the "nociceptive" and "trigger" percentages and rounding off the result.

In FIG. 16, the nociceptive pain ("NOCI") is represented by an area of dots spaced apart from each other; the trigger pain ("TRIG") is represented by an area of crosses spaced apart from each other; and the neuropathic pain ("NEURO") is represented by an area of spearheads spaced apart from each other.

In FIG. 16a, the nociceptive pain ("NOCI") is represented by an area colored pink; the trigger pain ("TRIG") is represented by an area colored violet; and the neuropathic pain ("NEURO") is represented by an area colored yellow.

The "View all" button of FIG. 16 (and FIG. 16a) serves to visualize the pain intensities superposed on the different types of pain.

Figure 17:
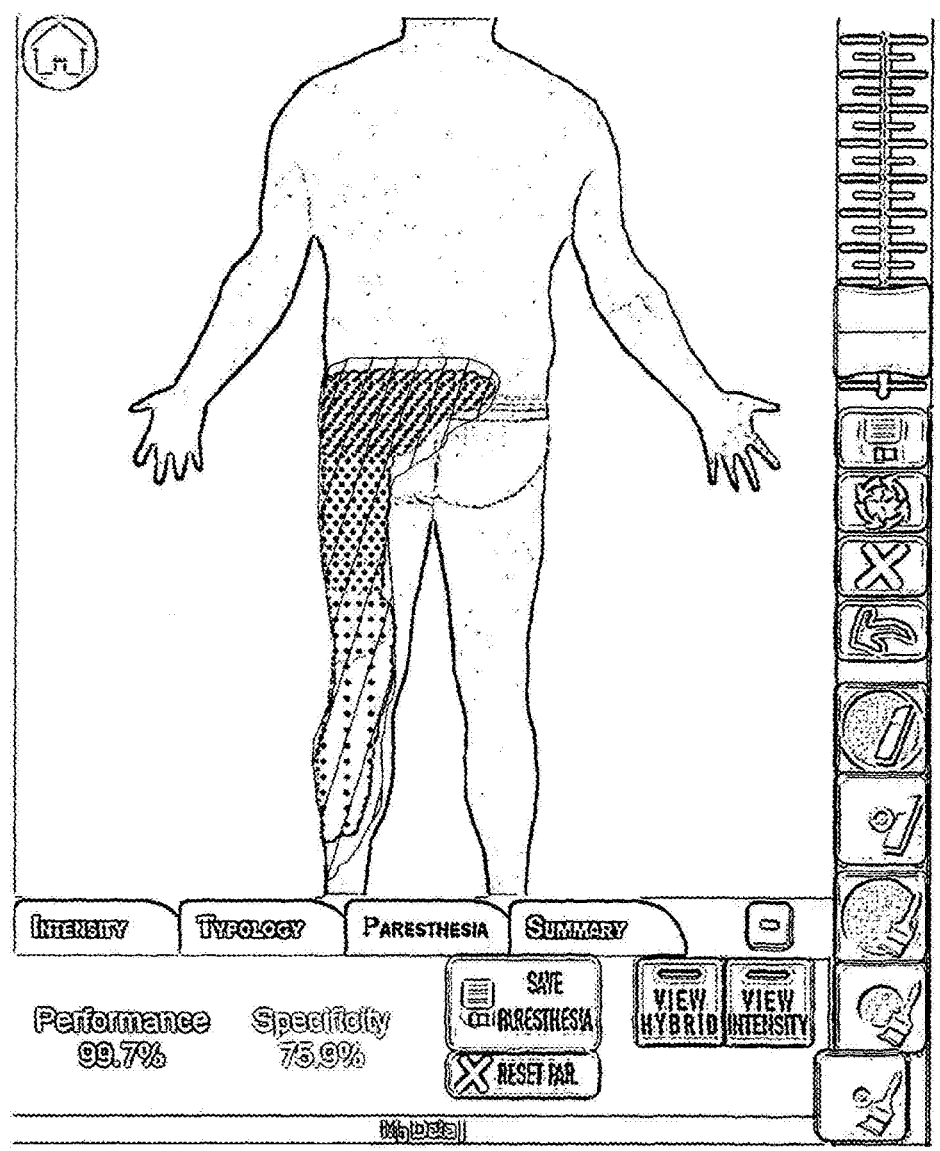
FIG. 17 is a screenshot illustrating an example of mapping the treatment of the pain by implanted stimulation, generating a "coverage of the painful zone" drawn by the patient and representing the sensation created by the neurostimulation or "paresthesia" device.

Reference is now made to FIG. 17 (and FIG. 17a). Here, the graphics functions on the right of the screen are configured as in FIGS. 15 and 16.

As regards the tabs of the horizontal panel (application appSelec), they could be the same in FIGS. 15, 16 and 17 (and FIGS. 15a, 16a and 17a), namely "Intensity", "Typology", "Paresthesia" and "Summary".

The applicant prefers that sections S5 and S6 are clearly differentiated, that is to say that:
section S5 is targeted specifically at the drawing and evaluation of the pre-treatment or post-treatment pains, whether neurostimulation is involved or not. The "Paresthesia" tab is thus deactivated, invisible or suppressed in the screens of section S5, cf. FIGS. 15 and 16 (and FIGS. 15a and 16a),
section S6 is dedicated to neurostimulation and has the four tabs "Intensity", "Typology", "Paresthesia" and "Summary", as shown in FIG. 17 (and FIG. 17a).
Section S6—Tool for Mapping the Paresthesias Generated by Implanted Neurostimulation for Analgesia ("Neuro-Mapping Locator")

Similarly to section S5, section S6 will manage the actions in the form of a history, by the application appHisto.

As before (FIG. 14 and FIG. 14a), the application appHisto defines an ordered list of patient visits, which are predefined, for example, as:
$M_{-1}$, $M_0$ (session on the day of the implantation), $M_{+1}$, $M_{+2}$, $M_{+3}$, $M_{+6}$, $M_{+12}$, $M_{+24}$ (follow-up visits).

After selection of a visit (or creation of a new visit), touching a "Go" button allows the launch of the actual map drawings.

At the bottom of FIG. 17 (and FIG. 17a), it is the "Paresthesia" tab that is activated in the application appSelec.

In FIG. 17, the paresthesia "PARES" generated on the patient by the neurostimulator is represented by an area of hatching. The area of hatching is superposed on the pain zones of FIG. 15.

In FIG. 17a, the paresthesia "PARES" generated on the patient by the neurostimulator is represented by an area colored green. This green-colored area is superposed on the pain zones of FIG. 15a.

By means of his map drawings, the patient will then depict or "portray" the paresthesias experienced and resulting from the spinal cord stimulation. Identically as for his pain, the patient will then "paint" his paresthesias, represented in green and/or with the aid of other graphical attributes.

Paresthesias

Neurostimulation is manifested by particular physical sensations, which can be described as pleasant tingling sensations. The mapping can also concern these sensations, which are of a paresthetic type.

The indicator relating to the paresthesias provides for differentiation between different stimulation programs or even between different types of implanted stimulation in one and the same individual. Thus, a distinction is made between spinal cord stimulation or SCS (cf. above) and peripheral nerve stimulation (PNS) by subcutaneous implantation opposite the painful zone, for example lumbar, intercostal, facial or occipital implantation (also known by the abbreviations Sub-Q Stim or PfNS (peripheral field nerve stimulation). Here too, different colors can be used, as indicated in Table TS53.

TABLE TS53

Paresthesia types

| Name | Color |
| --- | --- |
| SCS Spinal Cord Stimulation or Program 1 | Light green |
| PNS Peripheral Nerve Stimulation or Program 2 | Dark green |

Hybrid operation is possible, i.e. using the different types of stimulator simultaneously or in succession. On each occasion, the patient draws the cutaneous surface on which he feels the tingling characteristic of one or other type of neurostimulation.

FIG. 17 illustrates an example.

In the embodiment of FIG. 17 (and FIG. 17a), the paresthesia type is not indicated by a color on the silhouette displayed by the graphics tablet TG. It is specified when the other data of the image in FIG. 17 (and FIG. 17a) are saved.

In summary, if one compares the roles of sections S5 and S6:
- section S5 constitutes an analysis of the way in which the patient feels pain,
- section S6 moves on to an analysis of the patient's experience with respect to a delivered therapy, in this case implanted spinal cord stimulation, especially when the paresthesias generated by the implanted stimulation are made to vary. The variation of the paresthesias generated by the implanted stimulation can be effected either on the day of implantation of a stimulator, during the initial programming in real time in the operating unit, or over the course of the longitudinal follow-up.

Like section S5, this section S6 is based on a history relating to the patient. The welcome screen of section S6 is thus an ordered list of patient visits, as for FIG. 14 (and FIG. 14a). This screen is not shown again.

There are several ways of modifying the treatment of the patient (paresthesias), in particular:
- modifying the configuration of neuronal excitation of the neurostimulator; this involves modifying the stimulation program by varying either the electrical configuration of anode(s) and of cathode(s), or the amplitude/intensity of stimulation, or the impulse duration of the stimulation wave, or the stimulation frequency, or the distribution of current density on the different contacts if the generation of the current entails multiple sources, or a combination of these parameters; or
- modifying the position of the electrode in the cranio-caudal axis or else laterally, during its implantation.

The techniques of implanted analgesic neurostimulation will now be discussed.

Advanced Techniques of Implanted Analgesic Neuro-Stimulation

The technique of medullary stimulation proper acts on the spinal cord. The usual abbreviation is SCS, standing for spinal cord stimulation. A powerful technique, it can be used to relieve patients suffering from severe neuropathic pains. In this technique, a programmable generator emits electrical impulses in the direction of the nerve fibers of the spinal cord of a patient, by way of at least one multi-contact electrode. It acts directly on the central nervous system.

The stimulation electrode can be a monocolumn lead (at least two contacts), and it can be implanted percutaneously. It can be a multicolumn lead (at least two columns of contacts), in which case it is in principle put in place by surgery, the electrode having the shape of a disk wider than the monocolumn leads, which are cylindrical and in the form of wires.

The optimal positioning of the stimulation electrode is located at a certain region of the spinal cord in the vertebral canal, where the afferent projections of a peripheral zone of cutaneous pain are centralized (for example, a painful region of the lower limb projects in the spinal cord region at the level of thoracic vertebrae T9 to T11).

The technique of subcutaneous nerve stimulation is also known, which acts on the peripheral nervous system. The usual abbreviation is PNS, standing for peripheral nerve stimulation. This can be considered as an indirect spinal cord stimulation insofar as the subcutaneous nerve stimulation passes through the peripheral nerve fibers as far as the part of the spinal cord which is associated with the peripheral zone excited by the stimulation. In this case, the one or more electrodes implanted in the subcutaneous tissue are generally monocolumn leads (at least two contacts), although the use of a multicolumn lead is not formally excluded. The electrode is implanted opposite the painful zone.

In all cases, the electrode is connected to a neurostimulator implanted in the subcutaneous tissues of the abdominal region or of the buttocks. An associated external control box makes it possible to interrogate the implanted device by radio frequency and selectively activate its stimulation programs, using the electrical contacts of the electrode in order to generate an electric field of controlled voltage, intensity and spatial range. This electric field stimulates a neuronal population, which provokes a physical effect called "paresthesia", capable of providing relief from the pain. This physical effect is often felt by the patient as a pleasant tingling sensation when its takes the place of the pain sensation.

Until now, a physician had to use intuition and experience when choosing the electrodes and the neurostimulator to be implanted.

However, the choice of the one or more electrodes (and of the neurostimulators associated with them) is crucial. This is because the results are variable depending on the therapeutic tool used (electrodes of greater or lesser sophistication; percutaneous or surgical electrodes, conventional electrodes or electrodes of a new generation, monocolumn leads or multicolumn leads, electrodes with a greater or lesser surface coverage, etc.).

Indeed, the electrodes for direct spinal cord stimulation (SCS) are often effective when the indication is strictly established by an experienced implanter, in view of the fact that they act directly on the spinal cord and therefore the central nervous system. However, in at least some cases, they are not very selective. This is because the spinal cord accommodates bundles of nerve fibers which are assigned to different regions of the body and which are stimulated together. For example, an SCS electrode implanted in order to stimulate one side of the lower back will generally also excite the medullary neuronal population responsible for the innervation of the lower limb on the same side, which will produce useless paresthesia in an area that is not painful, since the pain, in this precise example, develops only at the expense of the axial component of the individual, i.e. at the lower lumbar level and not at the level of the limbs.

Conversely, the electrodes for peripheral nerve stimulation (PNS) may be less effective in some cases and act only indirectly on the spinal cord. However, they are more selective. Among the various bundles of nerve fibers accommodated by the spinal cord, only those corresponding to the zone where the PNS electrode is implanted are stimulated. It appears that there is also a phenomenon of accustomization (or tolerance) in respect of a PNS electrode, of which the stimulation loses its effect over the course of time.

The choice of the electrode is therefore a particularly difficult one. All the more so when one considers, on the one hand, the variety of electrode models on offer and, on the other hand, the variety of stimulation configurations permitted by each model. The programmer in fact permits numerous combinations of activation of the electrode contacts, for example with angular effects and effects focusing the generated electric field. By way of example, it may be noted that, taking into account only the number of possible combinations, independently of any notion of amplitude, of impulse duration, of stimulation frequency, etc., the options as regards the choice of contacts on a multicolumn lead with 16 pins exceed 49 million possible combinations for a given electrode implanted at a given level in a given individual and for a given indication.

For more details, reference may be made to the articles:
"*Transverse tripolar spinal cord stimulation: theoretical performance of a dual channel system*", Struijk J J. and Holsheimer, J. Med Biol Eng Comput, 34(4):273-279, 1996;
"*Spinal cord stimulation versus repeated lumbosacral spine surgery for chronic pain: a randomized, controlled trial*". North R B et al., Neurosurgery, 56:98-106, 2005;
"*Spinal cord stimulation versus conventional medical management for neuropathic pain: a multicentre randomized controlled trial in patients with failed back surgery syndrome*", Kumar K., et al., Pain, 132:179-88, 2007;
"*The effects of spinal cord stimulation in neuropathic pain are sustained: a 24-month follow-up of the prospective randomized controlled multicenter trial of the effectiveness of spinal cord stimulation*", Kumar K., et al., Neurosurgery, 63:762-70, 2008;
"*Back Pain, A Real Target for Spinal Cord Stimulation*", P. Rigoard et al., Neurosurgery 70:574-585, 2012.

With the aid of the functions described under section S5, the choice of the therapeutic tool is made according to measured parameters of quantification of the pain, such as the size of the surface area or else the location of the painful zone. The evaluation of these parameters is in fact a key step in permitting a suitable choice of the one or more electrodes to be implanted. This is a first step forward.

Section S6 is able to take us further, by providing a dynamic comparison of the painful zone and the zone of paresthetic coverage generated by the implanted stimulation.

The definition of one or more implanted neurostimulation devices in accordance with Table TS14 may comprise:
an identifier of the electrode and of the stimulator, which identifier completely defines the number and the distribution of its contacts,
the stimulation parameters (amplitude/intensity/impulse duration/stimulation frequency),
the characteristics of the generator (single source or multiple sources, etc.),
the number, type and position of implantation of the stimulation electrode(s) in the body and, generally, the vertebral canal of the patient (spinal cord stimulation),
the stimulation configuration of the contacts of the stimulator,
the anatomical and electrical characteristics of the implantation site and of the neuronal target (dimensions of the vertebral canal, distance of the electrode from the cord, implantation of the roots, thickness of the layer of cerebrospinal fluid interposed between the electrode and the neural tissue, shape of the canal, conductivity of the adjacent nerve tissues, etc.).

It is thus possible to record historically, as a function of the treatment, the development of the painful zone and the development in the relationship between the paresthetic zone and the painful zone, as will be seen below.

Action on the Programming of the Implanted Stimulation Electrode

The mapping makes it possible to compare the zone of coverage (in $cm^2$) of the paresthesias generated by the stimulator in relation to the pain zone (in $cm^2$). This makes it possible to calculate the coverage of the paresthesias on the pain zone. Thus, the clinician can reorganize the electric field of the stimulator, in principle in order to increase the coverage, by modifying the programming of the electrode.

Moreover, the mapping makes it possible to adapt the specificity of the paresthesias. It sometimes happens that the paresthesias cover both a pain zone and also a healthy zone. Thus, although a paresthetic coverage may be satisfactory (with respect to the painful target zone), the specificity of the paresthesias may not be. This situation arises in particular when the paresthesias cover the totality of a pain zone but also, in parallel, cover too large a healthy zone. In these conditions, the specificity of the paresthesias is generally unsatisfactory. By means of the mapping, the clinician will be able to reorganize the electric field of the stimulator in order to increase the specificity thereof.

This can be specified by considering groups of patients on whom advanced statistical analyses can be carried out: coefficient of correlation, distribution, studies of quantitative variables as a function of time, comparison of means, analysis of variance (ANOVA), in particular. It is possible, for example, to use the software SAS v 9.3, available in particular from SAS Institute Inc., 100 SAS Campus Drive, Cary, N.C. 27513-2414, USA. This software provides procedures (such as PROC MEAN and others) for statistically analyzing variables, and also their "normality" (conformity to Gauss's law).

Action on the Positioning of the Stimulator

The measurements of coverage/specificity of the paresthesias are very useful when they are carried out during an operation of implantation of the electrode in a patient. This is because the nervous system (central or peripheral) is extremely complex, and it is therefore often difficult to locate the ideal site for the positioning of an electrode. The graphics tablet TG allows a patient to be questioned in a quantitative and reliable way during the implantation. For this, the patient is given a local anesthetic but is conscious (or woken up), allowing the patient to cooperate with the medical team in order to delimit his paresthesias, irrespective of whether it is an electrode implanted surgically or percutaneously.

During the operation, the patient can indicate in real time, on the graphics tablet TG, the paresthesias felt on account of the fitted implant. According to the measurement of specificity on the basis of the map provided by the patient, it is possible to evaluate the suitability of the location of the electrode. If appropriate, the electrode can be repositioned in real time, with direct return of the patient, confirming the optimized paresthetic coverage of his painful zone.

This makes it possible to seek out the position of the electrode that is effective, or the most effective, in view of one or more paresthesia maps drawn by the patient.

Thus, during the operation, the positioning of the electrode can be adjusted as a function of a real-time interaction between the patient and the device of the invention (here the tablet), as a function of the comparisons between the paresthetic surfaces and the painful zones. On each occasion, the surgeon will receive a very vivid visual representation of this, which facilitates his decision on the positioning and/or programming of the electrode. It can thus be considered as a kind of "electronic stethoscope for the spinal cord", which first permits an interaction with the patient, but especially brings together an electrical screening of the fibers of the posterior cords (electrical configurations of stimulation, and position of the electrode) and the result, as regards what the patient feels, in terms of the pain and also the paresthesia.

According to one embodiment, the screen of the graphics tablet TG can comprise a dual display, with symmetry with respect to a central axis. One screen half allows the patient to depict or "paint" his pain. The other screen half allows the clinician to observe the manipulations made by the patient during the operation, and the calculations of coverage/specificity of paresthesias (in particular) which follow from this.

Alternatively, the graphics tablet TG serves only the patient. The display reserved for the clinician is then provided on a separate screen of another computer or of another graphics tablet.

SUMMARY

A summary showing all the data that has been collected for the patient can be displayed on the touch-sensitive screen in the "Summary" tabs of screens S5 and/or S6.

For screen S5, the display can in particular comprise the surface area by intensity of pain, the surface area by type of pain, and the overall painful surface area. These data can be simply collated in a list in text format.

To allow the clinician a visual assessment that is both quick and complete, the summary is preferably expressed in graph form, for example as described below ("Pain parameters Y").

For the summary of screen S6, the display can in particular comprise the surface area by intensity of pain, the surface area by type of pain, and the overall painful surface area, to which may be added, if appropriate, the surface data for the paresthesias generated by the implanted device, with the ratios defined above.

Here too, these data can be simply collated in a list in text format or, better still, expressed in graph form, for example as described below ("Treatment parameters X").

A button on the screen can allow switching between text display and graph display, which is the default display.

Advantages

In brief, the characterization by drawing of a pain zone results in a pain map specific to a given patient. The map can be dimensioned directly in $cm^2$ or else in percentage surface area of a patient (measurement in $cm^2$ of the pain zone in relation to the total surface area of a patient expressed in $cm^2$). It therefore entails a mapping that is much more sophisticated than the solutions proposed in the prior art, making it possible in particular to perform statistical calculations based on measurements of the real size of the patients.

Figure 14A:
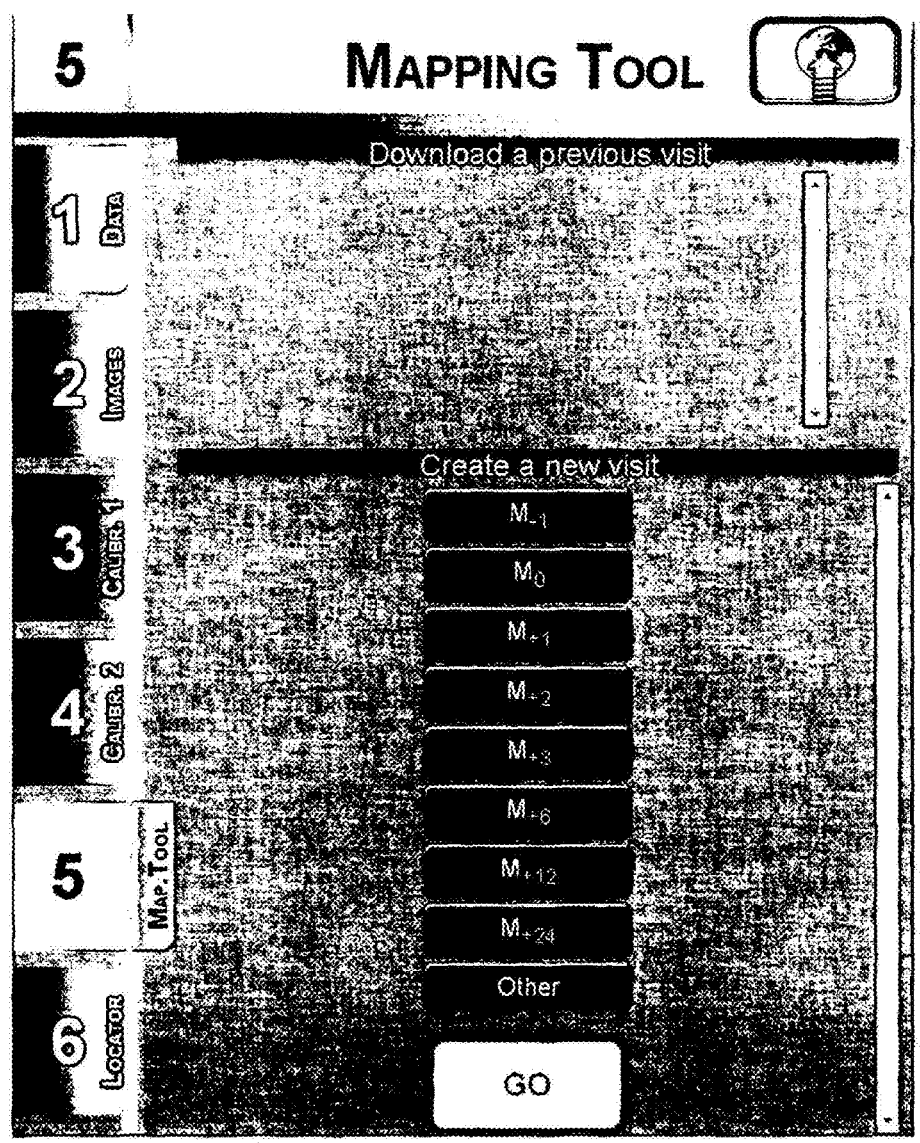
FIG. 14a is the original of FIG. 14 in color.

When the pain map is established, it can be saved directly on the central database CCS_DB, opposite the identifier of the visit in progress, defined on the screen of FIG. 14 (and FIG. 14a).

In other words, a map of the pain felt by a patient is represented metrically on the screen of the graphics tablet TG at the tab S5. This map can be recorded in the tablet TG and then transferred to the patient record in the computer CCS (CCS-T and/or CCS-I).

The map can be in 3D, as has been seen.

Thus, the characterization by drawing a zone of pain or of paresthesia can be repeated each time the patient visits the clinic. In this way, it is possible to monitor developments of the pain and of the pain coverage. It follows that each map of pain and/or of paresthesia produced during a visit is saved on the central database CCS_DB. The comparison of different maps and the changes in these maps over time allow in particular the clinician to analyze and better understand the pain felt by the patient. The clinician can thus adapt the treatment of the patient according to the maps produced.

The proposed map is much more advanced than a classical visual analog scale, with which it is difficult to analyze and understand the different components of the pain on reliable bases.

The mapping of the pain according to section S5 (NeuroPain'T) can be done at the patient's bedside, during a consultation, or even on an outpatient basis, in the form of a remote self-assessment. Other maps can be produced in an intra-operative mode, that is to say in the operating theater during the implantation of the stimulation electrode, as was seen in section S6, corresponding to the "Neuro-Mapping Locator".

ALTERNATIVE EMBODIMENTS

Generally speaking, the graphics tool of the invention preferably comprises a touch-sensitive screen that permits intuitive use by the patient, as has been seen. However, other types of pointing devices on a graphics screen are not excluded, at least in some cases.

The graphics tablet is normally visible to the patient and to the clinician. It is controlled by the clinician. For the screens to be touched by the patient, for calibration and mapping, the clinician gives control of the tablet to the patient.

In some situations, as has been seen, it may be desirable that the patient and the clinician do not seen the same thing. Depending on the desired degree of confidentiality, this can be done by dividing the screen of the graphics tablet into two symmetrical halves, or by providing an access control in the tablet, which access control reserves for the clinician the information that only he needs to know, or else by using a separate screen and/or computer for the clinician. In the latter case, the separate display can be managed by the graphics tablet TG, directly or through interaction with the central computer CCS (or one of them, or another computer) via the network.

The transfer of information can be done in particular in one of the following ways:
1. The data are created on the tablet and, if a WiFi connection (or other network connection) is available, the user can send data in real time to the work server.
2. If there is no connection, the tablet records the data locally and transmits them subsequently when connectivity (for example WiFi) becomes possible. The volume of data may then be limited by the available disk space of the tablet.

3. Another solution, when there is no connectivity, is to use a local PC connected to the tablet, which PC receives the data from the tablet before sending them itself to the work server.

Moreover, the graphics tablet TG may have to resort to the work server CCS-T to execute unwieldy calculating processes, as has been seen.

In addition, the operations carried out by the graphics tablet TG (at least when they are validated) are systematically stored in the global patient record of the central server CCS and/or of the work server CCS-T.

At another level, the invention may also be applied when treating pain other than by neurostimulation. For example, the application of topical agents such as capsaicin causes a burning sensation on the skin, with redness, which allows the patient to delimit the treated zone as felt by him.

Advanced Applications

The graphics application calculates the stimulated surface area Spar. The latter is compared with a corresponding painful surface area Sdol, for example the global painful surface area or more specifically the type of neuropathy. All or some of the following calculations can be carried out:

| Variable | Expression(s) | Comment |
|---|---|---|
| Scom | Spar ∩ Sdol | Surface area of the part common to the stimulated surface area Spar and to the painful surface area Sdol |
| Stot | Spar ∪ Sdol (Spar + Sdol) − Scom | Total surface area of the reunion of the stimulated surface area Spar with the painful surface area Sdol, without counting the common surface area Scom twice |

Different ratios can be calculated, preferably as follows:

The first ratio is a coefficient of performance Cperf:

$$Cperf=(Spar \cap Sdol)/Sdol=Scom/Sdol.$$

This coefficient Cperf can be seen as the ratio of paresthetic coverage in relation to the pain. It does not take into account the fact that Spar can be located outside of a pain. It thus calculates an effective paresthesia.

The second ratio is a coefficient of selectivity (Csel):

$$Csel=Scom/Spar$$

It expresses the ratio of useful paresthesias on the total surface area of the paresthesias.

The coefficient of selectivity Csel can be seen as a way of taking into account what is sometimes called "electric spreading" of the stimulation. This concept is not entirely understood at present. According to the applicant, this spreading stems from a diffusion or dispersion of the electric stimulation in the human body. Some of the spreading actually reaches painful areas. This is called "matching" spreading. Csel represents the proportion thereof.

The rest, in proportion (1−Csel), goes toward areas that are not painful; this is called "non-matching" spreading, i.e. it is not of any use and may even be detrimental to the comfort of the patient. The applicant considers that it is a relevant secondary indicator, once the demand in respect of performance appears satisfied. This point will be discussed in more detail below. The inverse of Csel can be seen as a coefficient of dispersion, Cdisp=Spar/Scom.

These advanced applications use "treatment parameters" of the form X* (their first letter is X), and also "pain parameters" of the form Y* (their first letter is Y).

The pain parameters (Y) concern the one or more pains and are calculated on the basis of surface area measurements carried out in section S5. An example of pain parameters is given in Table TS71 below.

TABLE TS71

| Parameters Y | |
|---|---|
| Parameter | Meaning |
| $Y_S$ | $Y_S$ is the reduction in a painful surface area from one visit to another |
| $Y_I$ | $Y_I$ is the reduction in pain intensity on a given surface area from one visit to another |
| $Y_{PC}$ | Change of typology or pain characterization on a given surface area from one visit to another |

Treatment Parameters; Stimulation by Electrodes

The treatment parameters (X) aim to represent the

| TS72 - Treatment parameters X | | |
|---|---|---|
| Parameter | Expression | Meaning |
| $X_P$ | Cperf | Parameter called "electrode efficacy", such as the efficacy of paresthetic coverage of pain, corresponding to the device performance |
| $X_S$ | Csel | Parameter of selectivity of the stimulation, corresponding to the device specificity |
| $X_{P3}$ | Spar(t2)/Spar(t1) | Parameter of persistence, corresponding to the change of the paresthetic surface area between the times t1 and t2. It is the change in the patient's perception of the electric stimulation over time, hence an evaluation of the phenomenon of tolerance | efficacy of the analgesic strategy employed, for example in the case of a stimulation device such as an implanted electrode. They are determined on the basis of measurements from section S5 and S6 for a patient.

Table TS72 below shows an example of this, in the case of electrodes for spinal cord stimulation.

All of these parameters are calculated and made available instantaneously, at a given time, by virtue of the real-time data processing effected by the software calculation application. The result can be presented in several visual forms in order to allow it to be read off quickly but accurately by the operator who fits the implant in the patient (for example a neurosurgeon, also called implanting clinician).

Particular Example

Let us consider a given patient. Between the visits $M_{-1}$ and $M_0$, this patient is fitted with a given electrode, in a given position, and with a given excitation configuration.

The raw data of surface areas depicted by the patient, as a function of the levels and types of pain, and the rate of coverage "Paresthesia/pain $M_{-1}$", are given in Table TS80 below.

TABLE TS80

| Pain level | Visit $M_{-1}$ Pain cm² | Visit $M_0$ post op | | | Visit $M_1$ Paresth. |
|---|---|---|---|---|---|
| | | Paresthesia cm² | Paresthesia/pain $M_{-1}$ % | Remaining pain cm² | |
| DL1 | 248 | 242 | 98% | 0 | |
| DL2 | 244 | 242 | 99% | 100 | |
| DL3 | 63 | 15 | 24% | 40 | |
| DL4 | 63 | 9 | 14% | 0 | |
| Sdol | 618 | — | | 140 | |
| Scom | | 508 | | | |
| Sout | | 247 | | | |
| Spar | | 755 | | | 689 |
| Stot | = Sdol + Sout | 865 | | | |
| Pain type | | | | | |
| Noci. | 122 | | | 0 | |
| Trig. | 126 | | | 0 | |
| Neuropath. | 370 | | | 140 | |
| Total | 618 | | | 140 | |

In this example:
the parameter Xp=Cperf=Scom/Sdol equals 0.82
the parameter XS=Csel=Scom/Spar equals 0.67
the parameter $X_{P3}$ considered between visit M1 (the total surface area of paresthesia is 689 cm²) and M0 (Spar=755 cm²) is 0.91 with persistence. This means that the paresthesia at M0 has survived almost in its entirety at the visit M1.

Weighted Coefficient of Performance

The coefficient of performance Cperf has been considered above, defined as:

$$Xp = Cperf = Scom/Sdol.$$

The applicant has observed that, at identical performance and specificity, a patient will probably not be satisfied by a paresthetic coverage that does not take account of the peak of his most intense pain.

It is for this reason that a weighted coefficient of performance $X_{PW}$ is also defined, for which the quantitative paresthetic coverage is determined separately for each zone of pain intensity. The coverage is weighted each time by a coefficient that depends on the zone of intensity, for example:

coefficient w=4 for very intense pain,
coefficient z=2 for intense pain,
coefficient y=1 for medium/moderate pain, and
coefficient x=0.5 for low pain.

Similarly, the applicant has observed that, at identical performance and specificity, a patient will perhaps not be satisfied by a paresthetic coverage that does not take account of his feelings according to the types of pain. For example, the weight 2 is given to trigger pains, and the weight 1 is given to nociceptive and neuropathic pains.

Directly Exploitable Index; Preferred Graphical Representation

In the following, so-called Manoé parameters as defined in Table TS83 below will be used.

TABLE TS83

| Manoé parameters | Possible values | Descriptions |
|---|---|---|
| Coef Perf | [0-1] | Corresponds to the ability of a device to generate paresthesias on an initial painful region. CP = (Sd∩Sp)/Sd |

TABLE TS83-continued

| Manoé parameters | Possible values | Descriptions |
|---|---|---|
| Weighted Coef Perf | [0-1] | Corresponds to the ability of a device to generate paresthesias weighted by the intensity of the covered painful region. CPP = [x * (Sp ∩ Sd Low) + y * (Sp ∩ Sd Medium) + z * (Sp ∩ Sd Intense) + w * (Sp ∩ Sd Very Intense)]/[x * (Sd Low) + y * (Sd Medium) + z * (Sd Intense) + w * (Sd Very Intense)] |
| Coef Selectivity | [0-1] | Corresponds to the tendency of a device to generate paresthesias targeted at the initial painful region. Csel = (Sd∩Sp)/Sp |

In this table, Sd_Low, Sd_Medium, Sd_Intense and Sd Very Intense each designate the surface areas of pain for each pain intensity, in increasing order.

Three indicators are now used that correspond respectively to the comparison of three parameters with three respective thresholds, for example according to Table TS85 below.

TABLE TS85

| Parameter | Example | Threshold | Conclusion | Symbol | Color |
|---|---|---|---|---|---|
| CPerf | 0.83 | 0.7 | Satisfactory | (+) | green |
| Weighted CPerf | 0.57 | 0.7 | Unsatisfactory | (−) | red |
| CSel | 0.71 | 0.77 | Unsatisfactory | (−) | red |

Figure 18:
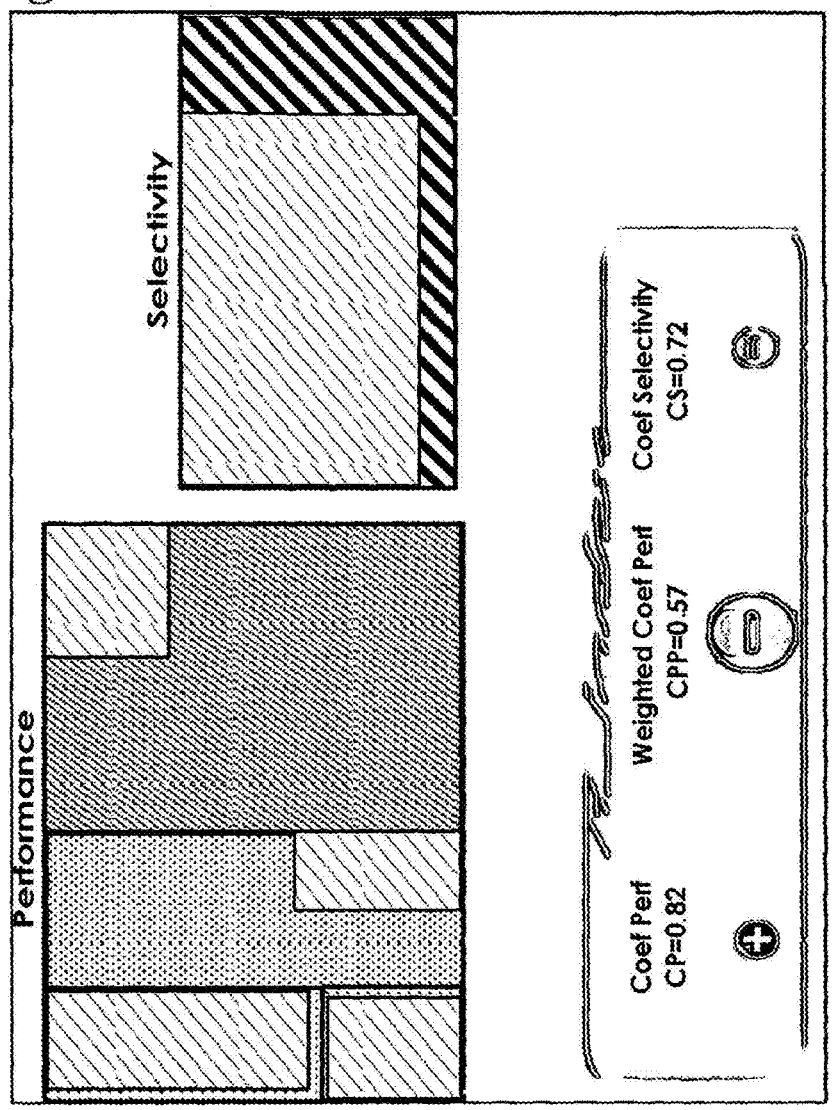
FIG. 18 is a screenshot illustrating a particularly advantageous tool called a Manoé diagram.
Figure 18A:
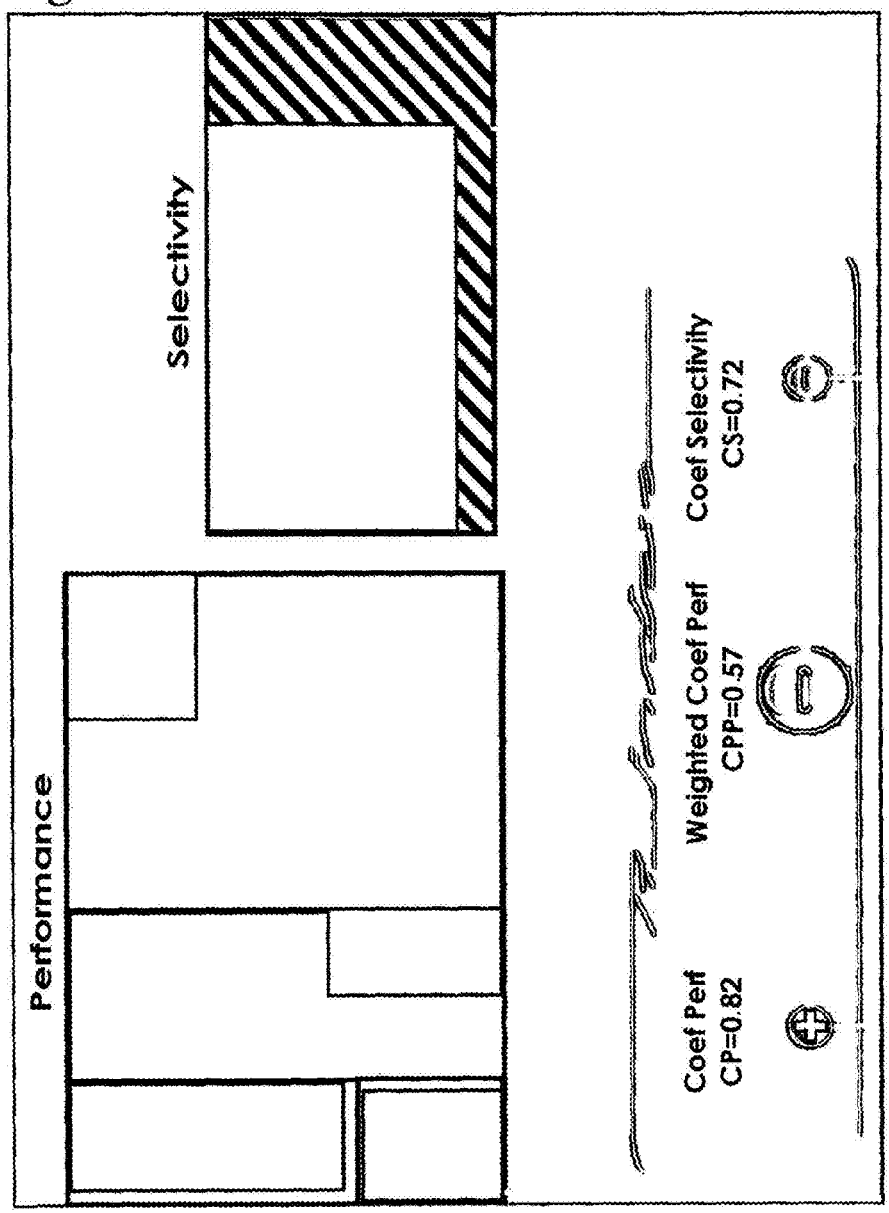
FIG. 18a is the original of FIG. 18 in color.

This set is here called the "R index" and is represented in this form, in FIG. 18, by telltale lights in the lower part, with reference to diagrams to which we will return.

The concept of the "R index" is based in the first instance on the following medical and practical considerations, in light of the actual properties of the electrodes:

(a) A minimum threshold of coverage of all the painful zones fixed at 70% (hence a coefficient of performance, Cperf, of 0.7) is regarded as acceptable to qualify as "satisfactory coverage" of the patient.

(b) By contrast, and this underlines the justification for using weighted coefficients as explained above, a patient who has 95% coverage of his pain, but for whom there is no coverage of the most painful small region estimated at 5% of the total painful surface area (the big toe, for example), will not feel his pain has been relieved. Despite an acceptable global coverage performance (X1), there is a risk of the stimulation being perceived as a failure.

Therefore, from a practical point of view, it will be considered that a minimum threshold of coverage of the most painful zone (coefficient of performance weighted for the pain intensity) also fixed at 70% is regarded as acceptable in order to qualify as "satisfactory" coverage, weighted for the pain intensity.

To give simple indicators in real time to the operator, green or red telltale lights (accompanied by the associated symbol "+" or "−"), corresponding to each parameter of the R index (Cperf, Weighted Cperf, Csel), are situated to the right of each score and defined as a function of the thresholds predefined above for performance and defined below for selectivity.

In other words:
a coefficient of global performance of above 0.7 (green telltale light) and a weighted coefficient of performance of below 0.7 (red telltale light) constitute a relative failure of the stimulation and entail a change of stimulation program, a repositioning of the electrode or a change of electrode, as a function of the anatomical parameters of the patient and of the technical parameters of the device,
a coefficient of global performance of below 0.7 (red telltale light) and a weighted coefficient of performance of above 0.7 (green) constitute a success of the stimulation on the most painful zone, but with still insufficient coverage of the pain as a whole. This will be regarded as a relative success of coverage, but one needing to be adapted secondarily to the expectations of the patient, at that time, and it will nonetheless be recommended that the stimulation program be changed or added to or even that the electrode be repositioned,
a coefficient of global performance of above 0.7 (green telltale light) and a weighted coefficient of performance of above 0.7 (green telltale light) constitute the ideal scenario and are evidence of successful coverage. It will thus be recommended to refrain from any change of stimulation program, any repositioning of the electrode or change of electrode.

The following points will be underlined:
The more the coverage selectivity sel approaches 100%, the greater the chances of the patient being satisfied, even at coefficients of performance (raw and weighted) regarded as "acceptable", that is to say above 0.7.
We are talking here about success of "coverage" (treatment parameters), not about the analgesic efficacy of the technique (pain parameters). This is because a paresthesia zone corresponds to how the patient feels the treatment; it is not certain that this paresthesia zone corresponds exactly to a zone of analgesic effect.
One of the potential advantages of this analysis of parameters is that it opens up the way to establishing a correlation between the treatment parameters and the pain parameters.

Once the study of the performance has been carried out, using the parameters Cperf and Weighted Cperf, the third parameter of the R index can be taken into consideration. This concerns the selectivity of the stimulation, studied using the selectivity coefficient Csel (a coefficient of dispersion could alternatively be used).

The zone of dispersion is represented in the diagram on the right of FIG. 18 by a hatched area of yellow and black stripes. Its surface area on the diagram is defined by the ratio between the surface area of dispersion Sout and the total surface area of the paresthesias Spar, which ratio is applied to the surface area of the base rectangle, which corresponds to the total surface area of the paresthesias generated.

In view of the current properties of the electrodes, the following medical and practical considerations will be taken as a basis:
A minimum threshold of selectivity of the stimulation fixed at 0.77 is regarded as acceptable in order to qualify as "selective coverage" of the patient.
A coefficient of selectivity of below 0.77, while not being totally unacceptable, will indicate that the stimulation will be uncomfortable for the patient, linked to an unsuitable and undesirable coverage ("non-matching spreading") of the stimulation on regions free of pain. As far as is possible, it will be recommended that the stimulation program is changed so as to be more selective, with the same performance, or even that the position of the electrode is modified as a function of the anatomical parameters of the patient and the technical parameters of the device, or even that the device is changed, if this dispersion is not tolerated by the patient.

The following points will be noted:
The concepts of selectivity and of dispersion cover the same entity, namely the ability of a device to generate the greatest possible useful paresthesia ("matching spreading"), which corresponds to the selectivity, or, expressed differently, the ability of a device to generate the least possible useless paresthesia ("non-matching spreading"), which corresponds to the dispersion. The parameter used here for the presentation of the Manoé diagram is the selectivity.

Importance of the R Index and of its Telltale Lights

The R index is a tool helping to make an almost immediate decision, in particular in intra-operative mode, when the clinician is in the process of implanting an electrode in a patient. The different situations are illustrated in Table TS86 below. They will be illustrated using the example of the telltale lights and diagrams of FIG. 18.

TABLE TS86

| Telltale lights | Conclusion | Recommendation |
|---|---|---|
| green green green (+++) | Perfect performance and selectivity | No change |
| green green red (++−) | Good performance, inadequate selectivity or excessive dispersion | Change program if inadequate, move electrode |
| green red green (+−+) | Improve coverage of most painful region | Change program if inadequate, move electrode if inadequate and if possible: change electrode |
| green red red (+−−) | Improve coverage of most painful region and the coverage specificity | Change program if inadequate, move electrode if inadequate and if possible: change electrode |
| red green green (−++) | Weighted performance good but not global. Good selectivity. | Change or add to program |
| red red green (−−+) | Selectivity good, but not performance | Change program if inadequate, move electrode if inadequate and if possible: change electrode |
| red red red (−−−) | Nothing working | Change program if inadequate, move electrode if inadequate and if possible: change electrode |

In this table, the expression "change program" signifies that the position of the electrode in the body of the patient is not modified; by contrast, the electrical stimulation configuration of the different contacts of the electrode is changed.

This "R index" is thus immediately informative to the implanter (anesthetist or surgeon). It is essential particularly in view of the many matters on which the implanter has to keep concentrating.

The representation can also use a diagram of paresthetic coverage, relative to the pain intensities on a given painful zone, taking the weighting into account.

As is illustrated on the left of FIG. 18, this can be a particular kind of graphic formed by juxtaposed rectangles in a large rectangle or "base" of standardized size. Each internal rectangle corresponds to a pain intensity: light blue, medium blue, orange and red, in the example given above. The surface area of each rectangle is defined by the weight attached to the pain intensity that it represents. As will be seen, the surface areas in light blue, medium blue, orange and red are in ratios of 0.5, 1, 2 and 4.

The surface areas of paresthetic coverage are illustrated in green, by rectangles included in each rectangle of pain intensity, for example in a corner thereof.

On the right, another diagram illustrates, with a green rectangle, the surface area of useful paresthesias Scom, surrounded by a striped square in yellow and gray, which corresponds to the surface Sout.

The applicant has chosen to call the representation in FIG. 18 a "Manoé diagram".

The combination of the "R index" and of diagrams constitutes a particularly powerful tool in helping to make a decision. The Manoé diagram is a remarkably effective graphical representation. Other graphical representations are conceivable.

Index F and Index RFG

What is called index F here is similar to an integral in time. It is a historical register, as a function of the treatments, of the changes in the painful zone and of the changes in the relationship between the paresthetic zone and the painful zone.

The index RFG is more complete at a clinical level and is of particular interest to the research clinician or scientist in that it allows the latter to establish, for the first time, relationships between the technical parameters of the treatment and the clinical efficacy of the analgesic therapy (clinical parameters of pain), with monitoring over time.

The parameters called RFG parameters will be used below. For the representation they are defined in percentages, according to Table TS87 below.

In this table, Sd designates a painful surface area and Sp designates a paresthetic surface area; t1 and t2 designate two visits, for example visits M0 and M1.

For a given visit, the percentages of intensity of residual pain in relation to the initial pain are used, for each intensity level:
% Low % Medium % Intense % Very Intense
Or, according to an equivalent notation
DL1% DL2% DL3% DL4%

The value Score_Int is the sum of these percentages of intensity, weighted by the weight associated with the intensity level concerned (x, y, z and w), the whole divided by w.

For example, x, y, z and w are 0.5, 1, 2 and 4, as before.

YI is then the reduction in this score of intensity between visit t1 and visit t2.

TABLE TS87

| Parameters RFG | Values | Description |
| --- | --- | --- |
| XP = Cperf (Performance) | [0-100%] | Represents the ability of a device to generate paresthesias on an initial painful region. Cperf = (Sd∩Sp)/Sd × 100 |
| XS = Csel (Selectivity) | [0-100%] | Represents the ability of a device to generate paresthesias specifically on the initial painful region. Csel = (Sp ∩ Sd)/Sp × 100 |

TABLE TS87-continued

| Parameters RFG | Values | Description |
| --- | --- | --- |
| XP3 (Persistence of the perception of paresthesia) | [0-100%] with 100% ceiling if ≥100% | Represents the survival, between 2 visits (t1, t2), of all the paresthesias generated by a device, between 2 visits (t1, t2). XP3 = $Sp_{(t2)}/Sp_{(t1)} \times 100$ |
| YS (Reduction of the surface area) | [0-100%] with 0% floor if ≤0% | Represents the % reduction of the surface areas of residual pain in relation to the initial pain, between 2 visits (t1, t2). YS = $[Sd_{(t1)} - Sd_{(t2)}]/Sd_{(t1)} \times 100$ |
| YI (Reduction in intensity) | [0-100%] with 0% floor if ≤0% | Represents the reduction in the % score of intensity weighted by the intensity level (x, y, z and w) of the residual pain ((x * % Low + y * % Medium + z * % Intense + w * % Very Intense)/w) in relation to the initial pain. YI = [Score $Int_{(t1)}$ − Score $Int_{(t2)}$]/Score $Int_{(t1)} \times 100$ |
| YPC (Change of typology) | [0-100%] | Represents the % variation in the predominant neuropathic/mechanical characteristic of the pain between 2 visits. YPC = [% $Neuropathic_{(t1)}$ − % $Neuropathic_{(t2)}$] |

Variants of Graphical Representations

The parameters used here can also be illustrated in the form of multiaxial polygonal diagrams, likewise called "star diagrams". In the following, there will generally be six parameters. This will therefore give a multiaxial hexagonal diagram each time.

Figure 19:
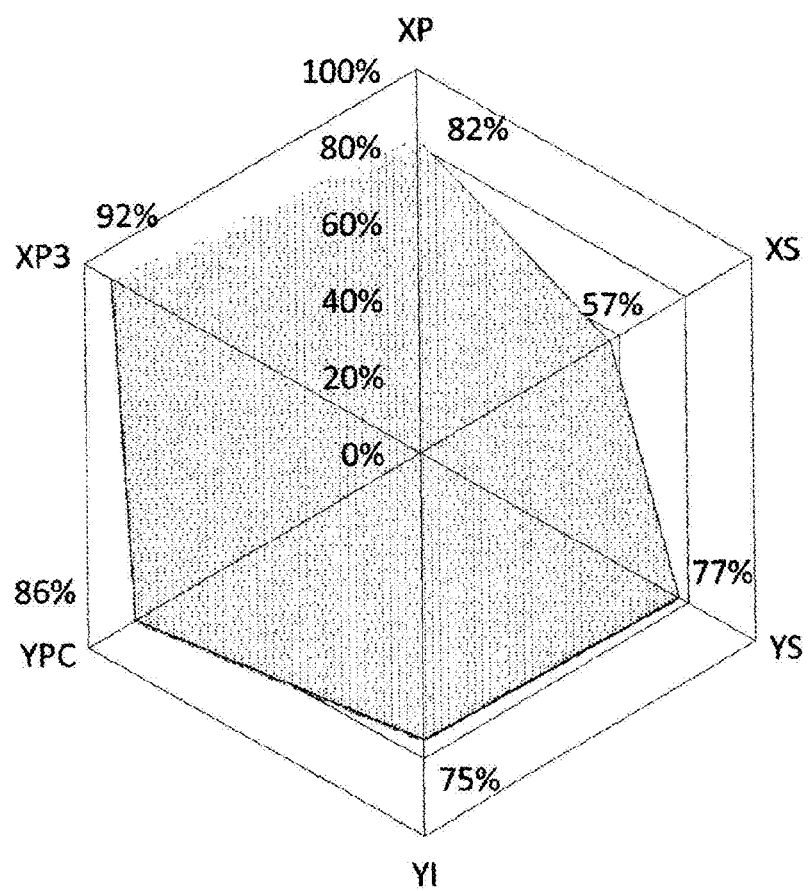
FIG. 19 is a screenshot showing a multiaxial hexagonal diagram for an electrode and a patient.
Figure 19A:
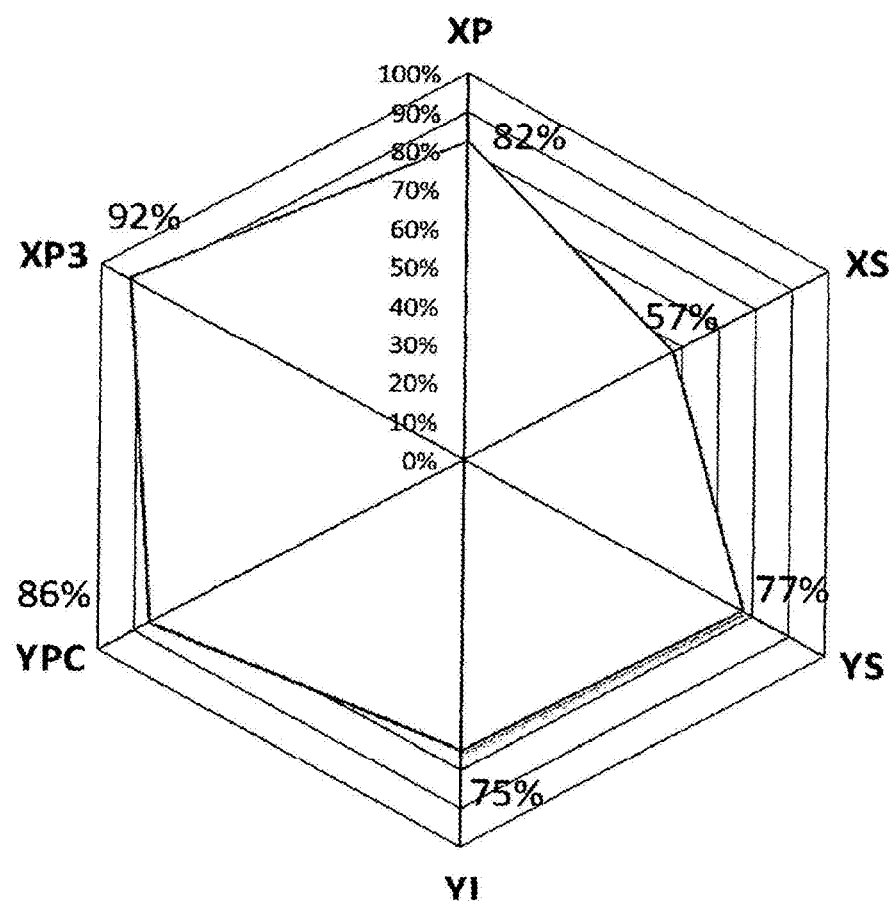
FIG. 19a is the original of FIG. 19 in color.

FIG. 19 is one such multiaxial hexagonal diagram, constructed from the X and Y parameters of Tables TS71 and TS72. FIG. 19 illustrates the evaluation of a therapy (SCS) at 3 months after the implantation.

It is a hexagonal graphical representation of the index RFG of a patient who suffers from refractory pain of the lumbar spine and in whom a multicolumn spinal cord stimulation electrode has been implanted, at a 3-month post-operative follow-up.

As regards the "treatment" parameters, it is first observed that there is a very satisfactory performance coverage of the painful surface area for this implanted electrode (Xp=82%). By contrast, the selectivity of the electrode remains very average, since just over half of the paresthesias generated is useful (Xs=57%), which means that 43% of the paresthesias generated are outside the painful region. There is practically no tolerance effect since the stability of the coverage over time is close to 100% (XP3=92%).

As regards the clinical parameters of the patient ("pains"), the relief appears very appreciable with a reduction in the painful surface areas of 77% (YS), accompanied by a reduction in pain intensity of 75% (YI). This analgesic effect permits a regression of the neuropathic component of the pain (YPC) of 86%, which component has hitherto been predominant.

Figure 20:
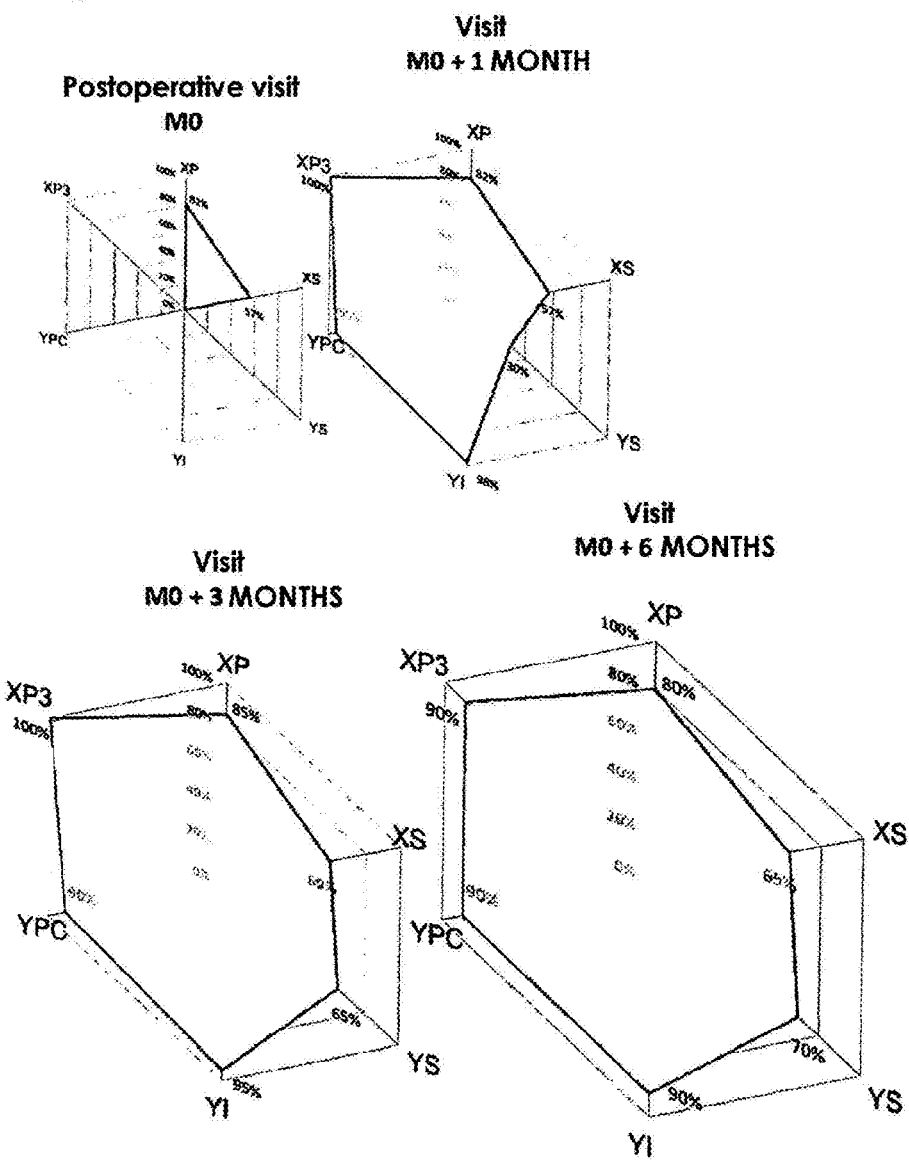
FIG. 20 is a screenshot showing in perspective a chronological sequence of diagrams similar to that of FIG. 19, for an electrode and a patient.
Figure 20A:
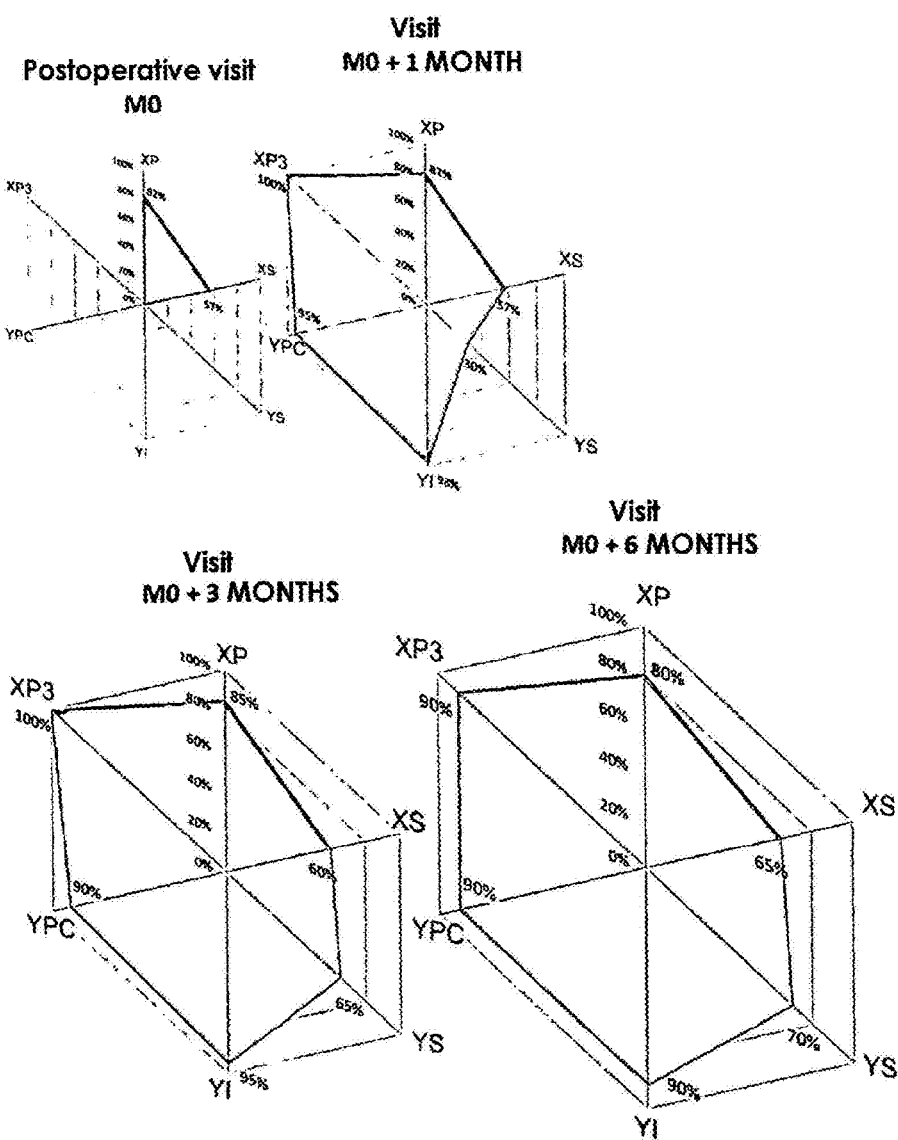
FIG. 20a is the original of FIG. 20 in color.

FIG. 20 is a perspective view linking four multiaxial hexagonal diagrams considered at M0, M0+1 month, M0+3 months and M0+6 months, for a given patient and a given electrode. M0 is an intraoperative visit and thus only has the axes XP and XS.

This constitutes an example of the index F and also of the index RFG.

This diagram shows a stability of the performance (XP) over time, while the selectivity (XS) has a discrete tendency to increase. The stability of the paresthetic coverage is good over time (XP3).

As regards the pain parameters, a progressive reduction in the painful surface areas is characterized by an increase in YS, which goes from 0 to 30% at 1 month after implantation and then to 70% at 6 months after implantation. The almost immediate and sub-optimal post-operative increase in YI is very probably evidence of good coverage, at once, of the regions with the most pain. It would thus be expected that the weighted coefficient of performance of the electrode in this patient, hence the R index (not shown on this diagram), would be high.

The pain typology changes drastically as from the first month after implantation, with a 95% reduction of YPC, which characterized a predominant mechanical component of the pain in this patient.

Figure 21:
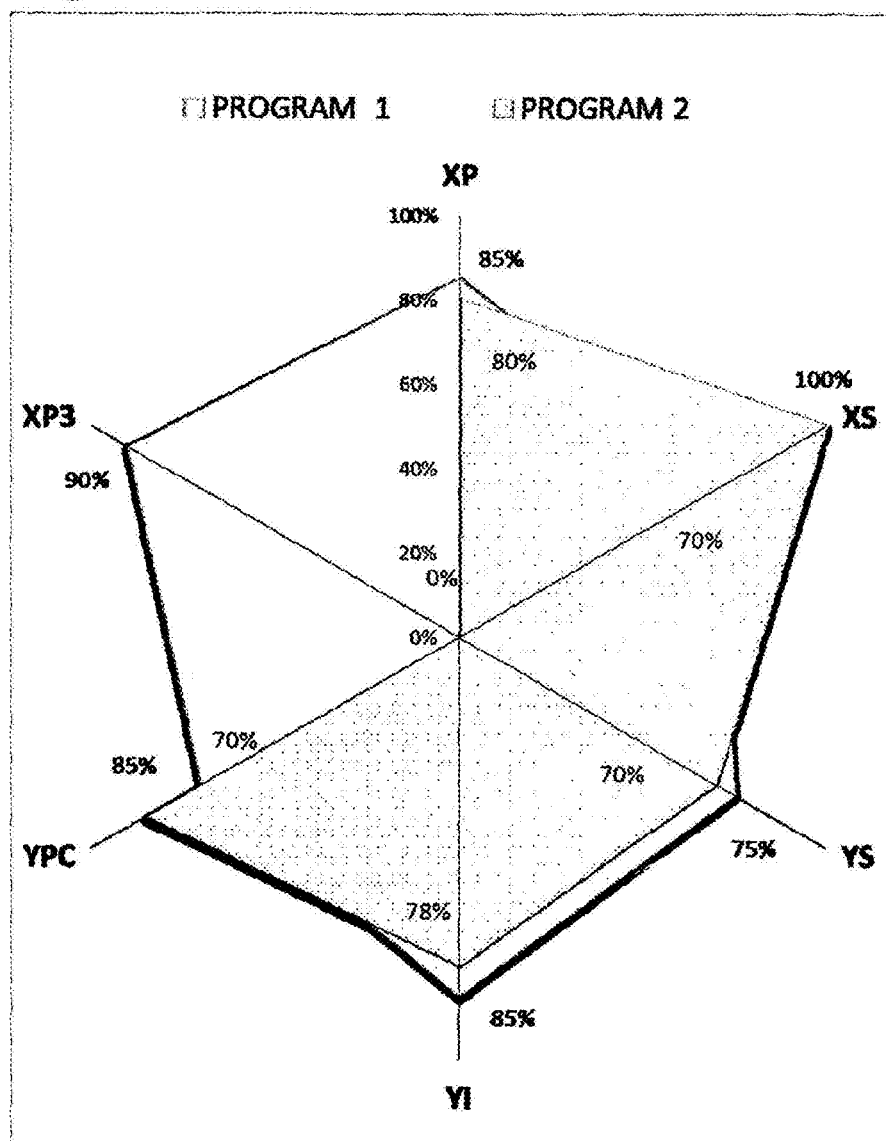
FIG. 21 is a screenshot showing a multiaxial hexagonal diagram on which two contours are superposed that relate to two different programs of excitation of the electrode for a patient.
Figure 21A:
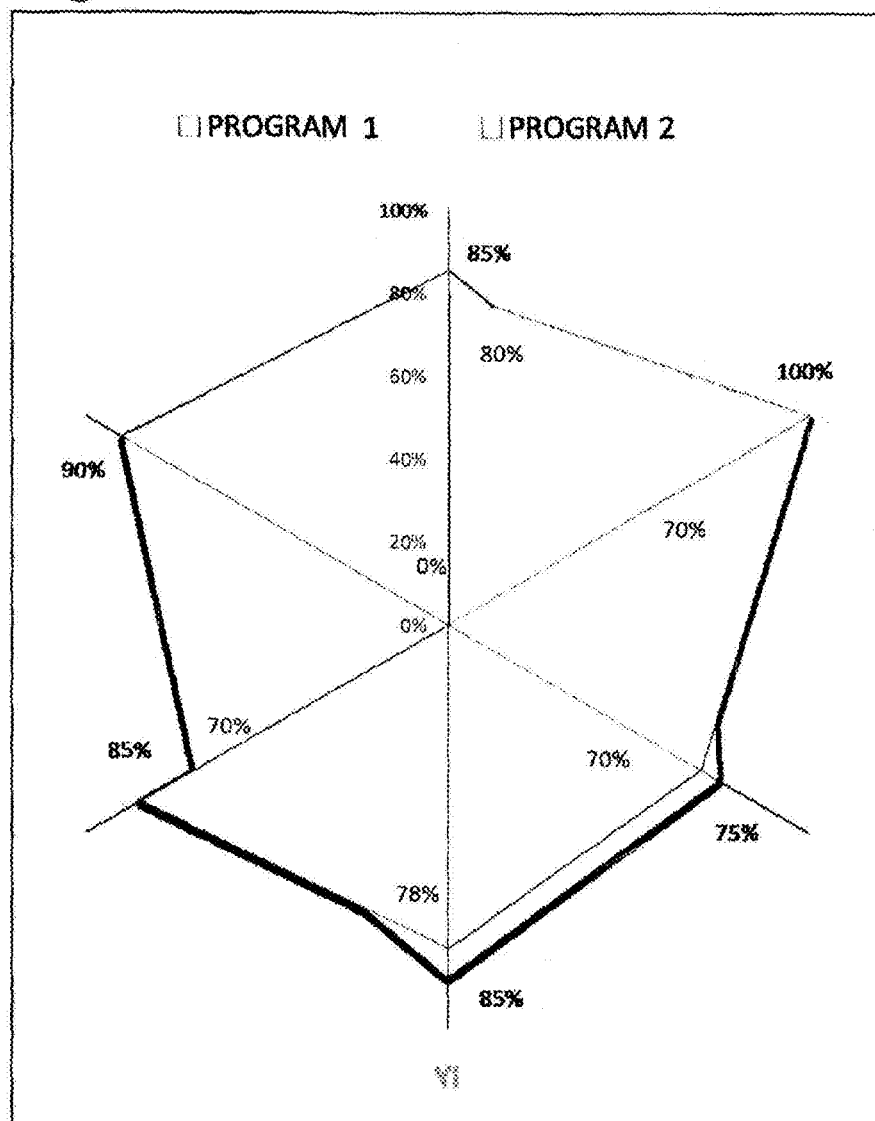
FIG. 21a is the original of FIG. 21 in color.

FIG. 21 is a multiaxial hexagonal diagram which compares two stimulation programs for one and the same patient and one and the same electrode.

This is a comparative representation of 2 indices RFG corresponding to 2 different programs (P1 and P2), tried out on one and the same patient. The patient was first on program 1, of which the selectivity was not satisfactory despite a good overall analgesic efficacy.

The construction of this diagram takes place one week after the commencement of program P2 (in green), which explains why there is still no parameter XP3 for program 2, since not enough time has passed.

It is observed that programs 1 and 2 have an almost comparable coverage performance. By contrast, the selectivity of program 2 is much higher than program 1.

The pain parameters are encouraging, with an almost comparable reduction in the painful surface areas (YS score slightly lower for program 2). The same applies to the pain intensity (85% for program 1 versus 78% for program 2).

It is interesting to note that the reduction in the neuropathic component of the pain is in favor of program 2 (YPC=85% versus 70%). As has been explained above, it is by contrast not possible to discern any phenomenon of tolerance to the paresthesias generated by program 2 just put in place.

Figure 22:
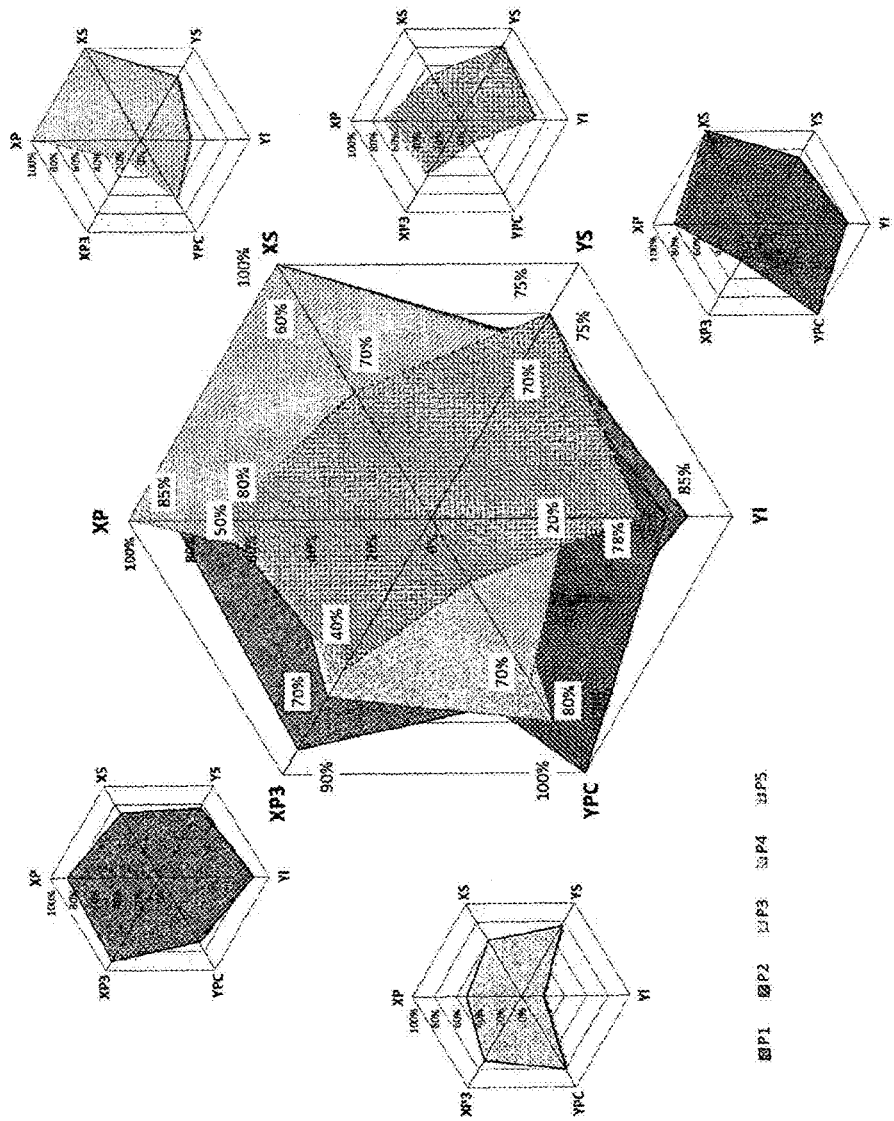
FIG. 22 is a screenshot showing, at the periphery, five multiaxial hexagonal diagrams corresponding to five different programs for excitation of the electrode for a patient and, at the center, in a larger multiaxial hexagonal diagram, the superposition of the five contours of the peripheral diagrams.
Figure 22A:
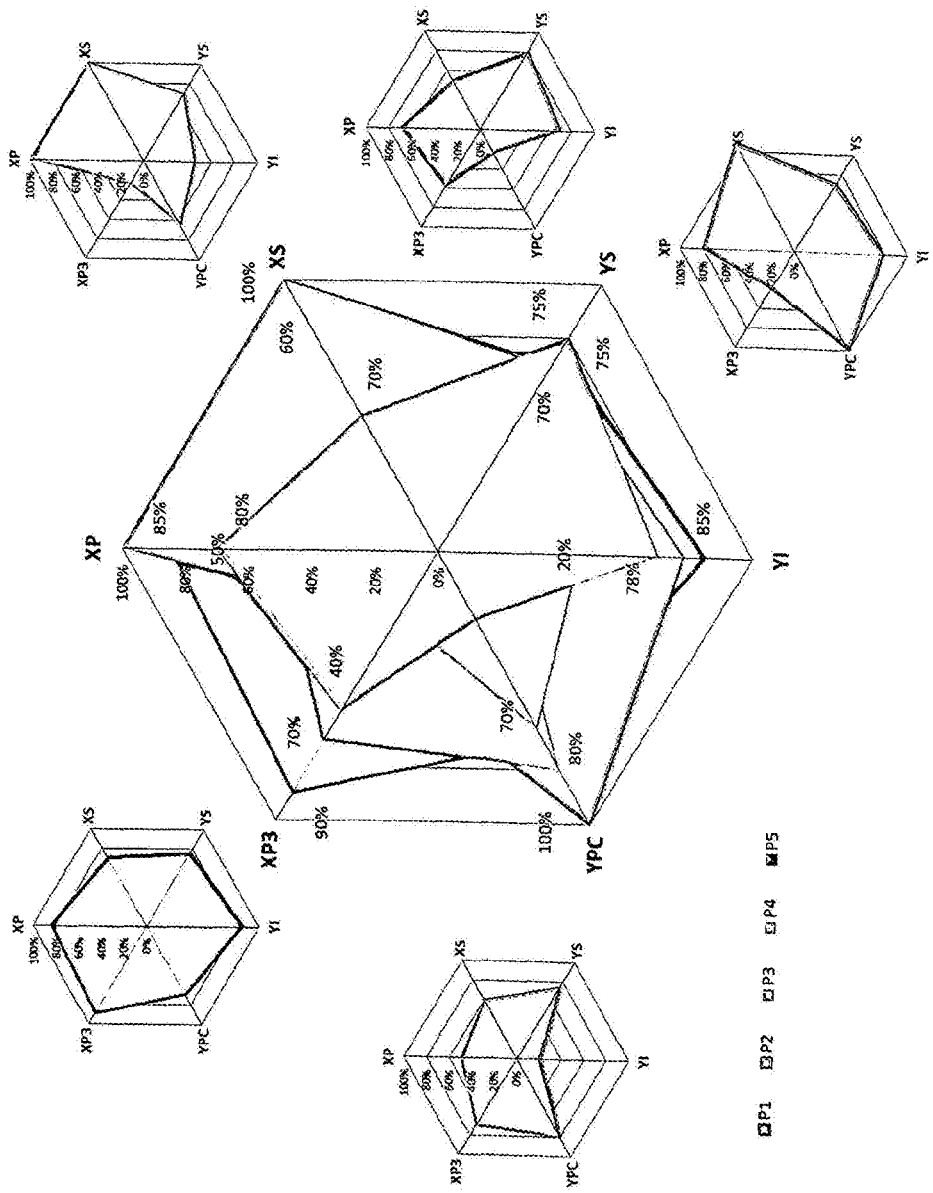
FIG. 22a is the original of FIG. 22 in color.

FIG. 22 comprises, at the periphery, five diagrams constructed like the one in FIG. 21, for five different programs P1 to P5, which are illustrated by different colors. At the center, the contours associated with the five programs are superposed in a single multiaxial hexagonal diagram.

Each program has been tried for one week, which has allowed the implanter to isolate two programs (P2 and P4) which are extremely powerful in terms of coverage but in which the efficacy is unfortunately transient (parameter XP3). These programs had to be abandoned for the final selection.

Program P5 was affected by the same problem of tolerance and especially a lack of selectivity, meaning that it was not possible to observe a change of pain typology (YPC).

Program P3 had average technical performance, unfortunately not accompanied by any significant reduction in pain intensity.

In the end it is thus program P1 (in violet) that has been selected for the definitive programming of this patient.

Neurostimulation of the central nervous system in particular comprises medullary neurostimulation, but also cortical neurostimulation. What is described here applies to all types of neurostimulation, with or without paresthesia.

Treatment Parameters X; Cases Other than Neurostimulation

Section S5 shows how the patient delimits his pain or pains. It can serve in situations other than treatment by neurostimulation. The following two non-limiting examples may be mentioned:
- spinal surgery such as removal of a herniated disk (treatment parameters in Table TS93)
- management of cervical pains, radiating toward the upper limb, by mechanical therapy of the McKenzie type (treatment parameters in Table TS94).

In these cases, the treatment parameters are not defined by paresthesias but by other technical variables associated with the treatment.

TABLE TS93

| Parameter | Definition | Procedure | Measurement |
|---|---|---|---|
| $X_1$ | Quality of result | Radicular disk decompression | Intraoperative examination of the decompressed root (flexibility, edema, color) |
| $X_2$ | Hernia volume removed | Pre/post-operative MRI or scan | Volumetric evaluation of the void left |
| $X_3(1)$ | Disk change over time | Post-operative MRI | Change in inflammatory state around disk (MRI signals "MODIC") |
| $X_3(2)$ | Disk change over time | Scan | Change in hydration of the disk (Pfirrmann classification) |
| $X_3(3)$ | Disk change over time | Standard X-rays | Change in disk height |
| $X_3(4)$ | Disk change over time | Dynamic X-rays | Change in disk stability in the sagittal plane |

$X_n$ treatment parameters - herniated disk

One or more of the parameters $X_3(1)$, $X_3(2)$, $X_3(3)$ and $X_3(4)$ of Table TS93 can be used.

TABLE TS94

Treatment parameters $X_n$ - Mechanical therapy (McKenzie)

| Parameter | Procedure |
|---|---|
| $X_1$ | Initial evaluation of the pain as a function of repeated positions imposed on the patient Positional/directional preference |
| $X_2$ | Analgesic effect remaining after one session |
| $X_3$ | Number of sessions needed to obtain lasting efficacy |

It thus becomes possible to compare a treatment by spinal cord neurostimulation with another, non-electrical treatment such as spinal surgery.

Multi-Patient Statistical Processing

For each patient, the graphics tablet TG and the computer CCS will make it possible to supply a database "Neuro-Data-Base", or Neuro-DB, with:
- personal clinical data on the patient;
- a representation of the patient in silhouette, with a conversion to real size of the pain zones and paresthesia zones felt by the patient;

drawing maps of the pain zones defined in intensity and type of pain;

drawings maps of the zones of paresthesia;

conversion of these maps on a metric basis to real dimensions;

monitoring of these maps over time;

the same monitoring as a function of the positioning of the electrode implanted in the patient;

the same monitoring as a function of the stimulation program used on the patient.

This Neuro-DB can be accommodated in the overall database CCS_DB.

The indices R, F and RFG, and their changes for each patient, will be calculated each time the database Neuro-DB is updated. Statistical studies can in particular be carried out on wide groups of patients, using statistical methods of stratification of classes, called "cluster" methods, or else computational methods called "data mining", in order to isolate predictors of responses within different subpopulations.

The data from quantitative evaluations of pain and paresthesia in the different patients are directly comparable, since they are expressed in real metrics.

Applications in Clinical Practice and for the Decisional Process of Therapeutic Strategy From the monitoring over time, it is possible to respond rapidly, by statistical analysis, to a question such as: in the presence of a given configuration of drawings of pain zones, which are defined in intensity and type of pain, what statistically were the most effective treatments in terms of choice of the implanted device(s), the positioning of the electrode and its programming? The data collected provide the response.

By compiling statistical analyses of this type, it is possible to define recommended treatments as a function of each encountered configuration of pain intensity and pain type.

By using the invention as a tool for entry of quantitative information, with the Neuro-DB appended to it as an expandable storage tool, and by applying the concepts discussed above to the processing of data on a wide population, it becomes possible to recommend directly, in part at least, and for a given patient:

the type of electrode to be implanted, the position of its implantation, and its programming configuration.

The invention can be regarded as a dual tool for comparative measurement and evaluation of pains and of the possible devices implanted for analgesic effect in an individual, making it possible, by large-scale processing of the information using the appended Neuro-DB, to identify and then extract predictors of response to the therapy, on a target subpopulation, in order to guide future therapeutic choices for neurostimulation.

Each implantable device, for a given indication, on a given target population, can inherit a global index RFG. This global index RFG is comparable from one device to another.

Thus, each patient presenting a particular pain zone will be able to be preferentially assigned the device most suitable to the predictors of response that have been identified for this individual.

The above concerns the clinical aspects of the treatment of patients.

The comparisons between electrode models (implantation and programs) can be done on numerous patients. This opens up the way to tests of great interest to the whole community of healthcare professionals, from clinical researchers to electrode manufacturers, by way of the health authorities, such as the Haute Autorité de Santé in France.

SUMMARY OF THE ADVANTAGES AND SOLUTIONS AFFORDED BY THE INVENTION

As has just been illustrated, the applications deriving from the use of the invention, with reliable metrics, are many and novel and have major implications for the patient. It is thus possible:

To represent, instantaneously and synthetically, the performance of a delivered therapy, with the aid of quantitative technical parameters associated with the delivered therapy. This evaluation is permitted by the index R and the graphical representation of the so-called "Manoé" parameters.

To determine if this instant and initial "technical efficacy" is accompanied by a significant analgesic effect of the delivered therapy at a time t (FIG. 19), and to assess whether it is durable over time (FIG. 20), which is the purpose thereof. This time projection is permitted by the longitudinal evolution of the index RFG and, at the purely technical level, by the integration of the pure performance of the device over time, materialized by the index F.

As regards spinal cord stimulation more particularly, to modify the position and/or the programming of an electrode just implanted, with the patient awake during surgery, using the function of scanning the target medullary fibers (function of electronic spinal cord stethoscope), by assessing the instantaneous change in performance and in selectivity associated with a change of electrical configuration of the device or with an intra-operative modification of its position in the vertebral canal.

To modify the programming of this same device during the longitudinal monitoring of the patient over time, by assessing the changes in the treatment and pain parameters, on iterative and comparative indices RFG (FIGS. 21 and 22), as a function of the use of one program or another.

In extension, by using these functionalities not only at the individual level but projecting them to a large-scale level by virtue of multi-patient statistical processing, the proposed software tool permits the following applications:

The most recent and sophisticated devices comprise an electrode with 16, 20 or 32 contacts. For 16 contacts, there is a choice of electrical configurations of more than 49 million combinations, with constant stimulation parameters. This leads to difficulties in choice of programming, which can make their use very restrictive for the operator or even uncertain for the patient: it would be possible to determine, for each device and each program, the population subgroup susceptible of gaining the greatest benefit from it and, for this reason, for a given patient, it would thus be possible to refine the programming algorithms to include perspectives of automated programming. The purpose of the invention is to extract a certain number of predictors of response to such or such a program by secondary analysis of the data. This represents one of the major advantages of the Neuro-DB, coupled to this software.

Still in the context of spinal cord stimulation, the hope of ever more extensive and selective coverage, of optimized pain relief using the new generations of electrodes, should allow clinicians to potentially widen the relevant indications. However, the variability of the overall results of these techniques published to date illustrates the extent to which the selection of the patients, the choice of the type of neurostimulation and the choice of the type of material appear to be parameters that are just as decisive as the parameters of implantation and of programming of the electrodes. Finally, the concept of long-term response to these different techniques, in the context of chronic pain, has never been evaluated. The resulting medical and economic stakes impose a rationalization of the indications and, once again, will condition the choice of material.

It is therefore the linking of the proposed interactive tools to a multipatient statistical processing, permitted by the use of the Neuro-DB, that appears to be relevant and promising.

In this field of application, the aim is to identify prospectively, within the target populations of candidates for implanted neurostimulation, "surgical phenotypes" of responders, nonresponders and partial responders to one or other neurostimulation technique, in order to:

compare the different neurostimulation tools. This will make it possible to guide the choice of these tools, to rank the uses, and to make the prospective data available to the authorities in charge of the reimbursement of these devices;

isolate predictors of response to the technique, by computational modeling;

redefine, ultimately the indications and the choice of these techniques.

Supposing that a distribution of the above-described interactive support is effective in a large-scale clinical network, the rational evaluation of the different systems of implantable neurostimulation permitted by this inventive method will have a direct impact on the healthcare systems.

The invention is likewise capable of being expressed in the form of methods.

The steps of the use of the tool described here, in its different embodiments, can also be expressed in the form of a neurostimulation method, diagnostic method and therapeutic method, one or other before, during and/or after surgery, making it possible to identify and monitor the pain felt by the patient and the development of the pain, and to permit an indication toward a choice of therapy.

It is also possible to define a method of evaluating a painful surface area with regard to a medical device in order to evaluate the efficacy thereof.

The invention claimed is:

1. A tool assisting in the evaluation/monitoring of pain and of a treatment, comprising:
   a graphics tool (TG) equipped with a screen (102);
   a local application (TGapps) installed in the graphics tool for the purpose of displaying on the screen (102) a graphical representation (100) of a patient's body which includes target points located on the patient's body, while allowing a user to delimit a zone (104) on the graphical representation (100) displayed on the screen (102); and
   a control application (TGappmain) cooperating with the local application (TGapps) in order to record (CCSapps) the delimited zone (104) together with corresponding surface data,
   the control application (TGappmain) having a first mode (S5) in which the local application (TGapps) allows the patient to delimit pain zones,
   the control application having a second mode (S6) in which the local application (TGapps) allows the patient to delimit treated zones,
   the control application (TGappmain) being configured to activate graphical and/or numerical comparisons between surface areas of the pain zones and surface areas of the treated zones,
   which makes it possible to evaluate the pain and the effects of the treatment,
   wherein each graphical delimitation is realized by filling zones with selective graphical attributes, in particular of color, at least some of the zones being partially transparent.

2. The tool according to claim 1, wherein, in the first mode (S5), the local application (TGapps) is configured to allow a patient to delimit pain zones selectively according to the type and the intensity of the pain.

3. The tool according to claim 2, wherein the types of pain comprise at least some of the types from the following group: nociceptive pain, trigger pain, neuropathic pain, mechanical pain.

4. The tool according to claim 1, wherein the treated zones correspond to paresthesia zones resulting from the excitation by a neurostimulation device implanted in the patient, and in that, in the second mode (S6), the local application (TGapps) is configured to allow paresthesia zones to be delimited selectively depending on whether the device is a neurostimulation electrode of the central nervous system or a neurostimulation electrode of the peripheral nervous system.

5. The tool according to claim 1, wherein the local application (TGapps) is configured to evaluate first surface data (Sdol) relating to at least one pain zone and second surface data (Spar) relating to at least one paresthesia zone, while the control application (TGappmain) is configured to compare the first and second surface data and also to calculate a rate of paresthetic coverage and a rate of specificity of the paresthetic coverage,
   which allows the paresthetic coverage to be adapted by improving the specificity.

6. The tool according to claim 1, wherein the local application (TGapps) is configured to allow a real metric to be assigned to said graphical delimitations.

7. The tool according to claim 6, wherein the real metric is obtained by applying a real scale to a silhouette (100) of the patient, on the basis of a measured real size of the patient.

8. The tool according to claim 6, wherein the real metric is obtained by processing images of the patient that are obtained from medical imaging.

9. The tool according to claim 1, wherein the local application (TGapps) is provided with a functionality for splitting the screen (102) into two zones, one for the patient, and the other for medical personnel, and on which zones the mode of display of at least some of the data is different.

10. The tool according to claim 1, wherein the control application (TGappmain) is configured to control a patient auto calibration function (appCalib2) for determining deviations between a plurality of target points each designated by contact on the physical body of the patient and corresponding points indicated by the patient pointing to the cartographic representation (100) displayed on the screen (102), while the delimitation, on the screen (102), of a zone (104) on the cartographic representation (100) by the patient is modified as a function of the patient auto calibration deviations (appCalib2).

11. The tool according to claim 1, wherein the control application (TGappmain) is configured to call up a patient/screen calibration function (appCalib1) for determining deviations between the target points located on the patient and displayed in graphical representation (100) of the patient's body on the screen (102) and zones of the touch-sensitive screen (102) that the patient actually touches, while the delimitation, on the screen (102), of a zone (104) on the cartographic representation (100) by the patient is modified as a function of the patient/screen calibration deviations (appCalib1).

12. The tool according to claim 1, wherein the data relating to each graphical delimitation and to surfaces of the patient's body are stored in a dated record attached to a patient file.

13. The tool according to claim 1, wherein the graphics tool (TG) is set up in a network with at least one other computer (CCS), in a manner permitting mobility.

14. The tool according to claim 13, wherein the central computer (CCS) is equipped with applications (CCSapps) for managing a database (Neuro-DB) and of performing statistical analyses on the data of this base.

15. The tool according to claim 14, wherein the statistical analyses on the data of said base (Neuro-DB) are configured to supply predictors of treatment, as a function of subpopulations of patients.

16. The tool according to claim 14, wherein the statistical analyses on the data of said base (Neuro-DB) are configured to supply comparative tests on different electrode models.

17. A tool assisting in the evaluation/monitoring of pain and of a treatment, comprising:
   a graphics tool (TG) equipped with a screen (102);
   a local application (TGapps) installed in the graphics tool for the purpose of displaying on the screen (102) a graphical representation (100) of a patient's body which includes target points located on the patient's body, while allowing a user to delimit a zone (104) on the graphical representation (100) displayed on the screen (102); and
   a control application (TGappmain) cooperating with the local application (TGapps) in order to record (CCSapps) each delimited zone (104) together with corresponding surface data,
   the control application (TGappmain) having a first mode (S5) in which the local application (TGapps) allows the patient to delimit pain zones,
   the control application having a second mode (S6) in which the local application (TGapps) allows the patient to delimit treated zones,
   the control application (TGappmain) being configured to activate graphical and/or numerical comparisons between surface areas of the pain zones and surface areas of the treated zones,
   which makes it possible to evaluate the pain and the effects of the treatment, wherein the local application (TGapps) is configured to determine, between the results of two visits:
     a coefficient of raw performance,
     a coefficient of weighted performance, as a function of the relationship between a treatment zone and zones of pain intensity, and
     a coefficient of specificity/dispersion, as a function of the relationship between the treatment zone and at least some of the zones of pain intensity,
   all of these coefficients (R index) providing a powerful indicator of the suitability of a treatment.

18. The tool according to claim 17, wherein the coefficients are represented graphically by telltale lights, including a comparison with respective thresholds, accompanied by at least one diagram of rectangles representing, on the one hand, the relationships between the zones of pain intensity and the part of the treatment zone which respectively affects them, and, on the other hand, the part of the treatment zone which does not affect at least some of the zones of pain intensity (FIG. 18).

19. A tool assisting in the evaluation/monitoring of pain and of a treatment, comprising:
   a graphics tool (TG) equipped with a screen (102);
   a local application (TGapps) installed in the graphics tool for the purpose of displaying on the screen (102) a graphical representation (100) of a patient's body which includes target points located on the patient's body, while allowing a user to delimit a zone (104) on the graphical representation (100) displayed on the screen (102); and
   a control application (TGappmain) cooperating with the local application (TGapps) in order to record (CCSapps) each delimited zone (104) together with corresponding surface data,
   the control application (TGappmain) having a first mode (S5) in which the local application (TGapps) allows the patient to delimit pain zones,
   the control application having a second mode (S6) in which the local application (TGapps) allows the patient to delimit treated zones,
   the control application (TGappmain) being configured to activate graphical and/or numerical comparisons between surface areas of the pain zones and surface areas of the treated zones,
   which makes it possible to evaluate the pain and the effects of the treatment,
   wherein the local application (TGapps) is configured to determine, between the results of two visits:
     at least three coefficients (YS, YI, YPC) representing, respectively, the reduction of the surface area of pain, the reduction of the pain intensity, and the change of typology of the pain, and
     at least three coefficients (XP, XS, XP3) representing, respectively, the performance of the treatment device, the selectivity of the treatment device, and the duration of the effects of the treatment device,
   all of these coefficients (index RFG) providing another powerful indicator of the suitability of a treatment.

20. The tool according to claim 19, wherein the coefficients are represented graphically in the form of at least one multiaxial polygonal diagram.

21. The tool according to claim 19, wherein the multiaxial polygonal diagram supports the representation of at least two groups of said coefficients, with different graphical attributes, in particular of color, the two groups being related to at least partially different treatment conditions.

22. The tool according to claim 19, wherein the graphical representation comprises at least two juxtaposed multiaxial polygonal diagrams, corresponding to at least partially different treatment conditions or different times.

\* \* \* \* \*